United States Patent
Shiratori et al.

(10) Patent No.: US 9,493,744 B2
(45) Date of Patent: Nov. 15, 2016

(54) METHODS FOR VIRAL INACTIVATION AND OTHER ADVENTITIOUS AGENTS

(71) Applicant: Genentech, Inc., South San Francisco, CA (US)

(72) Inventors: Masaru Ken Shiratori, Burlingame, CA (US); Robert David Kiss, San Mateo, CA (US); Hardayal Prashad, Richmond, CA (US); Raquel Iverson, Pacifica, CA (US); Justin Bourret, San Francisco, CA (US); Michael Kim, San Francisco, CA (US); Salim Charaniya, Encinitas, CA (US)

(73) Assignee: GENENTECH, INC., South San Francisco, CA (US)

( * ) Notice: Subject to any disclaimer, the term of this patent is extended or adjusted under 35 U.S.C. 154(b) by 346 days.

(21) Appl. No.: 13/844,051

(22) Filed: Mar. 15, 2013

(65) Prior Publication Data

US 2013/0344570 A1 Dec. 26, 2013

Related U.S. Application Data

(60) Provisional application No. 61/662,349, filed on Jun. 20, 2012.

(51) Int. Cl.
*C12Q 1/70* (2006.01)
*C12N 7/00* (2006.01)
*C12N 1/36* (2006.01)

(52) U.S. Cl.
CPC . *C12N 7/00* (2013.01); *C12N 1/36* (2013.01); *C12N 2750/14061* (2013.01)

(58) Field of Classification Search
None
See application file for complete search history.

(56) References Cited

U.S. PATENT DOCUMENTS

| | | | |
|---|---|---|---|
| 4,153,509 A * | 5/1979 | Schwartz | 435/129 |
| RE30,985 E | 6/1982 | Cartaya | |
| 4,339,216 A | 7/1982 | Bell | |
| 4,560,655 A | 12/1985 | Baker | |
| 4,657,866 A | 4/1987 | Kumar | |
| 4,767,704 A | 8/1988 | Cleveland et al. | |
| 4,816,567 A | 3/1989 | Cabilly et al. | |
| 4,927,762 A | 5/1990 | Darfler | |
| 5,091,178 A | 2/1992 | Hellstrom et al. | |
| 5,122,469 A | 6/1992 | Mather et al. | |
| 6,180,401 B1 | 1/2001 | Chen et al. | |
| 2003/0180766 A1 * | 9/2003 | Farnet et al. | 435/6 |

FOREIGN PATENT DOCUMENTS

| | | |
|---|---|---|
| EP | 0 117 058 B1 | 8/1984 |
| EP | 0 117 060 A2 | 8/1984 |
| EP | 0 117 060 A3 | 8/1984 |
| EP | 0 307 247 A2 | 3/1989 |
| EP | 0 307 247 A3 | 3/1989 |
| EP | 0 307 247 B1 | 3/1989 |
| EP | 0 404 097 A2 | 12/1990 |
| EP | 0 404 097 A3 | 12/1990 |
| EP | 0 404 097 B1 | 12/1990 |
| WO | WO-87/00195 A1 | 1/1987 |
| WO | WO-90/03430 A1 | 4/1990 |
| WO | WO-91/08291 A2 | 6/1991 |
| WO | WO-91/08291 A3 | 6/1991 |
| WO | WO-93/11161 A1 | 6/1993 |
| WO | WO 2013/192395 A1 | 12/2013 |

OTHER PUBLICATIONS

Awad. "Fouling of Heat Transfer Surfaces," Chapter 20 in *Heat Transfer: Theoretical Analysis, Experimental Investigations and Industrial Systems*, pp. 505-542, (2011).
Barnes et al. "Methods for growth of cultured cells in serum-free medium," *Anal. Biochem.* 102:255-270, (1980).
Cao et al. "Identification and Root Cause Analysis of Cell Culture Media Precipitates in the Viral Deactivation Treatment with High-Temperature/Short-time Method," *Journal of Pharmaceutical Science and Technology* 67(1):63-73, (Jan. 2013).
Chothia et al. "Canonical structures for the hypervariable regions of immunoglobulins," *J. Mol. Biol.* 196:901-917, (1987).
Clackson et al. "Making antibody fragments using phage display libraries," *Nature* 352:624-628, (Aug. 15, 1991).
DePalma. "Quantifying Cell Culture Media Quality," *Genetic Engineering & Biotechnology News* 31(2):28-32, (Jan. 15, 2011).
Gething et al. "Cell-surface expression of influenza haemagglutinin from a cloned DNA copy of the RNA gene," *Nature* 293:620-625, (Oct. 22, 1981).
Graham et al., "Characteristics of a human cell line transformed by DNA from Human Adenovirus type 5," *J. Gen. Virol.* 36:59-72, (1977).
Graham et al., "A new technique for the assay of infectivity of human adenovirus 5 DNA," *Virology* 52:456-467, (1973).
Ham et al., "Media and growth requirements," *Methods in Enzymology* 58:44-93, (1979).
Hammerling et al., "Research Monographs in Immunology," vol. 3, in *Monoclonal Antibodies and T-Cell Hybridomas*, Elsevier, N.Y., pp. 563-587, (1981).
Holliger et al., "Diabodies": Small bivalent and bispecific antibody fragments, *Proc. Natl. Acad. Sci. USA* 90:6444-6448, (Jul. 1993).
International Search Report mailed on Aug. 21, 2013, for PCT Application No. PCT/US2013/046756, filed on Jun. 20, 2013, 3 pages.
Jones et al., "Replacing the complementarity-determining regions in a human antibody with those from a mouse," *Nature* 321:522-525, (May 1986).
Keown et al., "Methods for introducing DNA into mammalian cells," *Methods in Enzymology* 185:527-537, (1990).
Kiss, R. "Practicing safe cell culture: applied process designs for minimizing virus contamination risk," *PDA J. Pharm. Sci. and Tech.* 65:715-729, (2011).

(Continued)

*Primary Examiner* — Michelle S Horning
(74) *Attorney, Agent, or Firm* — Morrison & Foerster LLP

(57) ABSTRACT

The invention provides for methods of viral inactivation using high temperature short time (HTST) treatment and adjustment of various parameters such that generation of precipitate and depositions of precipitate are reduced and/or minimized.

39 Claims, 16 Drawing Sheets

(56) References Cited

OTHER PUBLICATIONS

Köhler et al. "Continuous cultures of fused cells secreting antibody of predefined specificity," *Nature* 256:495-497, (Aug. 7, 1975).
Köhler et al., "Derivation of specific antibody-producing tissue culture and tumor lines by cell fusion," *Eur. J. Immunol.* 6:511-519, (1976).
Mansour et al. "Disruption of the proto-oncogene *int-2* in mouse embryo-derived stem cells: a general strategy for targeting mutations to non-selectable genes," *Nature* 336:348-352, (Nov. 24, 1988).
Mantei et al. "Rabbit β-globin mRNA production in mouse L cells transformed with cloned rabbit β-globin chromosomal DNA," *Nature* 281:40-46, (Sep. 6, 1979).
Marks et al. "By-passing immunization. Human antibodies from V-gene libraries displayed on phage," *J. Mol. Biol.* 222:581-597, (1991).
Mather, "Establishment and characterization of two distinct mouse testicular epithelial cell lines," *Biol. Reprod.* 23:243-252, (1980).
Mather et al., "Culture of testicular cells in hormone-supplemented serum-free medium," *Annals N. Y. Acad. Sci.* 383:44-68, (1982).
Morrison et al. "Chimeric human antibody molecules: mouse antigen-binding domains with human constant region domains," *Proc. Natl. Acad. Sci. USA* 81:6851-6855 (Nov. 1984).
Plückthun, "Antibodies from *Escherichia coli*," Chapter 11 in *Pharmacology of Monoclonal Antibodies*, vol. 113, Rosenburg and Moore eds., Springer-Verlag, New York, pp. 269-315.
Presta, "Antibody engineering," *Curr. Op. Struct. Biol.* 2:593-596, (1992).
Riechmann et al., "Reshaping human antibodies for therapy," *Nature* 332:323-327, (Mar. 24, 1988).
Schleh et al. "Susceptibility of Mouse Minute Virus to Inactivation by Heat in Two Cell Culture Media Types," *Biotechnology Progress* 25(3):854-860, (May 2009).
Urlaub et al., "Isolation of Chinese hamster cell mutants deficient in dihydrofolate reductase activity," *Proc. Natl. Acad. Sci. USA* 77(7):4216-4220, (Jul. 1980).
Vijayasankaran et al. "Animal cell culture media," in *Encyclopedia of Industrial Biotechnology: Bioprocess, Bioseparation, and Cell Technology*, M. C. Flickinger ed., John Wiley & Sons, Inc., pp. 1-15, (2010).
Written Opinion mailed on Aug. 21, 2013, for PCT Application No. PCT/US2013/046756, filed Jun. 20, 2013, 5 pages.
U.S. Appl. No. 14/578,138, filed Dec. 19, 2014 for Shiratori et al.
Fan et al. "Food Microbiology (Chinese Edition)," two pages, (Feb. 28, 2011). (Chinese Only).
Chinese Office Action mailed on Apr. 6, 2016, for Chinese Patent Application No. 201380031879.X, 5 pages. (English Translation.).
Murphy et al. "Effectiveness of Mouse Minute Virus Inactivation by High Temperature Short Time Treatment Technology: A Statistical Assessment," *Biologicals* 39(6):438-443, (Nov. 2011).

\* cited by examiner

Figure 4

Sorted Parameter Estimates

| Term | Estimate | Std Error | t Ratio | Prob>|t| |
|---|---|---|---|---|
| [PO4] mM*[Ca] mM | 28.678271 | 2.413001 | 11.88 | <.0001* |
| [Ca] mM*pH | 28.174984 | 5.263934 | 5.35 | 0.0002* |
| [PO4] mM(0.1,5.9) | 19.481343 | 5.449794 | 3.57 | 0.0038* |
| [PO4] mM*pH | 11.959851 | 6.270648 | 1.91 | 0.0807 |
| [Ca] mM*[Ca] mM | 8.7582743 | 4.753139 | 1.84 | 0.0902 |
| [Ca] mM(0.1,2.9) | 7.0752298 | 4.027581 | 1.76 | 0.1044 |
| pH(6,7.2) | 12.889804 | 15.75033 | 0.82 | 0.4291 |
| [PO4] mM*[PO4] mM | 3.8623212 | 4.870252 | 0.79 | 0.4432 |
| pH*pH | 7.699752 | 12.35742 | 0.62 | 0.5449 |

METHODS FOR VIRAL INACTIVATION AND OTHER ADVENTITIOUS AGENTS

CROSS-REFERENCE TO RELATED APPLICATIONS

This application claims priority to U.S. Provisional Patent Application No. 61/662,349, filed Jun. 20, 2012, the disclosure of which is incorporated by reference herein in its entirety.

FIELD OF INVENTION

The invention provides for methods of viral inactivation using high temperature short time (HTST) treatment and adjustment of various parameters such that generation and depositions of precipitate is reduced and/or minimized.

BACKGROUND OF THE INVENTION

Viruses are potential contaminants in drug manufacturing processes, particularly in cases where biologic drugs are derived from mammalian cell cultures. A source of viral contaminants can be the media used for cell culture or the cell lines producing the biologics of interest. Current approaches to prevent viral contamination of biologic drugs during the manufacturing process includes high temperature short time (HTST) cell media treatment for the inactivation of viruses that may be introduced into cell culture media by raw materials and is amplified during the culturing process (Schleh, M. et al. 2009. *Biotechnol. Prog.* 25(3):854-860 and Kiss, R. 2011. *PDA J Pharm Sci and Tech.* 65:715-729). It has been reported that temperatures in excess of about 85° C. are needed for HTST to be an effective virus inactivation method, with temperatures in excess of about 95° C. needed to inactivate parvovirus, a common cell culture viral contaminant that has been documented as occurring in cell culture processes, and which is resistant to many chemical and physical inactivating agents (Schleh et al.).

Although HTST treatment has proven to be highly effective in the inactivation of viruses, precipitation or formation of precipitates can occur in various cell culture media when subjected to this treatment. This precipitation leads to an accumulation of residue on the surfaces within the HTST system and can contribute to fouling of the equipment such that it can no longer heat up the media to the target temperature for proper inactivation of viral contaminants. Additionally, such precipitation can also foul the filters typically used downstream of the HTST system for the final processing to remove microorgranisms, such as bacteria, from the medium. Such filter fouling can lead to inability to complete the medium processing step prior to the cell culture process. In some instances the precipitate may also impact the performance of the cell culture media and prevent efficient production of biologic drugs from the cultured cell lines. To prevent precipitation, the temperature can be lowered but successful viral inactivation may be negatively affected. Furthermore, precipitate formation during HTST cell media treatment can result in frequent cleaning or repair of equipment used for HTST treatment during the manufacturing process which contributes significantly to the cost of processing. Therefore, there is a need for methods to prevent precipitate formation during HTST treatment without adversely affecting the efficacy of this treatment in the removal or inactivation of viral contaminants.

The invention described herein addresses these needs by providing methods to effectively inactivate viral contaminants in cell culture media using HTST treatment with adjusted processing parameters that results in the reduction or prevention of precipitate formation.

All references cited herein, including patent applications and publications, are incorporated by reference in their entirety.

BRIEF SUMMARY OF THE INVENTION

The invention provides for methods, processes, systems and compositions for inactivating viral contamination and/or other contaminants in cell culture media by using high temperature short time (HTST) treatment in combination with adjustments of various parameters, such as pH and/or calcium and/or phosphate concentration in the media. Furthermore, methods, processes, systems and compositions reducing the fouling of equipment and filters used for HTST treatment are provided as well.

Accordingly, in one aspect, the invention provides for methods for inactivating virus or adventitious agents in cell culture media while the media maintains suitability for cell culture, said method comprising (a) subjecting the cell culture media to high temperature short time (HTST) treatment; and (b) adjusting one or more parameters selected from the group consisting of pH, calcium level and phosphate level.

In other aspects, the invention provides for methods for inactivating virus in cell culture media comprising subjecting the cell culture media to high temperature short time (HTST) treatment wherein the media has a pH of between about pH 5.0 to about pH 6.9 during HTST treatment. In another aspect, the invention provides for methods for inactivating virus in cell culture media comprising subjecting the cell culture media to high temperature short time (HTST) treatment wherein the media has a pH of between about pH 5.0 to about pH 7.2 during HTST treatment. In some embodiments, the media has a pH of between about pH 5.3 to about pH 6.3 during HTST treatment. In other embodiments, the media has a pH of about pH 6.0 during HTST treatment. In any of the embodiments, the HTST treatment comprises raising the temperature of the media to at least about 85 degrees Celsius for a sufficient amount of time to inactivate the virus or potential virus in the media. In some embodiments, the temperature of the media is raised to at least about 93 degrees Celsius for a sufficient amount of time to inactivate the virus or potential virus in the media. In some embodiments, the temperature of the media is raised to at least about 95, 97, 99, 101 or 103 degrees Celsius for a sufficient amount of time to inactivate the virus or potential virus in the media. In some embodiments, the pH of the media is lowered to between about pH 5.0 to about pH 6.9 during HTST treatment prior to polypeptide production phase. In some embodiments, the pH of the media is then brought to between about 6.9-7.2 for the polypeptide production phase.

In another aspect, the invention provides methods for inactivating virus in cell culture media comprising limiting the total amount of phosphate and calcium in the media to less than about 10 mM during HTST treatment. In some embodiments, the total phosphate and calcium concentration in the media is limited to less than about 9, 8, 7, 6, 5, 4, 3, 2, or 1 mM during HTST treatment. In some embodiments, the total amount of phosphate and calcium in the media is limited to less than about 10 mM during HTST treatment prior to polypeptide production phase. In some embodiments, the total amount of phosphate and calcium in the media is then raised to a level sufficient for the polypeptide production during the protein production phase.

In another aspect, the invention provides methods for reducing fouling of equipment used for HTST treatment to inactivate virus, the method comprising subjecting cell culture media used in the equipment to high temperature short time (HTST) treatment wherein the media has a pH of between about pH 5.0 to about pH 6.9 during HTST treatment. In some embodiments, the media has a pH of between about pH 5.3 to about pH 6.3 during HTST treatment. In some embodiments, the media has a pH of about pH 6.0 during HTST treatment. In some embodiments, the fouling comprises precipitation on equipment used for HTST treatment. In any of the embodiments, the HTST treatment comprises raising the temperature of the media to at least about 85 degrees Celsius for a sufficient amount of time to inactivate the virus in the media. In some embodiments, the temperature of the media is raised to at least about 93 degrees Celsius for a sufficient amount of time to inactivate the virus in the media. In some embodiments, the temperature of the media is raised to at least about 95, 97, 99, 101 or 103 degrees Celsius for a sufficient amount of time to inactivate the virus in the media.

In another aspect, the invention provides methods for reducing fouling of equipment used for HTST treatment to inactivate virus, the method comprising limiting the total amount of phosphate and calcium in cell culture media used in the equipment to less than about 10 mM during HTST treatment. In some embodiments, the total phosphate and calcium concentration in the media is limited to less than about 9, 8, 7, 6, 5, 4, 3, 2, or 1 mM during HTST treatment. In some embodiments, the fouling comprises precipitation on equipment used for HTST treatment. In any of the embodiments, the virus is selected from the group consisting of parvoviridae, paramyoxyiridae, orthomyxoviridae, bunyaviridae, rhabdoviridae, reoviridae, togaviridae, caliciviridae, and picornaviridae. In any of the embodiments, the virus is an enveloped virus. In any of the embodiments, the virus is a non-enveloped virus.

BRIEF DESCRIPTION OF THE DRAWINGS

FIG. 4 depicts sorted parameter estimates from Media 4 based media formulations for parameter terms that correlated with a greater level of sand-bath treated sample turbidity.

DETAILED DESCRIPTION

Figure 1:
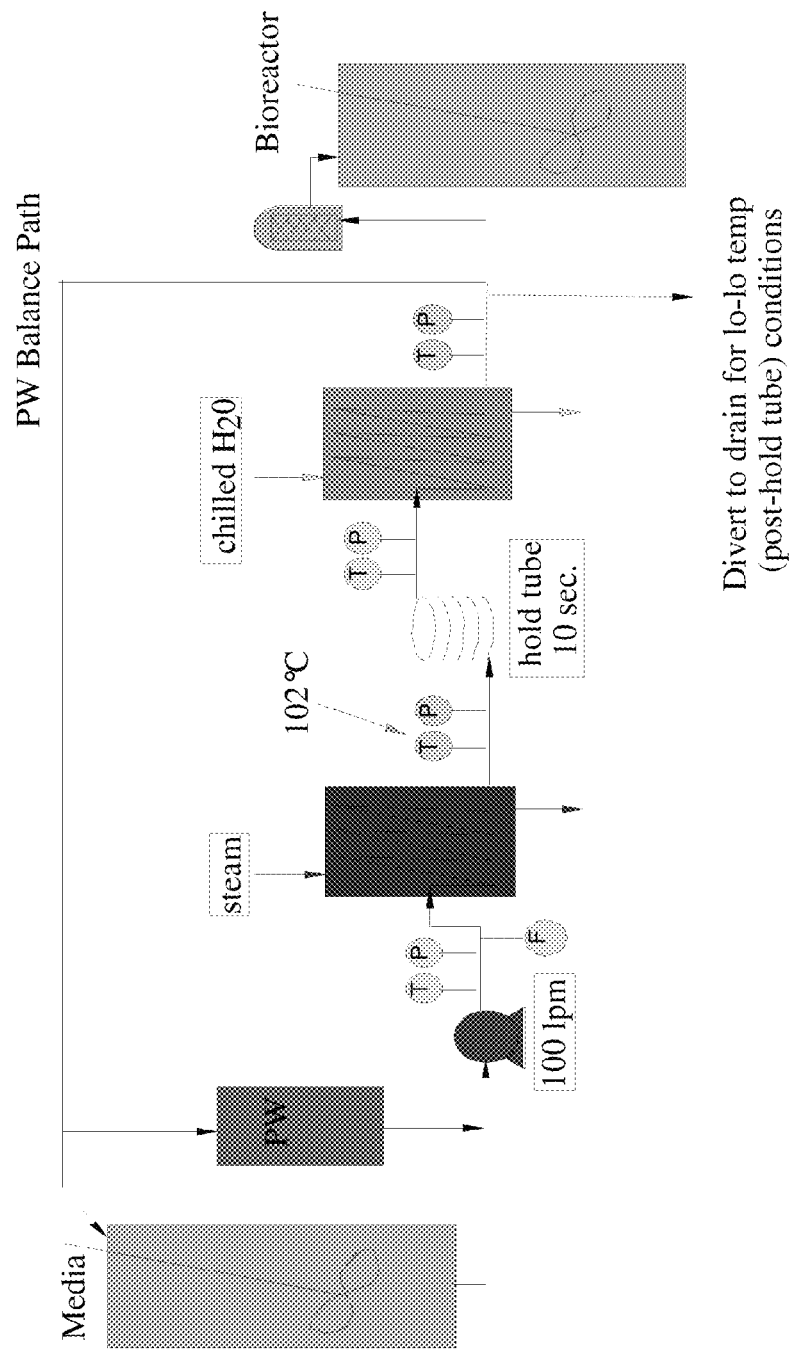
FIG. 1 is a schematic of a representative HTST skid used in manufacturing.

The inventors have made the unexpected discovery that adjusting the pH of the cell culture media, adjusting calcium concentration, adjusting phosphate concentration, adjusting both calcium and phosphate concentration, and/or limiting the total amount of phosphate and calcium in cell culture media, or adjusting a combination of pH, calcium concentration, and phosphate concentration, and subjecting the cell culture media to HTST treatment at a specific temperature range for a sufficient amount of time is effective at inactivating virus (or other infectious and/or adventitious agents) in the media and also reduces fouling of equipment by minimizing or preventing precipitate formation.

The present invention provides methods for reducing precipitate on equipment used for high temperature short time (HTST) treatment to inactivate virus, the method comprising subjecting cell culture media used in the equipment to HTST treatment wherein the media has a pH of between about pH 5.0 to about pH 6.9 or between about pH 5.0 to about pH 7.2 during HTST treatment. In another aspect, the invention provides methods for reducing precipitate on equipment used for high temperature short time (HTST) treatment to inactivate virus, the method comprising subjecting cell culture media used in the equipment to HTST treatment wherein the media has a pH of between about pH 5.0 to about pH 7.2 during HTST treatment. In other aspects, the present invention provides methods for reducing precipitate on equipment used for HTST treatment to inactivate virus, the method comprising limiting the total amount of phosphate and calcium in cell culture media used in the equipment to less than about 10 mM during HTST treatment.

In another aspect, the present invention provides methods for inactivating virus in cell culture media comprising subjecting the cell culture media to HTST treatment wherein the media has a pH of between about pH 5.0 to about pH 6.9 during HTST treatment. In another aspect, the present invention provides methods for inactivating virus in cell culture media comprising subjecting the cell culture media to HTST treatment wherein the media has a pH of between about pH 5.0 to about pH 7.2 during HTST treatment. In still other aspects of the invention, the pH of the media is lowered to between about pH 5.0 to about pH 6.9 during HTST treatment prior to the polypeptide production phase of cell culture. In some aspects, the pH of the media is then brought to between about pH 6.9 to about pH 7.2 for the polypeptide production phase of cell culture. In other aspects, the present invention provides methods for inactivating virus in cell culture media comprising limiting the total amount of phosphate and calcium in cell culture media to less than about 10 mM during HTST treatment.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

"Culturing" a cell refers to contacting a cell with a cell culture medium under conditions suitable to the survival and/or growth of the cell and/or proliferation of the cell.

"Batch culture" refers to a culture in which all components for cell culturing (including the cells and all culture nutrients) are supplied to the culturing vessel at the start of the culturing process.

The phrase "fed batch cell culture," as used herein refers to a batch culture wherein the cells and culture medium are supplied to the culturing vessel initially, and additional culture nutrients are fed, continuously or in discrete increments, to the culture during the culturing process, with or without periodic cell and/or product harvest before termination of culture.

"Perfusion culture" is a culture by which the cells are restrained in the culture by, e.g., filtration, encapsulation, anchoring to microcarriers, etc., and the culture medium is continuously or intermittently introduced and removed from the culturing vessel.

"Culturing vessel" refers to a container used for culturing a cell. The culturing vessel can be of any size so long as it is useful for the culturing of cells.

The terms "medium" and "cell culture medium" refer to a nutrient source used for growing or maintaining cells. As is understood by a person of skill in the art, the nutrient source may contain components required by the cell for growth and/or survival or may contain components that aid in cell growth and/or survival. Vitamins, essential or non-essential amino acids, and trace elements are examples of medium components. It is to be understood that "medium" and "media" are used interchangeably throughout this specification.

A "chemically defined cell culture medium" or "CDM" is a medium with a specified composition that is free of animal-derived or undefined products such as animal serum and peptone. As would be understood by a person of skill in the art, a CDM may be used in a process of polypeptide production whereby a cell is in contact with, and secretes a polypeptide into, the CDM. Thus, it is understood that a composition may contain a CDM and a polypeptide product and that the presence of the polypeptide product does not render the CDM chemically undefined.

A "chemically undefined cell culture medium" refers to a medium whose chemical composition cannot be specified and which may contain one or more animal-derived or undefined products such as animal serum and peptone. As would be understood by a person of skill in the art, a chemically undefined cell culture medium may contain an animal-derived product as a nutrient source.

The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

An "isolated polypeptide" means a polypeptide that has been recovered from a cell or cell culture from which it was expressed.

A "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer.

An "isolated nucleic acid" means and encompasses a non-naturally occurring, recombinant or a naturally occurring sequence outside of or separated from its usual context.

A "purified" polypeptide means that the polypeptide has been increased in purity, such that it exists in a form that is more pure than it exists in its natural environment and/or when initially produced and/or synthesized and/or amplified under laboratory conditions. Purity is a relative term and does not necessarily mean absolute purity.

The term "antibody" or "antibodies" is used in the broadest sense and specifically covers, for example, single monoclonal antibodies (including agonist, antagonist, and neutralizing antibodies), antibody compositions with polyepitopic specificity, polyclonal antibodies, single chain antibodies, multispecific antibodies (e.g., bispecific antibodies), immunoadhesins, and fragments of antibodies as long as they exhibit the desired biological or immunological activity. The term "immunoglobulin" (Ig) is used interchangeable with antibody herein.

"Antibody fragments" comprise a portion of a full length antibody, generally the antigen binding or variable region thereof. Examples of antibody fragments include Fab, Fab', F(ab')2, and Fv fragments; single-chain antibody molecules; diabodies; linear antibodies; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature,* 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222: 581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

"Humanized" antibodies are forms of non-human (e.g., rodent) antibodies that are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321: 522-525 (1986); Riechmann et al., Nature 332:323-329 (1988); and Presta, Curr. Op. Struct. Biol. 2:593-596 (1992).

"Contaminants" refer to materials that are different from the desired polypeptide product. The contaminant includes, without limitation: host cell materials, such as CHOP; leached Protein A; nucleic acid; a variant, fragment, aggregate or derivative of the desired polypeptide; another polypeptide; endotoxin; viral contaminant; cell culture media component, etc.

As used herein, the term "precipitate" refers to formation of a solid or insoluble particles in a solution. Various forms of precipitate occur and exemplary precipitates are described herein. Non-limiting examples include: calcium phosphate precipitation, insoluble whitlockite, oxides, iron phosphate, and iron calcium phosphate precipitates. Calcium phosphate precipitation can be a process wherein calcium and phosphates in solution form insoluble particles, i.e., a precipitate. The insoluble particles may be referred to as calcium phosphates. Calcium phosphates include, without limitation: calcium monobasic phosphate, calcium dibasic phosphate, calcium tribasic phosphate, whitlockite, and hydroxyapatite. The insoluble particles may include additional components, i.e. polypeptides, nucleic acids, lipids, ions, chelators, and metals. Also included within the definition is the growth of such particles by further precipitation or by aggregation, flocculation, and/or rearrangement.

As used herein, the term "fouling" refers to the accumulation and formation of unwanted materials on the surfaces of processing equipment. Fouling may be characterized as a combined, unsteady state, momentum, mass and heat transfer problem with chemical, solubility, corrosion and biological processes also taking place. Fouling may be due to precipitation, i.e., calcium phosphate precipitation.

As used herein, "adventitious agent" encompasses viruses and bacteria (including bacteria that can pass through sterilization grade filters). An "infectious agent" is a type of "adventitious agent."

It is understood that aspects and embodiments of the invention described herein include "comprising," "consisting," and "consisting essentially of" aspects and embodiments.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

III. Cell Culture Media

The methods of inactivating viruses, infectious agents, and/or adventitious agents in cell culture media may be applied to any type of cell culture media where concern about viral contamination, possible viral contamination or contamination by other infectious agents or contamination by adventitious agents exists. It is understood that the invention contemplates compositions and methods is applicable to cell cultures and cell culture media where there is possible viral contamination as well as actual viral contamination.

The methods of virus inactivation, reducing precipitate formation and reducing fouling of equipment used for HTST treatment can be used to produce a composition of cell culture media where viruses, adventitious agents, and other infectious agents have been inactivated. As such, any compositions of cell culture media and its intermediates as it is going through the system of viral inactivation, adventitious agents inactivation, and/or infectious agent inactivation are contemplated and are detailed herein. Adjustment of specific cell culture media parameters (pH, calcium levels and phosphate levels) has been identified as capable of reducing or preventing formation of precipitates in the media after being subjected to HTST treatment at temperatures effective for inactivating viral contaminants and other contaminants present in the media.

Independent adjustments of cell culture media parameters such as pH, calcium concentrations or amounts, and phosphate concentrations or amounts (and any combinations thereof) can be used with HTST treatment to reduce precipitates (e.g. complex comprising calcium and phosphate), to reduce fouling of HTST equipment, to reduce filter fouling, all while maintaining suitability for cell culture. Cell culture media which maintains suitability for cell culture allows for cells to propagate, grow, survive, produce any polypeptide, protein or compound, secrete any such products into the media, and any other features that one of skill in the art would understand to be included for suitability purposes of cell culture.

The independent adjustments of the cell culture parameters described herein is applicable to any cell culture process and can be beneficial for the production of polypeptides and/or proteins but also for the generation of other products, such as cells, the media and other components in the media. Adjustment of these cell culture media parameters for the reduction or prevention of precipitates in cell culture media is beneficial for production of biologic drugs such as a polypeptide drug product. Use of the cell culture media with these adjusted parameters or components is effective for removing viral contaminants from a biologic drug product as well as reduction or prevention of precipitates that can impact the performance of the cell culture media, prevent efficient production of biologic drugs from the cultured cell lines and contribute to fouling of HTST equipment. Any medium detailed herein may be employed at any stage of cell growth, maintenance and biologic drug production and may be used in the basal medium and/or in the feed medium. Media as described herein in one variation result in acceptable turbidity or precipitate levels of a composition comprising the biologic drug isolated from cell culture grown in the media subjected to HTST treatment.

A cell culture medium comprising one or more of the following components is provided: (a) calcium and (b) phosphate. In some variations, a cell culture medium comprises components (a) or (b), or components (a) and (b). In other variations, a cell culture medium does not comprise components (a) and (b). In some aspects, the cell culture medium is a chemically defined cell culture medium. In other aspects, the cell culture medium is a chemically undefined cell culture medium. In any of the aspects, the cell culture media is used for inactivating virus during HTST treatment. In any of the aspects, the cell culture media is treated by HTST to inactivate virus potentially present from the raw materials and handling used to prepare the media.

Media components may be added to a composition in forms that are known in the art. For example, calcium may be provided as, but not limited to, calcium chloride, calcium chloride dehydrate, calcium carbonate, calcium phosphate, calcium phosphate tribasic, calcium L-lactate hydrate, calcium folinate, and calcium nitrate tetrahydrate. For example, phosphate may be provided as, but not limited to, sodium phosphate, monosodium phosphate, disodium phosphate, potassium phosphate monobasic, phosphate buffered saline, calcium phosphate, and calcium phosphate dibasic.

The ratio of phosphate and calcium can be adjusted for the HTST treatment such that complexes comprising calcium and phosphate (e.g., calcium phosphate ($CaPO_4$) complexes) do not form. In one variation, the total amount of phosphate and calcium is adjusted or limited such that complexes comprising calcium and phosphate (e.g., calcium phosphate ($CaPO_4$) complexes) do not form. In another variation, the total amount of phosphate and calcium is limited such that the formation of $CaPO_4$ complexes enables successful HTST operation (e.g. no fouling of HTST and filtration equipment). Detection methods for problematic conditions typically involve indirect measurements for precipitation including turbidity, operational observations of HTST and filtration equipment, and visual observations on HTST and filtration equipment (e.g. by use of a boroscope). In one aspect, the media is a cell culture medium comprising limiting the total amount of phosphate and calcium to less than about 10 mM. In another variation, the total phosphate and calcium is at a concentration in the media to less than about 9, 8, 7, 6, 5, 4, 3, 2, or 1 mM. In another variation, the total phosphate and calcium is at a concentration in the media from about 1 mM to about 9 mM; from about 2 mM to about 8 mM; from about 3 mM to about 7 mM; from about 4 mM to about 6 mM; from about 1 mM to about 8 mM; from about 1 mM to about 7 mM; from about 1 mM to about 6 mM; from about 1 mM to about 5 mM; from about 1 mM to about 4 mM; from about 1 mM to about 3 mM; from about 1 mM to about 2 mM; from about 2 mM to about 9 mM; from about 3 mM to about 9 mM; from about 4 mM to about 9 mM; from about 5 mM to about 9 mM; from about 6 mM to about 9 mM; from about 7 mM to about 9 mM; from about 8 mM to about 9 mM; about any of 9 or 8 or 7 or 6 or 5 or 4 or 3 or 2 or 1 mM; at least about any of 1 or 2 or 3 or 4 or 5 or 6 or 7 or 8 and no more than about 9 mM. In a variation, the total phosphate and calcium is at a concentration in the media from about 1 mM to about 9 mM; from about 2 mM to about 8 mM; from about 3 mM to about 7 mM; from about 4 mM to about 6 mM; from about 1 mM to about 8 mM; from about 1 mM to about 7 mM; from about 1 mM to about 6 mM; from about 1 mM to about 5 mM; from about 1 mM to about 4 mM; from about 1 mM to about 3 mM; from about 1 mM to about 2 mM; from about 2 mM to about 9 mM; from about 3 mM to about 9 mM; from about 4 mM to about 9 mM; from about 5 mM to about 9 mM; from about 6 mM to about 9 mM; from about 7 mM to about 9 mM; from about 8 mM to about 9 mM; about any of 9 or 8 or 7 or 6 or 5 or 4 or 3 or 2 or 1 mM; at least about any of 1 or 2 or 3 or 4 or 5 or 6 or 7 or 8 and no more than about 9 mM during HTST treatment prior to the polypeptide production phase of cell culture. In any of the aspects of the invention, the total amount of calcium and phosphate in the media is limited to less than about 10 mM during HTST treatment prior to the polypeptide production phase of cell culture. In further aspects of the invention, the total amount of calcium and phosphate in the media is then raised to a level sufficient for polypeptide production during the polypeptide production phase of cell culture. In some aspects, the cell culture medium is free of calcium and phosphate.

The calcium level in cell culture media can be adjusted when the media comprises phosphate. The adjustments can be increase or reduction in the calcium level. In some embodiments, the calcium level is reduced (including removal of the calcium). In other embodiments, the calcium level is reduced such that formation of complexes comprised of calcium and phosphate is suppressed. In other embodiments, calcium is removed from the media prior to HTST treatment. In any of these embodiments, the pH is adjusted such that formation of complexes comprised of calcium and phosphate is suppressed (e.g, reduced in amount as compared to the complexes that would form if these adjustments were not made). In other embodiments, the calcium level can be further adjusted following HTST treatment to a suitable level for cell culture. The timing between the HTST treatment and adjustment of calcium levels following the HTST to a suitable level for cell culture can be varied. Time elapse of seconds, minutes, days, weeks, months or years is contemplated within the scope of the invention.

In another variation, the media is a cell culture medium comprising limiting the total amount of calcium to less than about 10 mM. In another variation, the total calcium is at a concentration in the media to less than about 9, 8, 7, 6, 5, 4, 3, 2, or 1 mM. In another variation, the total calcium is at a concentration in the media from about 1 mM to about 9 mM; from about 2 mM to about 8 mM; from about 3 mM to about 7 mM; from about 4 mM to about 6 mM; from about 1 mM to about 8 mM; from about 1 mM to about 7 mM; from about 1 mM to about 6 mM; from about 1 mM to about 5 mM; from about 1 mM to about 4 mM; from about 1 mM to about 3 mM; from about 1 mM to about 2 mM; from about 2 mM to about 9 mM; from about 3 mM to about 9 mM; from about 4 mM to about 9 mM; from about 5 mM to about 9 mM; from about 6 mM to about 9 mM; from about 7 mM to about 9 mM; from about 8 mM to about 9 mM; about any of 9 or 8 or 7 or 6 or 5 or 4 or 3 or 2 or 1 mM; at least about any of 1 or 2 or 3 or 4 or 5 or 6 or 7 or 8 and no more than about 9 mM. In another variation, the total calcium is at a concentration in the media from about 1 mM to about 9 mM; from about 2 mM to about 8 mM; from about 3 mM to about 7 mM; from about 4 mM to about 6 mM; from about 1 mM to about 8 mM; from about 1 mM to about 7 mM; from about 1 mM to about 6 mM; from about 1 mM to about 5 mM; from about 1 mM to about 4 mM; from about 1 mM to about 3 mM; from about 1 mM to about 2 mM; from about 2 mM to about 9 mM; from about 3 mM to about 9 mM; from about 4 mM to about 9 mM; from about 5 mM to about 9 mM; from about 6 mM to about 9 mM; from about 7 mM to about 9 mM; from about 8 mM to about 9 mM; about any of 9 or 8 or 7 or 6 or 5 or 4 or 3 or 2 or 1 mM; at least about any of 1 or 2 or 3 or 4 or 5 or 6 or 7 or 8 and no more than about 9 mM during HTST treatment prior to the polypeptide production phase of cell culture. In any of the aspects of the invention, the total amount of calcium in the media is limited to less than about 10 mM during HTST treatment prior to the polypeptide production phase of cell culture. In further aspects of the invention, the total amount of calcium in the media is then raised to a level sufficient for polypeptide production during the polypeptide production phase of cell culture. In some aspects the cell culture medium is free of phosphate.

In another aspect, the phosphate level can be adjusted when the media comprises calcium. The adjustments can be increase or reduction in the phosphate level. In some embodiments, the phosphate level is reduced. In some embodiments, the phosphate level is reduced such that formation of complexes comprised of calcium and phosphate is suppressed. In some embodiments, phosphate is removed from the media prior to HTST treatment. In some embodiments, the pH is adjusted such that formation of complexes comprised of calcium and phosphate is suppressed. In some embodiments, the phosphate level is further adjusted following HTST treatment to a suitable level for cell culture. The timing between the HTST treatment and adjustment of phosphate levels following the HTST to a suitable level for cell culture can be varied. Time elapse of seconds, minutes, days, weeks, months or years is contemplated within the scope of the invention.

In another variation, the media is a cell culture medium comprising limiting the total amount of phosphate to less than about 10 mM. In another variation, the total phosphate is at a concentration in the media to less than about 9, 8, 7, 6, 5, 4, 3, 2, or 1 mM. In another variation, the total phosphate is at a concentration in the media from about 1 mM to about 9 mM; from about 2 mM to about 8 mM; from about 3 mM to about 7 mM; from about 4 mM to about 6 mM; from about 1 mM to about 8 mM; from about 1 mM to about 7 mM; from about 1 mM to about 6 mM; from about 1 mM to about 5 mM; from about 1 mM to about 4 mM; from about 1 mM to about 3 mM; from about 1 mM to about 2 mM; from about 2 mM to about 9 mM; from about 3 mM to about 9 mM; from about 4 mM to about 9 mM; from about 5 mM to about 9 mM; from about 6 mM to about 9 mM; from about 7 mM to about 9 mM; from about 8 mM to about 9 mM; about any of 9 or 8 or 7 or 6 or 5 or 4 or 3 or 2 or 1 mM; at least about any of 1 or 2 or 3 or 4 or 5 or 6 or 7 or 8 and no more than about 9 mM. In another variation, the total phosphate is at a concentration in the media from about 1 mM to about 9 mM; from about 2 mM to about 8 mM; from about 3 mM to about 7 mM; from about 4 mM to about 6 mM; from about 1 mM to about 8 mM; from about 1 mM to about 7 mM; from about 1 mM to about 6 mM; from about 1 mM to about 5 mM; from about 1 mM to about 4 mM; from about 1 mM to about 3 mM; from about 1 mM to about 2 mM; from about 2 mM to about 9 mM; from about 3 mM to about 9 mM; from about 4 mM to about 9 mM; from about 5 mM to about 9 mM; from about 6 mM to about 9 mM; from about 7 mM to about 9 mM; from about 8 mM to about 9 mM; about any of 9 or 8 or 7 or 6 or 5 or 4 or 3 or 2 or 1 mM; at least about any of 1 or 2 or 3 or 4 or 5 or 6 or 7 or 8 and no more than about 9 mM during the polypeptide production phase of cell culture. In any of the aspects of the invention, the total amount of phosphate in the media is limited to less than about 10 mM during HTST treatment prior to the polypeptide production phase of cell culture. In further aspects of the invention, the total amount of phosphate in the media is then raised to a level sufficient for polypeptide production during the polypeptide production phase of cell culture. In some aspects the cell culture medium is free of calcium.

In one variation, a cell culture medium comprises 1 or 2 or each of components (a) and (b) in the concentrations recited herein comprising limiting total amount of (a) or (b), or (a) and (b) to less than about 10 mM. It is understood that a cell culture medium may contain a combination of components (a) and (b) in any of the concentration ranges provided herein the same as if each and every concentration were specifically and individually listed. For example, it is understood that the medium in one variation comprises components (a) and (b), wherein calcium is about 0.5 mM and phosphate is from about 2.5 mM. In some aspects, the cell culture medium is a chemically defined cell culture medium. In other aspects, the cell culture medium is a chemically undefined cell culture medium. In any of the aspects, the cell culture media is used for inactivating virus during HTST treatment. In any aspect, the media is free of calcium during HTST treatment. In a further aspect, calcium is added to the cell culture media after HTST treatment. In any aspect, the media is free of phosphate during HTST treatment. In a further aspect, phosphate is added to the cell culture media after HTST treatment.

Figure 5:
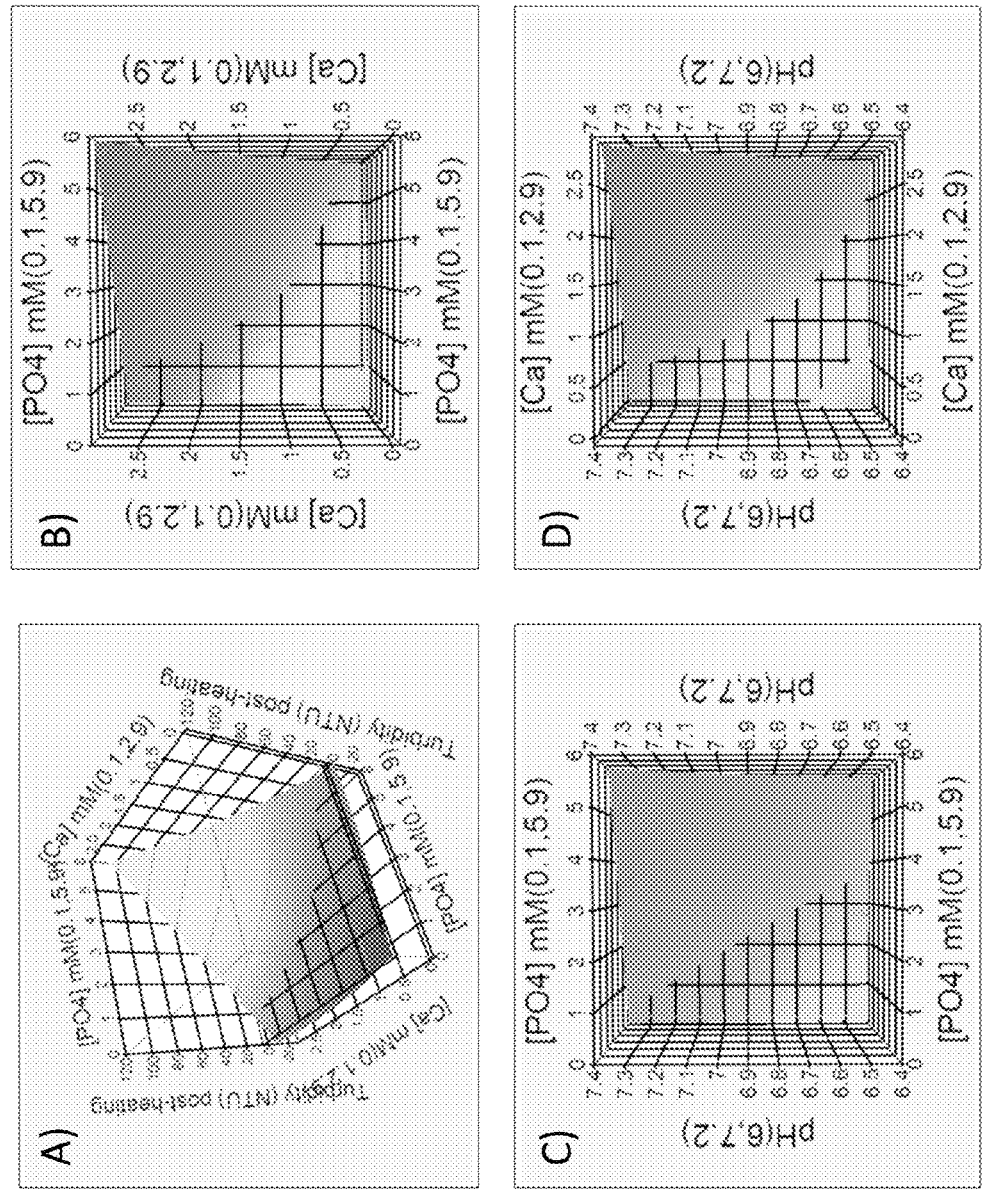
FIG. 5 is a series of graphs depicting precipitation response surface as measured by turbidity (NTU) from 3 perspectives for Media 4 based formulations with varied calcium, phosphate, and pH levels during sand-bath heat treatment. Portions of each perspective-plane where the grid is visible show a region where turbidity was lower than 5 NTU, correlated with no visible precipitation in media samples tested and represented a safe-operating regime. A) Side view of graph showing turbidity measurements in media with varying concentrations of phosphate and calcium. Top view of graph showing turbidity measurements in media with B) varying concentrations of phosphate and calcium, C) varying concentrations of phosphate and pH levels, and D) varying concentrations of calcium and pH levels.

In one variation, the media is a cell culture medium comprising a phosphate concentration from about 0 mM to about 1 mM, and a calcium concentration from about 0.5 mM to about 3 mM. In another variation, the phosphate concentration is from about 1 mM to about 1.25 mM, and the calcium concentration is from about 0 mM to about 2.5 mM. In a further variation, the phosphate concentration is from about 1.25 mM to about 1.5 mM, and the calcium concentration is from about 0 mM to about 2.25 mM. In yet another variation, the phosphate concentration is from about 1.5 mM to about 1.75 mM, and the calcium concentration is from about 0 mM to about 2 mM. In one variation, the phosphate concentration is from about 1.75 mM to about 2 mM, and the calcium concentration is from about 0 mM to about 1.75 mM. In another variation, the phosphate concentration is from about 2 mM to about 2.25 mM, and the calcium concentration is from about 0 mM to about 1.5 mM. In a further variation, the phosphate concentration is from about 2 mM to about 2.25 mM, and the calcium concentration is from about 0 mM to about 1.5 mM. In another variation, the phosphate concentration is from about 2.25 mM to about 2.5 mM, and the calcium concentration is from about 0 mM to about 1.25 mM. In still another variation, the phosphate concentration is from about 2.5 mM to about 2.75 mM, and the calcium concentration is from about 0 mM to about 1.15 mM. In another variation, the phosphate concentration is from about 2.75 mM to about 3 mM, and the calcium concentration is from about 0 mM to about 1 mM. In a further variation, the phosphate concentration is from about 3 mM to about 3.5 mM, and the calcium concentration is from about 0 mM to about 0.8 mM. In yet a further variation, the phosphate concentration is from about 3.5 mM to about 4.5 mM, and the calcium concentration is from about 0 mM to about 0.6 mM. In one variation, the phosphate concentration is from about 4.5 mM to about 5 mM, and the calcium concentration is from about 0 mM to about 0.5 mM. In another variation, the phosphate concentration is from about 5 mM to about 5.5 mM, and the calcium concentration is from about 0 mM to about 0.25 mM. In a further variation, the phosphate concentration is from about 5.5 mM to about 6 mM, and the calcium concentration is from about 0 mM to about 0.1 mM. In another aspect, the parameters of pH, calcium and phosphate can be independently adjusted as shown in exemplary FIG. 5 (such as FIG. 5B, FIG. 5C, and FIG. 5D) such that the turbidity (as an indirect measure of calcium phosphate based precipitation) stays in the grid area (where the grid area represents turbidity values at or below the gross-failure turbidity threshold of 5 NTU in this example) and avoid the precipitation ranges that is shown in the non-grid areas (where non-grid areas represent the turbidity response above the gross-failure turbidity threshold of 5 NTU). The response surface depicted in FIG. 5 shows the multi-factor effects of pH, calcium concentrations, and phosphate concentrations on turbidity (as an indirect measure of calcium phosphate based precipitation). Therefore, the response surface demonstrates how the factors can be adjusted in combination and not just as one factor at a time to find acceptable HTST treatment operating set points for pH in combination with acceptable calcium and phosphate concentrations in the media to be processed.

Another independent parameter (in addition to calcium and phosphate as other independent parameters) that can be adjusted is pH. As such, the pH can be adjusted when the media comprises calcium and phosphate. In some embodiments, the pH is adjusted in preparing the media prior to HTST treatment to a suitable low level. In some embodiments, the pH is adjusted by lowering to a suitable level. In some embodiments, the pH is adjusted to less than about 7.2. In some embodiments, the pH is adjusted to about 5.0-7.2. In some embodiments, the pH is further adjusted following HTST treatment to a suitable level for cell culture. In some embodiments, the pH is adjusted to about 6.9-7.2. The timing between the HTST treatment and adjustment of pH levels following the HTST to a suitable level for cell culture can be varied. Time elapse of seconds, minutes, days, weeks, months or years is contemplated within the scope of the invention.

In other aspects, a cell culture medium comprising a pH of between about pH 5.0 to about pH 7.2 is provided. In one aspect, a cell culture medium comprising a pH of between about pH 5.0 to about pH 6.9 is provided. In some aspects, the cell culture medium is a chemically defined cell culture medium. In other aspects, the cell culture medium is a chemically undefined cell culture medium. In any of the aspects, the cell culture media is used for inactivating virus during HTST treatment. In any of the aspects, the pH of the media is between about pH 5.0 to about pH 7.2 during HTST treatment. This can be prior to the polypeptide production phase of cell culture. Optionally, one of skill in the art can adjust the pH of the media after HTST treatment such that the media is at pH which is suitable for cell culture processes. In any of the aspects, the pH of the media is lowered to between about pH 5.0 to about pH 6.9 during HTST treatment prior to the polypeptide production phase of cell culture. In further aspects, the pH of the media is then brought to between about pH 6.9 to about pH 7.2 for the polypeptide production phase of cell culture. In one aspect, the pH of the media is then brought to between about pH 6.9 to about pH 7.2 after HTST treatment for the polypeptide production phase of cell culture.

In one variation, the media is a cell culture medium comprising a pH of between about pH 5.0 to about pH 7.2. In another variation, the media is a cell culture medium comprising a pH of between about pH 5.0 to about pH 6.9. In another variation, the pH of the media is at a pH from about 5.0 to about 7.2; from about 5.0 to about 6.9; from about 5.2 to about 6.7; from about 5.4 to about 6.5; from about 5.6 to about 6.3; from about 5.8 to about 6.1; from about 5.9 to about 6.0; from about 5.0 to about 6.7; from about 5.0 to about 6.5; from about 5.0 to about 6.3; from about 5.0 to about 6.1; from about 5.0 to about 5.9; from about 5.0 to about 5.7; from about 5.0 to about 5.5; from about 5.0 to about 5.3; from about 5.0 to about 5.1; from about 5.2 to about 6.9; from about 5.4 to about 6.9; from about 5.6 to about 6.9; from about 5.8 to about 6.9; from about 6.0 to about 6.9; from about 6.0 to about 6.9; from about 6.2 to about 6.9; from about 6.4 to about 6.9; from about 6.6 to about 6.9; about any of 5.0 or 5.2 or 5.4 or 5.6 or 5.8 or 6.0 or 6.2 or 6.4 or 6.6 or 6.8 or 6.9; at least about any of 5.0 or 5.2 or 5.4 or 5.6 or 5.8 or 6.0 or 6.2 or 6.4 or 6.6 or 6.8 and no more than about 6.9. In one variation, the media is a cell culture medium comprising a pH of between about pH 5.0 to about pH 7.2. In another variation, the pH of the media is at a pH from about 5.0 to about 6.9; from about 5.2 to about 6.7; from about 5.4 to about 6.5; from about 5.6 to about 6.3; from about 5.8 to about 6.1; from about 5.9 to about 6.0; from about 5.0 to about 6.7; from about 5.0 to about 6.5; from about 5.0 to about 6.3; from about 5.0 to about 6.1; from about 5.0 to about 5.9; from about 5.0 to about 5.7; from about 5.0 to about 5.5; from about 5.0 to about 5.3; from about 5.0 to about 5.1; from about 5.2 to about 6.9; from about 5.4 to about 6.9; from about 5.6 to about 6.9; from about 5.8 to about 6.9; from about 6.0 to about 6.9; from about 6.0 to about 6.9; from about 6.2 to about 6.9; from about 6.4 to about 6.9; from about 6.6 to about 6.9; about any of 5.0 or 5.2 or 5.4 or 5.6 or 5.8 or 6.0 or 6.2 or 6.4 or 6.6 or 6.8 or 6.9; at least about any of 5.0 or 5.2 or 5.4 or 5.6 or 5.8 or 6.0 or 6.2 or 6.4 or 6.6 or 6.8 and no more than about 6.9 during HTST treatment prior to the polypeptide production phase of cell culture. In any of the aspects, the pH of the media is between about pH 5.0 to about pH 7.2 during HTST treatment. This can be prior to the polypeptide production phase of cell culture. The media can be adjusted to a suitable pH for cell culture processes as needed after the HTST treatment. In any of the aspects, the pH of the media is lowered to between about pH 5.0 to about pH 6.9 during HTST treatment prior to the polypeptide production phase of cell culture. In any of the aspects, the pH of the media is between about pH 5.0 to about pH 6.9 during HTST treatment prior to the polypeptide production phase of cell culture.

In one variation, the media is a cell culture medium comprising a pH of between about pH 6.9 to about pH 7.2. In another variation, the pH of the media is at a pH from about 6.9 to about 7.2; from about 7.0 to about 7.1; from about 6.9 to about 7.1; from about 6.9 to about 7.0; from about 7.0 to about 7.2; from about 7.1 to about 7.2; about any of 6.9 or 7.0 or 7.1 or 7.2; at least about any of 6.9 or 7.0 or 7.1 and no more than about 7.2. In one variation, the media is a cell culture medium comprising a pH of between about pH 6.9 to about pH 7.2. In another variation, the pH of the media is at a pH from about 6.9 to about 7.2; from about 7.0 to about 7.1; from about 6.9 to about 7.1; from about 6.9 to about 7.0; from about 7.0 to about 7.2; from about 7.1 to about 7.2; about any of 6.9 or 7.0 or 7.1 or 7.2; at least about any of 6.9 or 7.0 or 7.1 and no more than about 7.2 for the polypeptide production phase of cell culture. In any of the aspects, the pH of the media is brought to between about pH 6.9 to about pH 7.2 for the polypeptide production phase of cell culture. In any of the aspects, the pH of the media is brought to between about pH 6.9 to about pH 7.2 after HTST treatment for the polypeptide production phase of cell culture. In any of the aspects, the pH of the media is between about pH 6.9 to about pH 7.2 after HTST treatment for the polypeptide production phase of cell culture.

In one variation, the media is a cell culture media comprising a pH of between about pH 5.0 to about pH 6.9 and a total amount of phosphate and calcium less than about 10 mM. In one variation, the media is a cell culture media comprising a pH of between about pH 5.0 to about pH 6.9 and a total amount of phosphate and calcium less than about 10 mM during HTST treatment. In any variation, the pH and amount of calcium and phosphate is any amount detailed herein. In any aspect, the media is free of calcium during HTST treatment. In a further aspect, calcium is added to the cell culture media after HTST treatment. In any aspect, the media is free of phosphate during HTST treatment. In a further aspect, phosphate is added to the cell culture media after HTST treatment. In a further aspect, the pH of the media is brought to between about pH 6.9 to about pH 7.2 for the polypeptide production phase of cell culture. In any of the aspects, the pH of the media is brought to between about pH 6.9 to about pH 7.2 after HTST treatment for the polypeptide production phase of cell culture.

In one variation, the media is a cell culture medium comprising a phosphate concentration from about 0 mM to about 0.5 mM, and a pH from about 6.4 to about 7.4. In another variation, the phosphate concentration is from about 0.5 mM to about 0.75 mM, and the pH is from about 6.4 to about 7.35. In a further variation, the phosphate concentration is from about 0.75 mM to about 1 mM, and the pH is from about 6.4 to about 7.25. In yet another variation, the phosphate concentration is from about 1 mM to about 1.25 mM, and the pH is from about 6.4 to about 7.2. In one variation, the phosphate concentration is from about 1.25 mM to about 1.5 mM, and the pH is from about 6.4 to about 7.1. In another variation, the phosphate concentration is from about 1.5 mM to about 1.75 mM, and the pH is from about 6.4 to about 7.05. In a further variation, the phosphate concentration is from about 1.75 mM to about 2 mM, and the pH is from about 6.4 to about 7. In yet another variation, the phosphate concentration is from about 2 mM to about 2.25 mM, and the pH is from about 6.4 to about 6.9. In one variation, the phosphate concentration is from about 2.25 mM to about 2.5 mM, and the pH is from about 6.4 to about 6.85. In another variation, the phosphate concentration is from about 2.5 mM to about 2.75 mM, and the pH is from about 6.4 to about 6.75. In a further variation, the phosphate concentration is from about 2.75 mM to about 3 mM, and the pH is from about 6.4 to about 6.7. In still a further variation, the phosphate concentration is from about 3 mM to about 3.25 mM, and the pH is from about 6.4 to about 6.6. In one variation, the phosphate concentration is from about 3.25 mM to about 3.5 mM, and the pH is from about 6.4 to about 6.5. In another variation, the phosphate concentration is from about 3.5 mM to about 3.75 mM, and the pH is from about 6.4 to about 6.45.

In one variation, the calcium concentration is from about 0 mM to about 1 mM, and the pH is from about 6.65 to about 7.4. In another variation, the calcium concentration is from about 0.1 mM to about 0.25 mM, and the pH is from about 6.55 to about 7.4. In a further variation, the calcium concentration is from about 0.25 mM to about 0.5 mM, and the pH is from about 6.5 to about 7.4. In yet another variation, the calcium concentration is from about 0.5 mM to about 0.6 mM, and the pH is from about 6.5 to about 7.2. In one variation, the calcium concentration is from about 0.6 mM to about 0.75 mM, and the pH is from about 6.5 to about 7. In another variation, the calcium concentration is from about 0.75 mM to about 1 mM, and the pH is from about 6.4 to about 6.9. In a further variation, the calcium concentration is from about 1 mM to about 1.1 mM, and the pH is from about 6.4 to about 6.8. In yet a further variation, the calcium concentration is from about 1.1 mM to about 1.25 mM, and the pH is from about 6.4 to about 6.7. In one variation, the calcium concentration is from about 1.25 mM to about 1.5 mM, and the pH is from about 6.4 to about 6.65. In another variation, the calcium concentration is from about 1.5 mM to about 1.75 mM, and the pH is from about 6.4 to about 6.55. In a further variation, the calcium concentration is from about 1.75 mM to about 2 mM, and the pH is from about 6.4 to about 6.5. In one variation, the calcium concentration is from about 2 mM to about 2.25 mM, and the pH is from about 6.4 to about 6.45. In another variation, the calcium concentration is from about 2.25 mM to about 2.5 mM, and the pH is from about 6.4 to about 6.43. In a further variation, the calcium concentration is from about 2.5 mM to about 2.6 mM, and the pH is from about 6.4 to about 6.41.

Individual media components may be present in amounts that result in one or more advantageous properties such as viral inactivation, reduction of precipitate formation and reducing fouling of equipment used for HTST treatment. In one variation, a cell culture medium as provided herein contains media parameters as described in Table 1. It is understood that a medium composition may comprise any one or more of the medium components of Table 1 (e.g., any one or more of components (a)-(c), such as a medium composition comprising each of components (a), (b), and (c), or a medium composition comprising each of components (a), (b), and (d), or a medium composition comprising components (a) and (b), or a medium composition comprising each of components (a) and (c), or a medium composition comprising each of components (b) and (c), or a medium composition comprising each of components (a) and (d), or a medium composition comprising each of components (b) and (d) in any of the amounts listed in Table 1, the same as if each and every combination of components and amounts were specifically and individually listed. In some aspects, the cell culture medium is a chemically defined cell culture medium. In other aspects, the cell culture medium is a chemically undefined cell culture medium. In any of the aspects, the cell culture media is used for inactivating virus during HTST treatment. In any aspect, the media is free of calcium during HTST treatment. In a further aspect, calcium is added to the cell culture media after HTST treatment. In any aspect, the media is free of phosphate during HTST treatment. In a further aspect, phosphate is added to the cell culture media after HTST treatment. In a further aspect, the pH of the media is brought to between about pH 6.9 to about pH 7.2 for the polypeptide production phase of cell culture. In any of the aspects, the pH of the media is brought to between about pH 6.9 to about pH 7.2 after HTST treatment for the polypeptide production phase of cell culture.

TABLE 1

Exemplary Levels of Media Components or Parameters

| Media Component or Parameter | Level of Component or Parameter in Medium |
|---|---|
| (a) Calcium | from about 1 mM to about 9 mM; from about 2 mM to about 8 mM; from about 3 mM to about 7 mM; from about 4 mM to about 6 mM; from about 1 mM to about 8 mM; from about 1 mM to about 7 mM; from about 1 mM to about 6 mM; from about 1 mM to about 5 mM; from about 1 mM to about 4 mM; from about 1 mM to about 3 mM; from about 1 mM to about 2 mM; from about 2 mM to about 9 mM; from about 3 mM to about 9 mM; from about 4 mM to about 9 mM; from about 5 mM to about 9 mM; from about 6 mM to about 9 mM; from about 7 mM to about 9 mM; from about 8 mM to about 9 mM; about any of 9 or 8 or 7 or 6 or 5 or 4 or 3 or 2 or 1 mM; at least about any of 1 or 2 or 3 or 4 or 5 or 6 or 7 or 8 and no more than about 9 mM. |
| (b) Phosphate | from about 1 mM to about 9 mM; from about 2 mM to about 8 mM; |

TABLE 1-continued

Exemplary Levels of Media Components or Parameters

| Media Component or Parameter | Level of Component or Parameter in Medium |
|---|---|
| | from about 3 mM to about 7 mM; from about 4 mM to about 6 mM; from about 1 mM to about 8 mM; from about 1 mM to about 7 mM; from about 1 mM to about 6 mM; from about 1 mM to about 5 mM; from about 1 mM to about 4 mM; from about 1 mM to about 3 mM; from about 1 mM to about 2 mM; from about 2 mM to about 9 mM; from about 3 mM to about 9 mM; from about 4 mM to about 9 mM; from about 5 mM to about 9 mM; from about 6 mM to about 9 mM; from about 7 mM to about 9 mM; from about 8 mM to about 9 mM; about any of 9 or 8 or 7 or 6 or 5 or 4 or 3 or 2 or 1 mM; at least about any of 1 or 2 or 3 or 4 or 5 or 6 or 7 or 8 and no more than about 9 mM. |
| (c) pH (prior to polypeptide production phase) | from about 5.0 to about 6.9; from about 5.2 to about 6.7; from about 5.4 to about 6.5; from about 5.6 to about 6.3; from about 5.8 to about 6.1; from about 5.9 to about 6.0; from about 5.0 to about 6.7; from about 5.0 to about 6.5; from about 5.0 to about 6.3; from about 5.0 to about 6.1; from about 5.0 to about 5.9; from about 5.0 to about 5.7; from about 5.0 to about 5.5; from about 5.0 to about 5.3; from about 5.0 to about 5.1; from about 5.2 to about 6.9; from about 5.4 to about 6.9; from about 5.6 to about 6.9; from about 5.8 to about 6.9; from about 6.0 to about 6.9; from about 6.0 to about 6.9; from about 6.0 to about 6.2; from about 6.4 to about 6.9; from about 6.6 to about 6.9; about any of 5.0 or 5.2 or 5.4 or 5.6 or 5.8 or 6.0 or 6.2 or 6.4 or 6.6 or 6.8 or 6.9; at least about any of 5.0 or 5.2 or 5.4 or 5.6 or 5.8 or 6.0 or 6.2 or 6.4 or 6.6 or 6.8 and no more than about 6.9; from about 5.0 to about 7.2; from about 5.2 to about 6.9; from about 5.4 to about 6.6; from about 5.6 to about 6.3; from about 5.8 to about 6.0; from about 5.2 to about 7.2; from about 5.4 to about 7.2; from about 5.6 to about 7.2; from about 5.8 to about 7.2; from about 6.0 to about 7.2; from about 6.0 to about 7.2; from about 6.2 to about 7.2; from about 6.4 to about 7.2; from about 6.6 to about 7.2; about any of 5.0 or 5.2 or 5.4 or 5.6 or 5.8 or 6.0 or 6.2 or 6.4 or 6.6 or 6.8 or 6.9 or 7.0 or 7.1 or 7.2; at least about any of 5.0 or 5.2 or 5.4 or 5.6 or 5.8 or 6.0 or 6.2 or 6.4 or 6.6 or 6.8 or 7.0 and no more than about 7.2. |
| (d) pH (for the polypeptide production phase) | from about 6.9 to about 7.2; from about 7.0 to about 7.1; from about 6.9 to about 7.1; from about 6.9 to about 7.0; from about 7.0 to about 7.2; from about 7.1 to about 7.2; about any of 6.9 or 7.0 or 7.1 or 7.2; at least about any of 6.9 or 7.0 or 7.1 and no more than about 7.2. |

A medium provided herein in one variation comprises calcium and phosphate. In one variation, the medium comprising calcium and phosphate is a feed medium. In another variation, the medium comprising calcium and phosphate is a basal medium. In some aspects, the feed medium is a production medium. In some aspects, the cell culture medium is a chemically defined cell culture medium. In other aspects, the cell culture medium is a chemically undefined cell culture medium. In any of the aspects, the cell culture media is used for inactivating virus during HTST treatment. In any of the aspects, the total amount of phosphate and calcium in the media is limited to less than about 10 mM during HTST treatment prior to the polypeptide production phase of cell culture. In any of the aspects, the total amount of phosphate and calcium in the media is raised to a level sufficient for protein expression during the polypeptide production phase of cell culture. In any of the aspects, the pH of the media is between about pH 5.0 to about pH 6.9 during HTST treatment. In any of the aspects, the pH of the media is lowered to between about pH 5.0 to about pH 6.9 during HTST treatment prior to the polypeptide production phase of cell culture. In further aspects, the pH of the media is then brought to between about pH 6.9 to about pH 7.2 for the polypeptide production phase of cell culture. In one aspect, the pH of the media is then brought to between about pH 6.9 to about pH 7.2 after HTST treatment for the polypeptide production phase of cell culture.

A medium provided herein in one variation comprises a cell culture media wherein the media has a pH of between about pH 5.0 to about pH 6.9. In one variation, the medium comprising calcium and phosphate is a feed medium. In another variation, the medium comprising calcium and phosphate is a basal medium. In some aspects, the cell culture medium is a chemically defined cell culture medium. In other aspects, the cell culture medium is a chemically undefined cell culture medium. In any of the aspects, the cell culture media is used for inactivating virus during HTST treatment. In any of the aspects, the cell culture media is used for inactivating virus during HTST treatment. In any of the aspects, the pH of the media is lowered to between about pH 5.0 to about pH 6.9 during HTST treatment prior to the polypeptide production phase of cell culture. In further aspects, the pH of the media is then brought to between about pH 6.9 to about pH 7.2 for the polypeptide production phase of cell culture. In further aspects, the pH of the media is then brought to between about pH 6.9 to about pH 7.2 after HTST treatment for the polypeptide production phase of cell culture. In any of the aspects, the total amount of phosphate and calcium in the media is limited to less than about 10 mM during HTST treatment. In any of the aspects, the total amount of phosphate and calcium in the media is limited to less than about 10 mM during HTST treatment prior to the polypeptide production phase of cell culture. In any of the aspects, the total amount of phosphate and calcium in the media is raised to a level sufficient for polypeptide production during the polypeptide production phase of cell culture.

In a variation, the invention provides a media wherein the cell media components are adjusted using a response surface as detailed in Example 2. In another variation, the invention provides a media wherein the cell media components are adjusted using the response surface in FIG. 5 and FIG. 6.

In a variation, the invention provides a media wherein trace metals are added to the media after the media is subjected to HTST treatment. In one aspect, a trace metal is at least a one or more trace metal selected from the group consisting of iron or copper. In a variation, the invention provides a media wherein iron is added to the media at an amount between from about 1 µM to about 125 µM after the media is subjected to HTST treatment. In another variation, the iron is at a concentration in the media from about 1 µM to about 125 µM; from about 10 µM to about 120 µM; from about 20 µM to about 110 µM; from about 30 µM to about 100 µM; from about 40 µM to about 90 µM; from about 50 µM to about 80 µM; from about 60 µM to about 70 µM; 1 µM to about 120 µM; 1 µM to about 110 µM; 1 µM to about 100 µM; 1 µM to about 90 µM; 1 µM to about 80 µM; 1 µM to about 70 µM; 1 µM to about 60 µM; 1 µM to about 50 µM; 1 µM to about 40 µM; 1 µM to about 30 µM; 1 µM to about 20 µM; 1 µM to about 10 µM; 10 µM to about 125 µM; 20 µM to about 125 µM; 30 µM to about 125 µM; 40 µM to about 125 µM; 50 µM to about 125 µM; 60 µM to about 125 µM; 70 µM to about 125 µM; 80 µM to about 125 µM; 90

μM to about 125 μM; 100 μM to about 125 μM; 110 μM to about 125 μM; 120 μM to about 125 μM; about any of 1 or 10 or 20 or 30 or 40 or 50 or 60 or 70 or 80 or 90 or 100 or 110 or 120 or 125 μM; at least about any of 1 or 10 or 20 or 30 or 40 or 50 or 60 or 70 or 80 or 90 or 100 or 110 or 120 and no more than about 125 μM after the media is subjected to HTST treatment.

A medium provided herein in one aspect results in one or more favorable attributes when used in a method for inactivation of virus during HTST treatment as compared to attributes when a different medium is used for inactivation of virus during HTST treatment. Precipitate formation in cell culture media subjected to HTST treatment for inactivation of virus for the production of a biologic drug product (e.g., an antibody product) may impact the quality attributes of a biologic drug product, such as the biologic drug product's activity. In addition, precipitate formation in cell culture media during HTST treatment may cause fouling of HTST equipment. Fouling of HTST equipment may impact the ability of HTST treatment to effectively inactivate virus. In one aspect, fouling comprises precipitation on equipment used for HTST treatment. In one variation, a medium as provided herein reduces precipitation in cell culture media when used in a method for inactivating virus in cell culture during HTST treatment as compared to precipitation in a different medium used for inactivation of virus during HTST treatment. In another variation, a medium as provided herein reduces fouling of HTST equipment when used in a method for inactivating virus during HTST treatment as compared to fouling of HTST equipment by a different media used for the inactivation of virus during HTST treatment. In yet another variation, a medium as provided herein reduces precipitate on equipment used for HTST treatment when used in a method for inactivating virus during HTST treatment of the media as compared to precipitate on equipment used for HTST treatment of different media. In another variation, a medium as provided herein inactivates virus in cell culture media when used in a method for HTST treatment of the media as compared to virus inactivation in a different media. In yet another variation, a medium as provided herein reduces precipitation resulting in filter fouling in a method for HTST treatment of the media as compared to virus inactivation in a different media.

One observation is that trace metals, such as copper and iron, that could be important for the cell culture (including the production of polypeptides/proteins, cell growth, survival and/or proliferation) are reduced in the course of HTST treatment. As such, the invention also provides for methods for inactivating virus or adventitious agents in cell culture media while the media maintains suitability for cell culture, said method comprising (a) subjecting the cell culture media to high temperature short time (HTST) treatment; and (b) adjusting one or more parameters selected from the group consisting of pH, calcium level and phosphate level where there is further adjustment of trace metal concentrations. The trace metals can be iron or copper. Iron and/or copper concentrations can be adjusted independently in the media prior to HTST treatment. In some instances, if a decrease in iron and/or copper concentration is anticipated and the amount is generally known, then iron and/or copper can be added to the media prior to HTST treatment. In other instances where the amount of decrease is not known, then iron and/or copper can be reduced (including removed) from the media prior to HTST treatment. Iron and/or copper can then be supplemented to the media following HTST treatment to a suitable level for cell culture.

IV. Compositions and Methods of the Invention

The cell culture media detailed herein can be used in a method for inactivating virus, infectious agents, and/or adventitious agents in cell culture media during HTST treatment. The medium may be used in a method of culturing cells, whether by batch culture, fed batch culture or perfusion culture. The medium may be used in a method for culturing cells to produce polypeptides, including antibodies. The medium may be used in a method for culturing cells to produce cell-based products, including those used for tissue replacement or gene therapy applications. The medium may be used in any cell culture application in which the prevention of potential virus contamination benefits from the use of a heat treatment which inactivates virus while leaving the medium capable of culturing cells. The medium can be used in a method of inactivating virus, infectious agents, and/or adventitious agents in cell culture media subjected to any variations or embodiments of heat treatment described herein.

Methods of inactivating virus, infectious agents, and/or adventitious agents in cell culture media as detailed herein wherein the cell culture media is subjected to HTST treatment are provided. In one variation, the method comprises subjecting the cell culture media to HTST treatment wherein the media comprises one or more medium components as described in Table 1 (e.g., a medium comprising components (a) and (b) or a medium comprising components (a) and (c) or a medium comprising components (b) and (c) or a medium comprising components (a) and (d) or a medium comprising components (b) and (d) or a medium comprising each of components (a)-(c) or (a), (b), and (d) in any of the amounts listed in Table 1).

Methods for reducing fouling of equipment used for HTST treatment to inactivate virus, infectious agents, and/or adventitious agents wherein the cell culture media as detailed herein is used in the equipment and subjected to HTST treatment. In one variation, the method comprises subjecting the cell culture media to HTST treatment wherein the media comprises one or more medium components as described in Table 1 (e.g., a medium comprising components (a) and (b) or a medium comprising components (a) and (c) or a medium comprising components (b) and (c) or a medium comprising components (a) and (d) or a medium comprising components (b) and (d) or a medium comprising each of components (a)-(c) or (a), (b), and (d) in any of the amounts listed in Table 1). In a particular variation, the fouling is precipitate fouling. In one variation, the fouling is filter fouling.

A. Methods for Viral Inactivation and Inactivation of Infectious Agents, and/or Adventitious Agents in Cell Culture Media In some variations, the invention provides methods of inactivating virus, infectious agents, and/or adventitious agents in cell culture media subjected to high temperature treatment wherein the media is compatible for heat treatment as compared to incompatible media. For example, heat treatment of incompatible media precipitates or results in precipitation at temperatures needed for effective inactivation of virus, infectious agents, and/or adventitious agents. As provided in the media disclosed herein, heat treatment compatible media does not precipitate or has reduced precipitation at temperature needed for effective inactivation of virus, infectious agents, and/or adventitious agents. In some aspects, the heat treatment is HTST treatment. In other aspects, the heat treatment is a batch heat treatment including, but not limited to, a sand-bath treatment and an oil-bath method.

In a variation, the invention provides a method for inactivating virus in cell culture media comprising subjecting the cell culture media to HTST treatment wherein the media has a pH of between about pH 5.0 to about pH 6.9 during HTST treatment. In some aspects, the media has a pH of between about pH 5.3 to about pH 6.3 during HTST treatment. In other aspects, the media has a pH of about pH 6.0 during HTST treatment. In some aspects, the pH of the media is lowered to between about pH 5.0 to about pH 6.9 during HTST treatment prior to the polypeptide production phase of cell culture. In a further aspect, the pH of the media is then brought to between about pH 6.9 to about pH 7.2 for the polypeptide production phase of cell culture. In one aspect, the pH of the media is then brought to between about pH 6.9 to about pH 7.2 after HTST treatment for the polypeptide production phase of cell culture. In another variation, the invention provides a method for inactivating virus in cell culture media comprising limiting the total amount of phosphate and calcium in the media to less than about 10 mM during HTST treatment. In a further aspect, the total phosphate and calcium concentration in the media to less than about 9, 8, 7, 6, 5, 4, 3, 2, or 1 mM during HTST treatment. In some aspects, the total amount of phosphate and calcium in the media is limited to less than about 10 mM during HTST treatment prior to polypeptide production phase of cell culture. In a further aspect, the total amount of phosphate and calcium in the media is then raised to a level sufficient for the polypeptide production during the polypeptide production phase of cell culture. In yet another variation, the invention provides a method for inactivating virus in cell culture media comprising subjecting the cell culture media to HTST treatment wherein the media has a pH of between about pH 5.0 to about pH 6.9 and comprising limiting the total amount of phosphate and calcium in the media to less than about 10 mM during HTST treatment. In some aspects, the pH of the media is lowered to between about pH 5.0 to about pH 6.0 and the total amount of phosphate and calcium in the media is limited to less than about 10 mM during HTST treatment prior to polypeptide production phase of cell culture. In a further aspect, the pH of the media is then brought to between about pH 6.9 to about pH 7.2 and the total amount of phosphate and calcium in the media is raised to a level sufficient for the polypeptide production during the polypeptide production phase of cell culture. The virus of any of the method detailed herein may be any virus detailed herein (e.g., a parvovirus) and the medium of the method may be any medium detailed herein, such as a medium comprising medium parameters as detailed in Table 1.

a) Temperature and Temperature Holding Time

In any of the methods detailed herein, the heat treatment comprises raising the temperature of the media to at least about 85° C. for a sufficient amount of time to inactivate the virus in the media. In a further aspect, the temperature of the media is raised to at least about 90° C. for a sufficient amount of time to inactivate the virus in the media. In a further aspect, the temperature of the media is raised to at least about 93° C. for a sufficient amount of time to inactivate the virus in the media. In yet a further aspect, the temperature of the media is raised to at least about 95, 97, 99, 101, or 103 degrees Celsius for a sufficient amount of time to inactivate virus in the media. In yet another further aspect, the temperature of the media is raised to at least about 95, 97, 99, 101, 103, 105, 107, 109, 111, 113, 115, or 117 degrees Celsius for a sufficient amount of time to inactivate virus in the media. In yet another further aspect, the temperature of the media is raised to at least about 86, 87, 88, 89, 90, 91, 92, 93, 94, 95, 96, 97, 98, 99, 100, 101, 102, 103, 104, 105, 106, 107, 108, 109, 100, 111, 112, 113, 114, 115, 116, 117, 118, 119, or 120 degrees Celsius for a sufficient amount of time to inactivate virus in the media. In yet another further aspect, the temperature of the media is raised to at least about 121, 121, 123, 124, 125, 126, 127, 128, 129, 130, 131, 132, 133, 134, 135, 136, 137, 138, 139, 140, 141, 142, 143, 144, 145, 146, 147, 148, 149 or 150 degrees Celsius for a sufficient amount of time to inactivate virus in the media. In some aspects, the temperature of the media is raised to about 95° C. In other aspects, the temperature of the media is raised to about 102° C. In one variation, the temperature of the media is raised to between about 85° C. to about 120° C. for a sufficient amount of time to inactivate virus in the media. In another variation, the temperature of the media is raised to from about 85° C. to about 120° C.; from about 87° C. to about 118° C.; from about 89° C. to about 116° C.; from about 91° C. to about 114° C.; from about 93° C. to about 112° C.; from about 95° C. to about 110° C.; from about 97° C. to about 108° C.; from about 99° C. to about 106° C.; from about 101° C. to about 104° C.; from about 85° C. to about 118° C.; from about 85° C. to about 116° C.; from about 85° C. to about 114° C.; from about 85° C. to about 112° C.; from about 85° C. to about 110° C.; from about 85° C. to about 108° C.; from about 85° C. to about 106° C.; from about 85° C. to about 104° C.; from about 85° C. to about 102° C.; from about 85° C. to about 100° C.; from about 85° C. to about 98° C.; from about 85° C. to about 96° C.; from about 85° C. to about 94° C.; from about 85° C. to about 92° C.; from about 85° C. to about 90° C.; from about 85° C. to about 88° C.; from about 87° C. to about 120° C.; from about 89° C. to about 120° C.; from about 91° C. to about 120° C.; from about 93° C. to about 120° C.; from about 95° C. to about 120° C.; from about 97° C. to about 120° C.; from about 99° C. to about 120° C.; from about 101° C. to about 120° C.; from about 103° C. to about 120° C.; from about 105° C. to about 120° C.; from about 107° C. to about 120° C.; from about 109° C. to about 120° C.; from about 111° C. to about 120° C.; from about 113° C. to about 120° C.; from about 115° C. to about 120° C.; from about 117° C. to about 120° C.; about any of 85° C. or 86° C. or 88° C. or 90° C. or 92° C. or 94° C. or 96° C. or 98° C. or 100° C. or 102° C. or 104° C. or 106° C. or 108° C. or 110° C. or 112° C. or 114° C. or 116° C. or 118° C. or 120° C.; at least about any of 85° C. or 86° C. or 88° C. or 90° C. or 92° C. or 94° C. or 96° C. or 98° C. or 100° C. or 102° C. or 104° C. or 106° C. or 108° C. or 110° C. or 112° C. or 114° C. or 116° C. or 118° C. and no more than about 120° C. for a sufficient amount of time to inactivate virus in the media. In any of the aspects, the temperature of the media is cooled to between about 15° C. to about 40° C. for the polypeptide production during the polypeptide production phase of cell culture.

The heat treatment temperature is held at a temperature holding time to inactivate the virus in the media. The temperature holding time is a sufficient amount of time to inactivate the virus. In any of aspect, a sufficient amount of time to inactivate the virus in the media is from at least about 1 second. In a further aspect, a sufficient amount of time to inactivate the virus in the media is to at least about 2 seconds, 3 seconds, or 4 seconds. In yet a further aspect, a sufficient amount of time to inactivate the virus in the media is to at least about 5, 8, 10, 12, 14, 16, 18, or 20 seconds. In yet another further aspect, a sufficient amount of time to inactivate the virus in the media is to at least about 5, 8, 10, 12, 14, 16, 18, 20, 22, 24, 26, 28, 30, 32, 34, 36, 38, 40, 42, 44, 46, 48, 50, 52, 54, 56, 58, or 60 seconds. In some aspects, a sufficient amount of time to inactivate virus in the media is 10 seconds. In other aspects, a sufficient amount of time to inactivate virus in the media is 2 seconds. In another variation, a sufficient amount of time to inactivate virus in the media is from about 1 to about 60 seconds; from about 2 to about 58 seconds; from about 6 to about 54 seconds; from about 10 to about 50 seconds; from about 14 to about 46 seconds; from about 18 to about 42 seconds; from about 22 to about 38 seconds; from about 26 to about 34 seconds; from about 30 to about 34 seconds; from about 1 to about 56 seconds; from about 1 to about 52 seconds; from about 1 to about 48 seconds; from about 1 to about 44 seconds; from about 1 to about 40 seconds; from about 1 to about 36 seconds; from about 1 to about 32 seconds; from about 1 to about 28 seconds; from about 1 to about 22 seconds; from about 1 to about 18 seconds; from about 1 to about 14 seconds; from about 1 to about 10 seconds; from about 1 to about 6 seconds; from about 1 to about 3 seconds; from about 4 to about 60 seconds; from about 8 to about 60 seconds; from about 12 to about 60 seconds; from about 16 to about 60 seconds; from about 20 to about 60 seconds; from about 24 to about 60 seconds; from about 28 to about 60 seconds; from about 32 to about 60 seconds; from about 36 to about 60 seconds; from about 40 to about 60 seconds; from about 44 to about 60 seconds; from about 48 to about 60 seconds; from about 52 to about 60 seconds; from about 56 to about 60 seconds; about any of 1 or 2 or 4 or 6 or 8 or 10 or 12 or 14 or 16 or 18 or 20 or 22 or 24 or 26 or 28 or 30 or 32 or 34 or 36 or 38 or 40 or 42 or 44 or 46 or 48 or 50 or 52 or 54 or 56 or 58 or 60 seconds; at least about any of 1 or 2 or 4 or 6 or 8 or 10 or 12 or 14 or 16 or 18 or 20 or 22 or 24 or 26 or 28 or 30 or 32 or 34 or 36 or 38 or 40 or 42 or 44 or 46 or 48 or 50 or 52 or 54 or 56 or 58 and no more than about 60 seconds. In other aspects, a sufficient amount of time to inactivate the virus in the media is from at least about 1 minute. In a further aspect, a sufficient amount of time to inactivate the virus in the media is to at least about 2.5 minutes. In yet a further aspect, a sufficient amount of time to inactivate the virus in the media is to at least about 3.5, 4.0, 4.5, 5.0, 5.5, 6.0, 6.5, 7.0, 7.5, 8.0, 8.5, 9.0, 9.5, 10, 10.5 or 11 minutes. In another variation, a sufficient amount of time to inactivate virus in the media is from about 1 to about 11 minutes; 2 to about 10 minutes; 4 to about 8 minutes; from about 1 to about 10 minutes; from about 1 to about 8 minutes; from about 1 to about 6 minutes; from about 1 to about 4 minutes; from about 1 to about 2 minutes; from about 2 to about 11 minutes; from about 4 to about 11 minutes; from about 6 to about 11 minutes; from about 8 to about 11 minutes; about any of 1 or 2 or 3 or 4 or 5 or 6 or 7 or 8 or 9 or 10 or 11 minutes; at least about any of 1 or 2 or 3 or 4 or 5 or 6 or 7 or 8 or 9 or 10 and no more than about 11 minutes.

b) Infectious Agents

The invention provides methods for inactivating virus and/or adventitious agents in cell culture medium comprising subjecting the media to heat treatment. The virus may be any virus detailed herein (e.g., parvovirus) and the cell culture medium may be any cell culture medium detailed herein, such as a medium with components detailed in Table 1. The virus inactivated in the cell culture media during heat treatment may be any virus that is industrially relevant for manufacturing of products (e.g., polypeptides, cells, tissues). Industrially relevant viruses are known to those of skill in the art. Non-limiting examples of industrially relevant viruses are: parvoviradae, paramyoxyiradae, orthomyxoviradae, bunyaviridae, rhabdoviridae, reoviridae, togaviridae, caliciviridae, and picornaviridae. The formal nomenclature for the class of viruses (e.g., parvoviradae), is used interchangeably throughout the specification with a less formal nomenclature (e.g., parvovirus). It is to be understood that either nomenclature refers to the same class of viruses (i.e., parvoviradae encompasses the same class of viruses as parvovirus). In one variation, the virus is a non-enveloped virus. In some aspects, a non-enveloped virus includes, but is not limited to, a single-stranded DNA virus, a double-stranded DNA virus, a double-stranded RNA virus, and a single-stranded RNA virus. In further aspects, a non-enveloped virus includes, but is not limited to, a parvovirus, a reovirus, or a picornavirus. In one variation, the virus is an enveloped virus. In some aspects, an enveloped virus includes, but is not limited to, a single-stranded DNA virus, a double-stranded DNA virus, a double-stranded RNA virus, and a single-stranded RNA virus. In further aspects, an enveloped virus includes, but is not limited to, a retrovirus, a herpes virus, or a hepadnavirus. In any variation of the invention, a virus is selected from the group consisting of an adenovirus, African swine fever-line virus, arenavirus, arterivirus, astrovirus, baculovirus, badnavirus, barnavirus, birnavirus, bromovirus, bunyavirus, calicivirus, capillovirus, carlavirus, caulimovirus, circovirus, closterovirus, comovirus, coronavirus, cotricovirus, cystovirus, deltavirus, dianthovirus, enamovirus, filovirus, flavivirus, furovirus, fusellovirus, geminivirus, hepadnavirus, herpesvirus, hordeivirus, hypovirus, ideaovirus, inovirus, iridovirus, levivirus, lipothrixvirus, luteovirus, machlomovirus, marafivovirus, microvirus, myovirus, necrovirus, nodavirus, orthomyxovirus, papovavirus, paramyxovirus, partitivirus, parvovirus, phycodnavirus, picornavirus, plamavirus, podovirus, polydnavirus, potexvirus, potyvirus, poxvirus, reovirus, retrovirus, rhabdovirus, rhizidiovirus, sequevirus, siphovirus, sobemovirus, tectivirus, tenuivirus, tetravirus, tobamavirus, tobravirus, togavirus, tombusvirus, totivirus, trichovirus, tymovirus, and umbravirus. In some aspects, viruses include, but are not limited to, epizootic hemorrhagic disease virus (EHDV), mice minute virus (MMV), mouse parvovirus-1 (MPV), cache valley virus, Vesivirus 2117, porcine circovirus (PCV 1), porcine circovirus 2 (PCV 2), canine parvovirus (CPV), bovine parvovirus (BPV), or blue tongue virus (BTV). In a particular aspect, the virus is a parvovirus such as murine minute virus. In a variation, the invention provides methods for inactivating a subviral agent in cell culture media comprising subjecting the media to heat treatment. In some aspects, the subviral agent is a viroid or a satellite. In another variation, the invention provides methods for inactivating a virus-like agent in cell culture media comprising subjecting the media to heat treatment.

In another variation, the invention provides methods for inactivating an infectious agent in cell culture media comprising subjecting the media to heat treatment. In some aspects, the infectious agent is a bacterium. In a further aspect, the bacterium is a mycoplasma. In another aspect, the infectious agent is bacteria that are small enough to pass through filters, including any of the filters described herein. In another aspect, the infectious agent is a fungi. In yet another aspect, the infectious agent is a parasite. In still yet another aspect, the infectious agent is a component of an infectious agent. It is understood by one of skill in the art that a component of an infectious agent may be any component that is derived from an infectious agent that is not desired in cell culture media.

In still another variation, the invention provides methods for inactivating an adventitious agent in cell culture media comprising subjecting the media to heat treatment. It is understood by one of the skill in the art that any adventitious agent that is susceptible to inactivation by heat treatment may be inactivated by any of the methods detailed herein using any cell culture medium detailed herein, such as a medium with components detailed in Table 1. In any of the variations, the at least one or more type of infectious and/or adventitious agent is inactivated in the cell culture media during HTST treatment. In some aspects, the one or more type of infectious and/or adventitious agent is a virus, subviral agent, virus-like agent, bacterium, fungi, parasite or a component of an infectious and/or adventitious agent. In any of the variations, the heat treatment is an HTST treatment. It is understood by one of the skill in the art that any of the methods detailed herein for the inactivation of an infectious and/or adventitious agent by heat treatment comprises subjecting any cell culture medium detailed herein, such as a medium with components detailed in Table 1, to any HTST treatment detailed herein.

Inactivation of virus is measured by assays known to those skilled in the art. For example, viral inactivation is determined by measurement or assessment of a given log reduction value (LRV) of active virus. In one aspect, a greater or equal to 3 log reduction value viral loads in cell culture media using HTST treatment at temperatures greater than 95° C. for 2 seconds is determined as inactivating the virus in the media. In another aspect, about a 3 log reduction value in in viral loads in cell culture media using HTST treatment at a temperature of 100° C. for 60 seconds is determined as inactivating the virus in the media. In any of the aspects, the viral load is a MVM load.

c) Heat Treatment Systems

Methods of heat treatment of cell culture media for the inactivation of infectious agents known to those of skill in the art, such as, for example, the methodologies described in Schleh, M. et al. 2009. *Biotechnol. Prog.* 25(3):854-860 and Kiss, R. 2011. *PDA J Pharm Sci and Tech.* 65:715-729, the disclosures of which are incorporated herein by reference in their entirety, may be used for heat treatment of any cell culture medium detailed herein, such as a medium with components detailed in Table 1. For example, high temperature short time (HTST) treatment is used in manufacturing processes to inactivate virus. In a variation, the invention provides a method for inactivating virus in cell culture media comprising subjecting the cell culture media to HTST treatment wherein the media has a pH of between about pH 5.0 to about pH 6.9 during HTST treatment. In another variation, the invention provides a method for inactivating virus in cell culture media comprising limiting the total amount of phosphate and calcium in the media to less than about 10 mM during HTST treatment. In yet another variation, the invention provides a method for inactivating virus in cell culture media comprising subjecting the cell culture media to HTST treatment wherein the media has a pH of between about pH 5.0 to about pH 6.9 and comprising limiting the total amount of phosphate and calcium in the media to less than about 10 mM during HTST treatment. HTST treatment can comprise an HTST cycle wherein the cell culture media is heated from an ambient temperature or 37° C. to about 102° C., wherein the cell culture media is held at 102° C. during a temperature holding time of about 10 seconds, and wherein the cell culture media is then cooled to about ambient temperature or about 37° C. In some aspects, the ambient temperature is between from about 15° C. to about 30° C. In other aspects, the ambient temperature is between from about 18° C. to about 25° C. HTST treatment can be a continuous flow process that uses two heat exchangers, one to heat the fluid and one to cool the fluid, with tubing in between to provide a desired temperature holding time for a given flow rate. In one aspect, inactivation of virus in the cell culture media comprises subjecting the cell culture media to one cycle of HTST treatment. In another aspect, inactivation of virus in the cell culture media comprises subjecting the cell culture media to at least two or more cycles of HTST treatment. In one aspect the flow rate is 100 LPM. In another aspect the flow rate is 125 LPM. In yet another aspect, the flow rate may be any flow rate that is suitable to provide the appropriate temperature and holding time at temperature for virus and/or adventitious agent inactivation. In any aspect, the cell culture media is heated from about 37° C. to about 102° C., wherein the cell culture media is held at 102° C. for a sufficient amount of time to inactivate virus, and wherein the cell culture media is then cooled to about 37° C. In a further aspect, a sufficient amount of time to inactivate virus is about 10 seconds. In any aspects, a sufficient amount of time to inactivate virus is any temperature holding time as detailed herein. In any aspects, the temperature to inactivate the virus during the temperature holding time is any temperature detailed herein. In one aspect, the temperature to inactivate the virus is between from about 85° C. to about 120° C. In one variation, the cell culture media is heated from about 15° C. to about 102° C., wherein the cell culture media is held at 102° C. during a temperature holding time of about 10 seconds, and wherein the cell culture media is then cooled to about 37° C. In another variation, the cell culture media is heated from about 37° C. to about 102° C., wherein the cell culture media is held at 102° C. during a temperature holding time of about 10 seconds, and wherein the cell culture media is then cooled to about 37° C.

For HTST treatment, a cell culture media volume of between from about 0.5 to about 20,000 liters (L) is processed by equipment used for HTST treatment to inactivate virus. It is understood by one of skill in the art that a cell culture media volume less than about 0.5 L or greater than about 20,000 L can be processed by equipment used for HTST treatment in any of the methods detailed herein using any cell culture medium detailed herein, such as a medium with components detailed in Table 1. In one aspect, a cell culture media volume of between from about 0.5 L to about 20,000 L is processed in one HTST run. In other aspects, a cell culture media volume of between from about 0.5 L to about 20,000 L is processed in at least a two or more HTST run. As used herein, the term "HTST run" can refer to the process wherein a specified amount of media is subjected to HTST treatment in equipment (e.g., HTST skid) used for HTST treatment for at least one cycle (e.g., heating, hold, cooling) of HTST treatment. It is understood by one of skill in the art that any equipment, such as an HTST skid, used for HTST treatment can be used for heat treatment of any cell culture media detailed herein, such as a medium with components detailed in Table 1. In one aspect, an HTST run can comprise continuous processing of at least one or more cell culture media volume of between from about 0.5 L to about 20,000 L. In another aspect, an HTST run can comprise batch processing of at least one or more cell culture media volume from about 0.5 L to about 20,000 L. In any aspect, the at least one or more cell culture media volume can be the same type of cell culture media (e.g., Media 1). In any aspect, the at least one or more cell culture media volume can be at least one or more of a type of cell culture media (e.g., Media 1 and Media 2). In any aspects of the methods detailed herein, a cell culture media volume of between from at least about 0.5 L is processed through equipment for HTST treatment to inactivate virus. In a further aspect, a cell culture media volume of between from at least about 2 L is processed through equipment for HTST treatment to inactivate virus. In yet a further aspect, a sufficient amount of time to inactivate the virus in the media is to at least about 5, 10, 50, 100, 500, 1000, 5000, 10000, or 15000 liters. In some aspects, a cell culture media volume of 2 L is processed through equipment for HTST treatment to inactivate virus. In other aspects, a cell culture media volume of 12000 L is processed through equipment for HTST treatment to inactivate virus. In another variation, a cell culture media volume from about 0.5 to about 20000; from about 2 to about 18000; from about 10 to about 16000; from about 20 to about 14000; from about 40 to about 12000; from about 80 to about 10000; from about 100 to about 8000; from about 200 to about 6000; from about 400 to about 4000; from about 800 to about 2000; from about 0.5 to about 18000; from about 0.5 to about 16000; from about 0.5 to about 14000; from about 0.5 to about 12000; from about 0.5 to about 10000; from about 0.5 to about 8000; from about 0.5 to about 6000; from about 0.5 to about 4000; from about 0.5 to about 2000; from about 0.5 to about 800; from about 0.5 to about 600; from about 0.5 to about 400; from about 0.5 to about 200; from about 0.5 to about 100; from about 0.5 to about 50; from about 0.5 to about 20; from about 0.5 to about 10; from about 0.5 to about 5; from about 0.5 to about 2; from about 2 to about 20000; from about 10 to about 20000; from about 100 to about 20000; from about 500 to about 20000; from about 1000 to about 20000; from about 1500 to about 20000; from about 2000 to about 20000; from about 5000 to about 20000; from about 1000 to about 20000; from about 15000 to about 20000; from about 1750 to about 20000 liters; about any of 0.5 or 2 or 10 or 100 or 1000 or 10000 or 20000 liters; at least about any of 0.5 or 2 or 10 or 100 or 1000 or 10000 and no more than about 20000 liters is processed through equipment for HTST treatment to inactivate virus.

Methods of inactivating virus during cell culture processing are known to those of skill in the art, such as, for example, the methodologies described in Kiss, R. 2011. PDA *J Pharm Sci and Tech.* 65:715-729, the disclosure of which is incorporated herein by reference in its entirety, may be used in combination with HTST treatment of any cell culture medium detailed herein, such as a medium with components detailed in Table 1. For example, high temperature short time (HTST) treatment can be used in combination with at least one or more virus barrier treatments in manufacturing processes to remove virus from cell culture media. In some aspects, a one or more virus barrier treatment includes, but is not limited to, heat sterilization, UV light exposure, gamma irradiation, and filtration. In some aspects, a virus barrier treatment is filtration. The present invention provides methods for removing and/or inactivating a virus in cell culture media subjected to HTST treatment, wherein the virus is removed from cell culture media by filtration in a step after the cell culture media is subjected to HTST treatment. In some aspects filtration is ultrafiltration. Prior to ultrafiltration, one or more media components such as components listed in Table 1 are added to the cell culture media subjected to HTST treatment. In some aspects, prior to ultrafiltration, one or more media components such as trace metals (e.g., iron or copper) are added to the cell culture media subjected to HTST treatment.

Ultrafiltration membranes may be formed from regenerated cellulose, polyethersulfone, polyarylsulphones, polysulfone, polyimide, polyamide, polyvinylidenedifluoride (PVDF) or the like. Representative ultrafiltration membranes include, but are not limited to Viresolve® membranes, Viresolve® Pro membranes, Viresolve® 180 membranes, Viresolve® 70 membranes, Viresolve® NFP membranes, Viresolve® NFR membranes, Retropore™ membranes, Virosart CPV membranes, Planova 75 membranes, Planova 35 membranes, Planova 20 membranes, Planova 15N membranes, VAG 300 membranes, Ultipor DVD membranes, Ultipor DV50 membranes, Ultipor DV20 membranes, and DVD Zeta Plus VR™ filters. In some aspects, the ultrafiltration membrane is capable of removing parvovirus particles. In some aspects, the ultrafiltration membrane is a parvovirus retention membrane.

The pore size of the ultrafiltration membranes should be small enough to retain undesirable virus particles while allowing the one or more proteins in the aqueous solution to pass through the membrane. In some embodiments of the invention, the pore size of the ultrafiltration membrane is less than 10 nm, 10 nm, 20 nm, 30 nm, 40 nm, 50 nm, 60 nm, 70 nm, 80 nm, 90 nm, 100 nm, 125 nm, 150 nm, 175 nm or 200 nm. In some embodiments, the pore size of the ultrafiltration membrane is 20 nm or less.

Ultrafiltration membranes may be characterized by a molecular weight cut off which represents the average molecular weight of a smallest protein that is retained by the ultrafiltration membrane. For example, most globular proteins with a molecular weight greater than 1000 kD will be retained by an ultrafiltration membrane with a molecular weight cut off of 1000 kD at a rate of 80-90% whereas most globular proteins with a molecular weight less than 1000 kD will pass through the ultrafiltration membrane. In some aspects of the invention, the molecular weight cut off of the ultrafiltration membrane is between 200 kD and 1000 kD. In some aspects of the inventions, the ultrafiltration membrane has a molecular weight cut off of 200 kD, 300 kD, 400 kD, 500 kD, 600 kD, 700 kD, 900 kD, or 1000 kD.

Filtration can be effected with one or more ultrafiltration membranes either by dead end (normal) flow filtration (NFF) or by tangential flow filtration (TFF). In NFF the feed stream is passed through a membrane and the large molecular weight substances are trapped in the filter while the filtrate is released at the other end. In TFF the majority of the feed flow travels tangentially across the surface of the filter, rather than into the filter. As such, the filter cake is substantially washed away during the filtration process, increasing the length of time that a filter unit can be operational. Ultrafiltration membranes for either mode of filtration can be supplied in either a cartridge (NFF) form, such as VIRESOLVE® NFP viral filters, or as cassettes (for TFF), such as PELLICON® cassettes. In a preferred embodiment, filtration is normal flow filtration.

More than one ultrafiltration membrane may be used in the processes of the invention. In some embodiments, the more than one ultrafiltration membranes are contacted with the aqueous solution in parallel. HTST treatment in combination with a one more virus barrier treatment may be used for the treatment of any cell culture media disclosed herein, such as a cell culture medium with components detailed in Table 1, for industrial scale production of protein and polypeptide therapeutics.

Cell culture media used during HTST treatment for the inactivation of infectious agents may be HTST compatible media or HTST incompatible media. As used herein, the term "HTST compatible media" can refer to cell culture media that has reduced or no precipitation during HTST treatment. As used herein, the term "HTST incompatible media" can refer to cell culture media that has measurable or detectable precipitation during HTST treatment. In one variation, the invention provides methods for screening HTST compatible cell culture media for use in virus inactivation during HTST treatment wherein the HTST compatible media has reduced precipitation as compared to precipitation in HTST incompatible media. In one aspect, the HTST compatible cell culture has no precipitation as compared to precipitation in HTST incompatible media during HTST treatment. In any variation, the HTST compatible media has higher levels of a trace metal as compared to HTST incompatible media following HTST treatment. In an aspect, a trace metal is at least a one or more trace metal selected from the group consisting of iron or copper. In any variation, the HTST compatible media has lower levels of a trace metal as compared to another HTST compatible media. In an aspect, a trace metal is at least a one or more trace metal selected from the group consisting of iron or copper. The invention provides for methods to convert HTST incompatible media to HTST compatible media. In a variation, the invention provides a method to convert HTST incompatible media to HTST compatible media wherein the cell media components are adjusted as detailed in Table 1. In another variation, the invention provides a method to convert HTST incompatible media to HTST compatible media wherein the cell media components are adjusted using a response surface as detailed in Example 2. In a variation, the invention provides a method to convert HTST incompatible media to HTST compatible media wherein the pH of the media is adjusted to between about pH 5.0 to about pH 6.9. In another variation, the invention provides a method to convert HTST incompatible media to HTST compatible media wherein the pH of the media is adjusted to between about pH 5.0 to about pH 7.2. In some aspects, the pH of the HTST incompatible media is adjusted to between about pH 5.3 to about pH 6.3 to convert the HTST incompatible media to HTST compatible media. In a further aspect, the pH of the HTST incompatible media is adjusted to pH 6.0 to convert the HTST incompatible media to HTST compatible media. In some aspects, the pH of the HTST incompatible media is lowered to between about pH 5.0 to about pH 6.9 during HTST treatment prior to the polypeptide production phase of cell culture. In a further aspect, the pH of the HTST incompatible media is then brought to between about pH 6.9 to about pH 7.2 for the polypeptide production phase of cell culture. In a further aspect, the pH of the HTST incompatible media is then brought to between about pH 6.9 to about pH 7.2 after HTST treatment for the polypeptide production phase of cell culture. In some aspects, the pH of the HTST incompatible media is between about pH 5.0 to about pH 7.2 during HTST treatment prior to the polypeptide production phase of cell culture. In a variation, the invention provides a method to convert HTST incompatible media to HTST compatible media wherein the total amount of phosphate and calcium in the media is adjusted to less than about 10 mM. In a further aspect, the total phosphate and calcium concentration in the HTST incompatible media is adjusted to less than about 9, 8, 7, 6, 5, 4, 3, 2, or 1 mM. In some aspects, the total amount of phosphate and calcium in the HTST incompatible media is adjusted to less than about 10 mM prior to polypeptide production phase of cell culture. In a further aspect, the total amount of phosphate and calcium in the HTST incompatible media is then raised to a level sufficient for the polypeptide production during the polypeptide production phase of cell culture.

d) Reduction of Precipitate Formation

In one variation, the invention provides methods for reducing precipitation in cell culture media during heat treatment for the inactivation of virus. The methods comprise adjusting one or more levels of calcium, phosphate and pH in the cell culture media subjected to heat treatment. In one aspect, the heat treatment is HTST treatment. In a variation, the invention provides a method for reducing precipitation in cell culture media during HTST treatment for the inactivation of virus wherein the media has a pH of between about pH 5.0 to about pH 6.9 during HTST treatment. In another variation, the invention provides a method for reducing precipitation in cell culture media during HTST treatment for the inactivation of virus wherein the media has a pH of between about pH 5.0 to about pH 7.2 during HTST treatment. In some aspects, the media has a pH of between about pH 5.3 to about pH 6.3 during HTST treatment. In other aspects, the media has a pH of about pH 6.0 during HTST treatment. In some aspects, the pH of the media is lowered to between about pH 5.0 to about pH 6.9 during HTST treatment prior to the polypeptide production phase of cell culture. In some aspects, the pH of the media is lowered to between about pH 5.0 to about pH 7.2 during HTST treatment prior to the polypeptide production phase of cell culture. In a further aspect, the pH of the media is then brought to between about pH 6.9 to about pH 7.2 for the polypeptide production phase of cell culture. In a further aspect, the pH of the media is then brought to between about pH 6.9 to about pH 7.2 after HTST treatment for the polypeptide production phase of cell culture. In one varation, the pH of the media is between about pH 5.0 to about pH 7.2 during HTST treatment prior to the polypeptide production phase of cell culture. In another variation, the invention provides a method for reducing precipitation in cell culture media during HTST treatment for the inactivation of virus comprising limiting the total amount of phosphate and calcium in the media to less than about 10 mM during HTST treatment. In a further aspect, the total phosphate and calcium concentration in the media to less than about 9, 8, 7, 6, 5, 4, 3, 2, or 1 mM during HTST treatment. In some aspects, the total amount of phosphate and calcium in the media is limited to less than about 10 mM during HTST treatment prior to polypeptide production phase of cell culture. In a further aspect, the total amount of phosphate and calcium in the media is then raised to a level sufficient for the polypeptide production during the polypeptide production phase of cell culture. In yet another variation, the invention provides the invention provides a method for reducing precipitation in cell culture media during HTST treatment for the inactivation of virus wherein the media has a pH of between about pH 5.0 to about pH 6.9 and comprising limiting the total amount of phosphate and calcium in the media to less than about 10 mM during HTST treatment. In some aspects, the pH of the media is lowered to between about pH 5.0 to about pH 6.0 and the total amount of phosphate and calcium in the media is limited to less than about 10 mM during HTST treatment prior to polypeptide production phase cell culture. In a further aspect, the pH of the media is then brought to between about pH 6.9 to about pH 7.2 and the total amount of phosphate and calcium in the media is raised to a level sufficient for the polypeptide production during the polypeptide production phase cell culture.

In some aspects of the invention, any media detailed herein, such as a medium with the specific components detailed in Table 1, reduces precipitation during HTST treatment for the inactivation of infectious agents. In one aspect, specific components in the media reduces precipitation by at least 10%, at least 20%, at least 30%, at least 40%, at least 50%, at least 60%, at least 70%, at least 80%, at least 90%, or at least 100%, when compared to the amount of precipitation present in the same media lacking the specific media components during HTST treatment. Quantitative determination of the amount of precipitation in the media can be made using well known techniques in the art. In one variation, the invention provides a method for reducing precipitation in cell culture media subjected to HTST treatment wherein the media has a pH of about pH 5.0 to about pH 6.9 and wherein the media has reduced precipitation by at least about any of 10%, 20%, 30%, 40%, 50%, 60%, 70%, 80%, 90%, or 100%, when compared to precipitation in media not having a pH of about pH 5.0 to about pH 6.9 during HTST treatment. In one aspect, the media has a pH of about pH 5.3 to about pH 6.3 during HTST treatment and wherein the media has reduced precipitation by at least about any of 10%, 20%, 30%, 40%, 50%, 60%, 70%, 80%, 90%, or 100%, when compared to precipitation in media not having a pH of about pH 5.3 to about pH 6.3 during HTST treatment. In another aspect, the media has a pH of about pH 6.0 during HTST treatment and wherein the media has reduced precipitation by at least about any of 10%, 20%, 30%, 40%, 50%, 60%, 70%, 80%, 90%, or 100%, when compared to precipitation in media not having a pH of about pH 5.3 to about pH 6.0 during HTST treatment. In one variation, the invention provides a method for reducing precipitation in cell culture media comprising limiting the total amount of phosphate and calcium in the media to less than about 10 mM during HTST treatment and wherein the media has reduced precipitation by at least about any of 10%, 20%, 30%, 40%, 50%, 60%, 70%, 80%, 90%, or 100%, when compared to precipitation in media having a total amount of phosphate and calcium greater than about 10 mM during HTST treatment. In one aspect, the total phosphate and calcium concentration in the media is less than about 9, 8, 7, 6, 5, 4, 3, 2, or, 1 mM during HTST treatment and wherein the media has reduced precipitation by at least about any of 10%, 20%, 30%, 40%, 50%, 60%, 70%, 80%, 90%, or 100%, when compared to precipitation in media not having a total phosphate and calcium concentration less than about 9, 8, 7, 6, 5, 4, 3, 2, or, 1 mM during HTST treatment. In one variation, the invention provides a method for reducing precipitation in cell culture media subjected to HTST treatment wherein the media has a pH of about pH 5.0 to about pH 6.9 and comprising limiting the total amount of phosphate and calcium in the media to less than about 10 mM during HTST treatment and wherein the media has reduced precipitation by at least about any of 10%, 20%, 30%, 40%, 50%, 60%, 70%, 80%, 90%, or 100%, when compared to precipitation in media not having a pH of about pH 5.0 to about pH 6.9 and having a total amount of phosphate and calcium greater than about 10 mM during HTST treatment.

The infectious agent of any of the methods detailed herein may be any virus detailed herein (e.g., a parvovirus) and the medium of the methods may be any medium detailed herein, such as a medium with components detailed in Table 1.

B. Methods for Reducing Fouling of Equipment Used for Heat Treatment

The present invention provides methods for reducing fouling of equipment used for HTST treatment to inactivate virus in cell culture media. The inventors have discovered that adjusting the levels of specific components or parameters in cell culture media subjected to HTST treatment reduces fouling of equipment used for HTST treatment to inactivate virus. Any cell culture medium detailed herein, such as a medium with components detailed in Table 1, can be used in any of the methods detailed herein for reducing fouling of equipment used for HTST treatment to inactivate virus. In any of the methods detailed herein, the fouling comprises precipitation on equipment used for HTST treatment.

In one variation, the present invention provides a method of reducing fouling of equipment used for HTST treatment, the method comprising subjecting cell culture media used in the equipment to HTST treatment wherein the media has a pH of between about pH 5.0 to about pH 6.9 during HTST treatment. In one aspect, the media has a pH of between about pH 5.3 to about pH 6.3 during HTST treatment. In another aspect, the media has a pH of about pH 6.0 during HTST treatment. In yet another aspect, the fouling comprises precipitation on equipment used for HTST treatment. In any aspects, the HTST treatment comprises raising the temperature to at least about 85 degrees Celsius for a sufficient amount of time to inactivate the virus in the media. In a further aspect, the temperature of the media is raised to at least about 93 degrees Celsius for a sufficient amount of time to inactivate the virus in the media. In yet a further aspect, the temperature of the media is raised to at least about 95, 97, 99, 101 or 103 degrees Celsius for a sufficient amount of time to inactivate the virus in the media. In one variation, the present invention provides a method for reducing fouling of equipment used for HTST treatment, the method comprising limiting the total amount of phosphate and calcium in cell culture media used in the equipment to less than about 10 mM during HTST treatment. In one aspect, the total phosphate and calcium concentration in the media to less than about 9, 8, 7, 6, 5, 4, 3, 2, or 1 mM during HTST treatment. In a further aspect, the fouling comprises precipitation on equipment used for HTST treatment.

In any aspect, fouling of equipment used for HTST treatment is reduced when an HTST compatible media is used as compared to an HTST incompatible media. In one aspect, an HTST compatible media comprises a pH of between about pH 5.0 to about pH 6.9 during HTST treatment. In another aspect, the HTST compatible media comprises a total amount of phosphate and calcium less than about 10 mM. In yet another aspect, the HTST compatible media comprises a pH of between about pH 5.0 to about pH 6.9 and a total amount of phosphate and calcium less than about 10 mM during HTST treatment. An HTST compatible media is any cell culture medium detailed herein, such as a medium with components detailed in Table 1.

Methods of measuring and monitoring fouling of various equipment used in manufacturing processes are known to those of skill in the art, such as, for example, the methodologies described in Awad, M. 2011. *Heat Transfer: Theoretical Analysis, Experimental Investigations and Industrial Systems*. Chapter 20, page 505-542, the disclosure of which is incorporated herein by reference in its entirety, and may be used to monitor and measure fouling of equipment used for HTST treatment of any cell culture media disclosed herein, such as a medium with components detailed in Table 1 and the media detailed in the Examples. For example, equipment fouling may be measured by measuring changes in heating exchanger steam pressure required to achieve the target medium temperature setpoint or by measuring changes (reduction) in the temperature achieved. In any aspects, fouling comprises precipitation on equipment used for HTST treatment. In one aspect, a one or more equipment susceptible to fouling due to use of HTST incompatible media includes, but is not limited to, an HTST skid, a heat exchanger, a tubing, a filtration device, and a filtration membrane.

C. Methods for Producing Polypeptides with Heat Treated Cell Culture Media a) Cells The methods and compositions provided may employ any cell that is suitable for growth and/or production of a polypeptide (e.g., an antibody) in a medium described herein, including animal, yeast or insect cells. In one aspect, a cell of the methods and compositions is any mammalian cell or cell type suitable to cell culture and to expression of polypeptides. The methods provided herein (e.g., methods of inactivating virus in cell culture media) and compositions may therefore employ any suitable type of cell, including an animal cell. In one aspect, the methods and compositions employ a mammalian cell. The methods and compositions may also employ hybridoma cells. In one variation, the mammalian cell is a non-hybridoma mammalian cell, which has been transformed with exogenous isolated nucleic acid encoding a desired polypeptide, such as an antibody, antibody fragment (including a ligand-binding fragment), and chimeric antibodies. In one variation, the methods and compositions employ mammalian cells selected from the group consisting of human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells/–DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci., 383:44-68 (1982)); MRC 5 cells; FS4 cells; and a human hepatoma line (Hep G2). In a particular variation, the methods and compositions employ CHO cells. In a particular variation, the culturing of CHO cell lines and expression of polypeptides (e.g., antibodies) from CHO cell lines is employed. The polypeptides (e.g., antibodies) may be secreted into the medium disclosed herein from which the polypeptides may be isolated and/or purified or the polypeptide may be released into the medium disclosed herein by lysis of a cell comprising an isolated nucleic acid encoding the polypeptide.

Methods, vectors, and host cells suitable for adaptation to the synthesis of the polypeptide of interest in recombinant vertebrate cell culture are known in the art and are described, for example, in Gething et al., Nature, 293:620-625 (1981); Mantei et al., Nature, 281:40-46 (1979); Levinson et al.; EP 117,060; and EP 117,058. A particularly useful plasmid for mammalian cell culture expression of the polypeptide is pRK5 (EP pub. no. 307,247) or pSVI6B (PCT pub. no. WO 91/08291 published Jun. 13, 1991).

Host cells are transformed with expression or cloning vectors and cultured in nutrient media modified as appropriate for inducing promoters, selecting transformants, or amplifying the genes encoding the desired sequences. For mammalian cells, the calcium phosphate precipitation method of Graham and van der Erb, Virology, 52:456-457 (1978) or the Lipofectamine™ (Gibco BRL) Method of Hawley-Nelson, Focus 15:73 (1193) are preferred. General aspects of mammalian cell host system transformations are known in the art and have been described, for example, by Axel in U.S. Pat. No. 4,399,216 issued Aug. 16, 1983. For various techniques for transforming mammalian cells, see e.g., Keown et al., Methods in Enzymology (1989), Keown et al., Methods in Enzymology, 185:527-537 (1990), and Mansour et al., Nature, 336:348-352 (1988).

The methods and compositions also embrace the use of hybridomas which secrete monoclonal antibodies in cell culture. Monoclonal antibodies are prepared by recovering immune cells (typically spleen cells or lymphocytes from lymph node tissue) from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, Eur. J. Immunol., 6:511 (1976), and also described by Hammerling et al., In: Monoclonal Antibodies and T-Cell Hybridomas, Elsevier, N.Y., pp. 563-681 (1981) has been widely applied to produce hybrid cell lines that secrete high levels of monoclonal antibodies against many specific antigens.

b) Polypeptides

The polypeptides produced by the compositions (e.g., cells) and methods detailed herein and present in the compositions provided herein may be homologous to the host cell, or preferably, may be exogenous, meaning that they are heterologous, i.e., foreign, to the host cell being utilized, such as a human protein produced by a Chinese hamster ovary cell, or a yeast polypeptide produced by a mammalian cell. In one variation, the polypeptide is a mammalian polypeptide (such as an antibody) directly secreted into the medium by the host cell. In another variation, the polypeptide is released into the medium by lysis of a cell comprising an isolated nucleic acid encoding the polypeptide.

In one variation, the polypeptide is a sequence of amino acids for which the chain length is sufficient to produce the higher levels of tertiary and/or quaternary structure. In one aspect, the polypeptide will have a molecular weight of at least about 5-20 kD, alternatively at least about 15-20 kD, preferably at least about 20 kD.

Any polypeptide that is expressible in a host cell may be produced in accordance with the present disclosure and may be present in the compositions provided. The polypeptide may be expressed from a gene that is endogenous to the host cell, or from a gene that is introduced into the host cell through genetic engineering. The polypeptide may be one that occurs in nature, or may alternatively have a sequence that was engineered or selected by the hand of man. An engineered polypeptide may be assembled from other polypeptide segments that individually occur in nature, or may include one or more segments that are not naturally occurring.

Polypeptides that may desirably be expressed in accordance with the present invention will often be selected on the basis of an interesting biological or chemical activity. For example, the present invention may be employed to express any pharmaceutically or commercially relevant enzyme, receptor, antibody, hormone, regulatory factor, antigen, binding agent, etc.

Various polypeptides may be produced according to the methods provided herein, and present in the compositions provided herein. Examples of bacterial polypeptides include, e.g., alkaline phosphatase and .beta.-lactamase. Examples of mammalian polypeptides include molecules such as renin, a growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-.beta.; platelet-derived growth factor (PDGF); fibroblast growth factor such as aFGF and bFGF; epidermal growth factor (EGF); transforming growth factor (TGF) such as TGF-alpha and TGF-beta, including TGF-.beta. 1, TGF-.beta.2, TGF-.beta.3, TGF-.beta.4, or TGF-.beta.5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressing; regulatory proteins; antibodies; and fragments of any of the above-listed polypeptides.

Antibodies are examples of mammalian polypeptides produced according to the methods provided herein and which may be present in the compositions provided. Antibodies are a preferred class of polypeptides that exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V.sub.H) followed by a number of constant domains. Each light chain has a variable domain at one end (V.sub.L) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, while the C regions provide structural support and function in non-antigen-specific interactions with immune effectors. The antigen binding specificity of an antibody or antigen-binding fragment of an antibody is the ability of an antibody to specifically bind to a particular antigen.

The antigen binding specificity of an antibody is determined by the structural characteristics of the V region. The variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Each V region typically comprises three complementarity determining regions ("CDRs", each of which contains a "hypervariable loop"), and four framework regions. An antibody binding site, the minimal structural unit required to bind with substantial affinity to a particular desired antigen, will therefore typically include the three CDRs, and at least three, preferably four, framework regions interspersed therebetween to hold and present the CDRs in the appropriate conformation. Classical four chain antibodies have antigen binding sites which are defined by VH and VL domains in cooperation. Certain antibodies, such as camel and shark antibodies, lack light chains and rely on binding sites formed by heavy chains only. Single domain engineered immunoglobulins can be prepared in which the binding sites are formed by heavy chains or light chains alone, in absence of cooperation between VH and VL.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region may comprise amino acid residues from a "complementarity determining region" or "CDR" (e.g., around about residues 24-34 (L1), 50-56 (L2) and 89-97 (L3) in the VL, and around about 31-35B (H1), 50-65 (H2) and 95-102 (H3) in the VH (Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the VL, and 26-32 (H1), 52A-55 (H2) and 96-101 (H3) in the VH (Chothia and Lesk J. Mol. Biol. 196:901-917 (1987)).

"Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Plückthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

For the purposes herein, an "intact antibody" is one comprising heavy and light variable domains as well as an Fc region. The constant domains may be native sequence constant domains (e.g. human native sequence constant domains) or amino acid sequence variant thereof. Preferably, the intact antibody has one or more effector functions.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

A "naked antibody" is an antibody (as herein defined) that is not conjugated to a heterologous molecule, such as a cytotoxic moiety or radiolabel.

An antibody is directed against an antigen of interest. Preferably, the antigen is a biologically important polypeptide and administration of the antibody to an individual suffering from a disease or condition can result in a therapeutic benefit in that mammal. However, antibodies directed against nonpolypeptide antigens (such as tumor-associated glycolipid antigens; see U.S. Pat. No. 5,091,178) can also be used.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-.beta.; platelet-derived growth factor (PDGF); fibroblast growth factor such as aFGF and bFGF; epidermal growth factor (EGF); transforming growth factor (TGF) such as TGF-alpha and TGF-beta, including TGF-.beta.1, TGF-.beta.2, TGF-.beta.3, TGF-.beta.4, or TGF-.beta.5; insulin-like growth factor-I and -II (IGF-I and IGF-II); des(1-3)-IGF-I (brain IGF-I), insulin-like growth factor binding proteins; CD proteins such as CD3, CD4, CD8, CD18, CD19, CD20, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Preferred molecular targets for antibodies detailed herein include CD proteins such as CD3, CD4, CD8, CD18, CD19, CD20, CD34, and CD40; members of the ErbB receptor family such as the EGF receptor, HER2, HER3 or HER4 receptor; cell adhesion molecules such as LFA-1, Mac1, p150.95, VLA-4, ICAM-1, VCAM, .alpha.4/.beta.7 integrin, and .alpha.v/.beta.3 integrin including either .alpha. or .beta. subunits thereof (e.g. anti-CD11a, anti-CD18 or anti-CD11b antibodies); growth factors such as VEGF; tissue factor (TF); alpha interferon (.alpha.-IFN); an interleukin, such as IL-8; IgE; blood group antigens; flk2/flt3 receptor; obesity (OB) receptor; mp1 receptor; CTLA-4; protein C, and the like.

Antibodies (including fragments thereof, including in turn antigen-binding fragments thereof) that may be produced by the methods herein include without limitation anti-HER2, antibody 2C4, anti-VEGF, antibody C2B8, antiCD11a, anti-tissue factor, IgG4b, anti-CD40, anti-CD20, anti-IgE, E25, and E26, anti-PCSK9 and anti-Beta7.

c) Cell Growth and Polypeptide Production

Generally the cells are combined (contacted) with any of the cell culture media described herein under one or more conditions that promote any of cell growth, maintenance and/or polypeptide production. Methods of growing a cell and producing a polypeptide employ a culturing vessel (bioreactor) to contain the cell and cell culture medium. The culturing vessel can be composed of any material that is suitable for culturing cells, including glass, plastic or metal. Typically, the culturing vessel will be at least 1 liter and may be 10, 100, 250, 500, 1000, 2500, 5000, 8000, 10,000 liters or more. Culturing conditions that may be adjusted during the culturing process include but are not limited to pH and temperature.

A cell culture is generally maintained in the initial growth phase under conditions conducive to the survival, growth and viability (maintenance) of the cell culture. The precise conditions will vary depending on the cell type, the organism from which the cell was derived, and the nature and character of the expressed polypeptide.

The temperature of the cell culture in the initial growth phase will be selected based primarily on the range of temperatures at which the cell culture remains viable. For example, during the initial growth phase, CHO cells grow well at 37° C. In general, most mammalian cells grow well within a range of about 25° C. to 42° C. Preferably, mammalian cells grow well within the range of about 35° C. to 40° C. Those of ordinary skill in the art will be able to select appropriate temperature or temperatures in which to grow cells, depending on the needs of the cells and the production requirements.

In one embodiment of the present invention, the temperature of the initial growth phase is maintained at a single, constant temperature. In another embodiment, the temperature of the initial growth phase is maintained within a range of temperatures. For example, the temperature may be steadily increased or decreased during the initial growth phase. Alternatively, the temperature may be increased or decreased by discrete amounts at various times during the initial growth phase. One of ordinary skill in the art will be able to determine whether a single or multiple temperatures should be used, and whether the temperature should be adjusted steadily or by discrete amounts.

The cells may be grown during the initial growth phase for a greater or lesser amount of time. In one variation, the cells are grown for a period of time sufficient to achieve a viable cell density that is a given percentage of the maximal viable cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In another embodiment the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days. In some cases, the cells may be allowed to grow for a month or more.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art.

An initial culturing step is a growth phase, wherein batch cell culture conditions are modified to enhance growth of recombinant cells, to produce a seed train. The growth phase generally refers to the period of exponential growth where cells are generally rapidly dividing, e.g. growing. During this phase, cells are cultured for a period of time, usually 1 to 4 days, e.g. 1, 2, 3, or 4 days, and under such conditions that cell growth is optimal. The determination of the growth cycle for the host cell can be determined for the particular host cell by methods known to those skilled in the art.

In the growth phase, the basal culture medium and cells may be supplied to the culturing vessel in batch. The culture medium in one aspect contains less than about 5% or less than 1% or less than 0.1% serum and other animal-derived proteins. However, serum and animal-derived proteins can be used if desired. In a particular variation, the basal medium has a pH of between about pH 5.0 to about pH 6.9 during HTST treatment to inactivate virus. In one aspect, the pH of the basal medium is lowered to between about pH 5.0 to about pH 6.9 during HTST treatment to inactivate virus prior to the polypeptide production phase of cell culture. In a further aspect, the pH of the media is then brought to between about pH 6.9 to about pH 7.2 for the polypeptide production phase of cell culture. In a further aspect, the pH of the media is then brought to between about pH 6.9 to about pH 7.2 after HTST treatment for the polypeptide production phase of cell culture. In another particular variation, the basal media comprises limiting the total amount of phosphate and calcium to less than about 10 mM during HTST treatment to inactivate virus. In one aspect, the total amount of phosphate and calcium in the media is limited to less than about 10 mM during HTST treatment to inactivate virus prior to the polypeptide production phase of cell culture. In a further aspect, the total amount of phosphate and calcium in the media is then raised to a level sufficient for the polypeptide production during the polypeptide production phase of cell culture. In another variation, the basal medium has a pH of between about pH 5.0 to about pH 6.9 and a total amount of phosphate and calcium to less than about 10 mM during HTST treatment to inactivate virus. In one aspect, the pH of the basal medium is lowered to between about pH 5.0 to about pH 6.9 and comprises a total amount of phosphate and calcium to less than about 10 mM during HTST treatment to inactivate virus prior to the polypeptide production phase of cell culture. In a further aspect, the pH of the media is then brought to between about pH 6.9 to about pH 7.2 and the total amount of phosphate and calcium in the media is raised to a level sufficient for the polypeptide production during the polypeptide production phase of cell culture. In any of the aspects, the basal medium is a chemically defined medium. In any of the aspects, the basal medium is a chemically undefined medium. Amino acids, vitamins, trace elements and other media components at one or two times the ranges specified in European Patent EP 307,247 or U.S. Pat. No. 6,180,401 may be used, which documents are herein incorporated by reference in their entireties.

Alternatively, commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the animal cells and may be supplemented with chemically defined media constituents as detailed herein (e.g., by use of a kit as provided). In addition, any of the media described in Ham and Wallace, Meth. Enz., 58:44 (1979), Barnes and Sato, Anal. Biochem., 102:255 (1980), U.S. Pat. Nos. 4,767,704; 4,657,866; 4,927,762; or U.S. Pat. No. 4,560,655; WO 90/03430; WO 87/00195; U.S. Pat. No. Re. 30,985; or U.S. Pat. No. 5,122,469, the disclosures of all of which are incorporated herein by reference in their entirety, may be used as culture media for the host cells, each of which may be supplemented with chemically defined media constituents as detailed herein (e.g., by use of a kit as provided).

Any media provided herein may also be supplemented as necessary with hormones and/or other growth factors (such as insulin, transferrin, or epidermal growth factor), ions (such as sodium, chloride, calcium, magnesium, and phosphate), buffers (such as HEPES), nucleosides (such as adenosine and thymidine), trace elements (defined as inorganic compounds usually present at final concentrations in the micromolar range), trace metals (such as iron and copper), and glucose or an equivalent energy source. Any other necessary supplements may also be included at appropriate concentrations that would be known to those skilled in the art.

At a particular point in their growth, the cells may form an inoculum to inoculate a culture medium at the start of culturing in the production phase. Alternatively, the production phase may be continuous with the growth phase. The cell growth phase is generally followed by a polypeptide production phase.

During the polypeptide production phase, the cell culture may be maintained under a second set of culture conditions (as compared to the growth phase) conducive to the survival and viability of the cell culture and appropriate for expression of the desired polypeptide. For example, during the subsequent production phase, CHO cells express recombinant polypeptides and proteins well within a range of 25° C. to 35° C. Multiple discrete temperature shifts may be employed to increase cell density or viability or to increase expression of the recombinant polypeptide or protein. As used herein, the term "polypeptide production phase" or "protein expression phase" can refer to the cell culture phase wherein the cell culture produces a biologic drug product (e.g., a polypeptide).

The cells may be maintained in the subsequent production phase until a desired cell density or production titer is reached. In one embodiment, the cells are maintained in the subsequent production phase until the titer to the recombinant polypeptide reaches a maximum. In other embodiments, the culture may be harvested prior to this point. For example, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. In some cases, it may be desirable to allow the viable cell density to reach a maximum, and then allow the viable cell density to decline to some level before harvesting the culture.

In certain cases, it may be beneficial or necessary to supplement the cell culture during the subsequent polypeptide production phase with nutrients or other medium components that have been depleted or metabolized by the cells. For example, it might be advantageous to supplement the cell culture with nutrients or other medium components observed to have been depleted during monitoring of the cell culture. In some aspects, the one or more depleted components include calcium, phosphate, iron, and copper prior to the subsequent production phase. In some aspects, supplemented media components include calcium, phosphate, iron, and copper. Alternatively or additionally, it may be beneficial or necessary to supplement the cell culture prior to the subsequent polypeptide production phase. In some aspects, the cell culture is supplemented with one or more media components including calcium, phosphate, iron, and copper prior to the subsequent production phase. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), trace metals (such as iron and copper), amino acids, lipids, or glucose or other energy source. As used herein, the term "feed medium" or "production medium" refers to a cell culture medium used during the polypeptide production phase of cell culture.

In a particular variation, the feed media has a pH of between about pH 5.0 to about pH 6.9 during HTST treatment to inactivate virus. In some aspects, the pH of the feed media is then brought to between about pH 6.9 to about pH 7.2 for the polypeptide production phase of cell culture. In some aspects, the pH of the feed media is then brought to between about pH 6.9 to about pH 7.2 after HTST treatment for the polypeptide production phase of cell culture. In another particular variation, the feed media comprises limiting the total amount of phosphate and calcium to less than about 10 mM during HTST treatment to inactivate virus. In some aspects, the total amount of phosphate and calcium in the feed media is then raised to a level sufficient for the polypeptide production during the polypeptide production phase of cell culture. In another variation, the feed media has a pH of between about pH 5.0 to about pH 6.9 and a total amount of phosphate and calcium to less than about 10 mM during HTST treatment to inactivate virus. In some aspects, the pH of the media is then brought to between about pH 6.9 to about pH 7.2 and the total amount of phosphate and calcium in the media is raised to a level sufficient for the polypeptide production during the polypeptide production phase of cell culture. In any of the aspects, the feed medium is a chemically defined medium. In any of the aspects, the feed medium is a chemically undefined medium. Amino acids, vitamins, trace elements and other media components at one or two times the ranges specified in European Patent EP 307,247 or U.S. Pat. No. 6,180,401 may be used, which documents are herein incorporated by reference in their entireties.

D. Kits

A kit for supplementing a cell culture medium with chemically defined constituents is described. The kit may contain dried constituents to be reconstituted, and may also contain instructions for use (e.g., for use in supplementing a medium with the kit constituents). The kit may contain the medium constituents provided herein in amounts suitable to supplement a cell culture medium. In one variation, a kit comprises medium components of Table 1. In another variation, a kit comprises medium constituents to adjust the media pH to pH levels disclosed in Table 1.

E. Compositions

Compositions comprising the cell culture medium and one or more other components, such as a cell or a desired polypeptide (e.g., an antibody), are also provided. In one variation is provided a composition comprising: (a) a cell comprising an isolated nucleic acid encoding a polypeptide; and (b) a cell culture medium as provided herein. In another variation is provided a composition comprising: (a) a polypeptide; and (b) a cell culture medium as provided herein, where in one aspect the polypeptide is secreted into the medium by a cell comprising an isolated nucleic acid encoding the polypeptide. In yet another variation is provided a composition comprising: (a) a polypeptide; and (b) a cell culture medium as provided herein, where in one aspect the polypeptide is released into the medium by lysis of a cell comprising an isolated nucleic acid encoding the polypeptide. The cell of the composition may be any cell detailed herein (e.g., a CHO cell) and the medium of the composition may be any medium detailed herein, such as a medium comprising medium components as detailed in Table 1. Likewise, the polypeptide of the composition may be any polypeptide detailed herein, such as an antibody.

F. Systems for Viral Inactivation

The invention contemplates systems and/or processes for inactivation of virus for cell culture media. The system can include, but is not limited to: media, media containment unit(s), pH meter (or another means for measuring pH), means for measurement of and/or quantitation of calcium and/or phosphate concentration and/or amount; means for transfer of media (e.g. tubes), heat source(s) for increasing temperature of the media, means for adjustment of a target set point (e.g., temperature), holding containment units (e.g., holding tubes), cooling source(s) to decrease the temperature of the media, air supply, means for pressure input and output (e.g., pressure valves, peristaltic pump, centrifugal pump, positive displacement pump), means for media input and output, means for gas input and output, means for filtration, means for adjustment of flow rate and other aspects related to flow dynamics, and optionally connected to a bioreactor where the production of desired polypeptides or cell culture or cell culture media is made.

A system for viral inactivation comprising the elements above can also include a system for heat treatment. An exemplary heat treatment system that can be used with various parameters (e.g., pH, calcium and/or phosphate concentrations) described herein is shown in FIG. 1. Such systems described herein are useful for carrying out the processes for inactivating viruses in cell culture media so that the media can be used for production of various end products (e.g., polypeptides, antibodies, etc.)

G. Exemplary Embodiments

In one aspect, the invention provides for methods for inactivating virus or adventitious agents in cell culture media while the media maintains suitability for cell culture, said method comprising (a) subjecting the cell culture media to high temperature short time (HTST) treatment; and (b) adjusting one or more parameters selected from the group consisting of pH, calcium level and phosphate level.

In any of the embodiments above, the methods further comprise adjusting trace metal concentrations.

In any of the embodiments above, the trace metals is selected from the group consisting of iron and copper.

In any of the embodiments above, iron and/or copper concentrations are adjusted in the media prior to HTST treatment.

In any of the embodiments above, iron and/or copper is removed from the media prior to HTST treatment.

In any of the embodiments above, the methods further comprise supplementing iron and/or copper to the media following HTST treatment to a suitable level for cell culture.

In any of the embodiments above, the pH is adjusted when the media comprises calcium and phosphate.

In any of the embodiments above, the pH is adjusted in preparing the media prior to HTST treatment to a suitable low level.

In any of the embodiments above, the pH is adjusted by lowering to a suitable level.

In any of the embodiments above, the pH is adjusted to less than about 7.2.

In any of the embodiments above, the pH is adjusted to about 5.0-7.2.

In any of the embodiments above, the method further comprise adjusting the pH following HTST treatment to a suitable level for cell culture.

In any of the embodiments above, the pH is adjusted to about 6.9-7.2.

In any of the embodiments above, the calcium level is adjusted when the media comprises phosphate.

In any of the embodiments above, the calcium level is reduced.

In any of the embodiments above, the calcium level is reduced such that formation of complexes comprised of calcium and phosphate is suppressed.

In any of the embodiments above, calcium is removed from the media prior to HTST treatment.

In any of the embodiments above, the pH is adjusted such that formation of complexes comprised of calcium and phosphate is suppressed.

In any of the embodiments above, the methods further comprise adjusting the calcium level following HTST treatment to a suitable level for cell culture.

In any of the embodiments above, the phosphate level is adjusted when the media comprises calcium.

In any of the embodiments above, the phosphate level is reduced.

In any of the embodiments above, the phosphate level is reduced such that formation of complexes comprised of calcium and phosphate is suppressed.

In any of the embodiments above, phosphate is removed from the media prior to HTST treatment.

In any of the embodiments above, the pH is adjusted such that formation of complexes comprised of calcium and phosphate is suppressed.

In any of the embodiments above, the methods further comprise adjusting the phosphate level following HTST treatment to a suitable level for cell culture.

In any of the embodiments above, the total phosphate and calcium concentration in the media is less than about 10, 9, 8, 7, 6, 5, 4, 3, 2, or 1 mM during HTST treatment.

In any of the embodiments above, the calcium and phosphate levels are adjusted.

In any of the embodiments above, pH, calcium, and phosphate levels are adjusted.

In any of the embodiments above, precipitate formation is suppressed.

In any of the embodiments above, fouling of equipment used for HTST treatment is reduced.

In any of the embodiments above, filter fouling is suppressed.

In any of the embodiments above, the HTST treatment comprises raising the temperature of the media to at least about 85 degrees Celsius for a sufficient amount of time to inactivate virus or adventitious agents in the media.

In any of the embodiments above, the temperature of the media is raised to at least about 93, 95, 97, 99, 101, 102, or 103 degrees Celsius for a sufficient amount of time to inactivate the virus in the media.

In any of the embodiments above, the temperature is raised for at least about 5, 6, 7, 8, 9, 10, 11, 12, 13, 14, or 15 seconds.

In any of the embodiments above, the virus is selected from the group consisting of parvoviradae, paramyoxyiradae, orthomyxoviradae, bunyaviridae, rhabdoviridae, reoviridae, togaviridae, calciviridae, and picornaviridae.

In any of the embodiments above, the virus is an enveloped virus.

In any of the embodiments above, the virus is a non-enveloped virus.

In any of the embodiments above, the adventitious agent is bacteria.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

The following Examples are provided to illustrate but not to limit the invention.

All references disclosed herein are incorporated herein by reference in their entireties for all purposes.

EXAMPLES

Viral agent contamination of cell culture processes poses a threat to production of biologic drugs (e.g., recombinant proteins) from cell lines and raises potential safety concerns regarding the ability to clear viral agents during purification of the product. Several approaches can be taken to minimize the risk of adventitious agents getting into and through the production processes including use of high temperature short time (HTST) treatment of cell culture media. However, although effective at inactivating virus when functioning properly, a given media may be incompatible with use of HTST treatment for viral particle inactivation (Schleh, M. et al. 2009. *Biotechnol. Prog.* 25(3):854-860 and Kiss, R. 2011. *PDA J Pharm Sci and Tech.* 65:715-729). Media incompatibility can result in fouling of the process-contacting surfaces in the HTST equipment. One contributor of fouling is precipitation of media as a result of the heating and cooling operations of HTST treatment. Precipitation leads to deposition of residue that fouls the heat exchangers and results in HTST skid shutdown due to an inability of the system to maintain temperature set-points. Additionally, precipitation in media that is incompatible with heat treatment can cause fouling of process filters used to remove bacteria that were not inactivated in the media by HTST conditions. Filter fouling due to precipitation can lead to processing failure and significant increases in filtration costs. Furthermore, precipitation in media incompatible with heat treatment can adversely affect cell culture performance (e.g., product titer, cell growth, cell viability) and product quality.

As described herein, several modifications to media have been identified that make it compatible for use during HTST treatment or other heat treatment for the inactivation of virus. Several media formulations have been identified that reduce or prevent precipitation on equipment used for HTST treatment to inactivate virus. Methods of inactivating virus in the media provided herein are described, as are methods for reducing precipitate on equipment used for HTST treatment to inactivate virus. A media may in one aspect have a pH of between about pH 5.0 to about pH 6.9 during HTST treatment for use in virus inactivation. A media in another aspect may have a pH of between about pH 5.0 to about pH 6.9 during HTST treatment for use in virus inactivation prior to the protein expression phase of cell culture. A media in a further aspect may have a pH brought to between about pH 6.9 to about pH 7.2 for the protein expression phase of cell culture. A media in one aspect may comprise limiting the total amount of phosphate and calcium to less than about 10 mM during HTST treatment for use in virus inactivation. A media in another aspect may comprise limiting the total amount of phosphate and calcium to less than about 10 mM during HTST treatment for use in virus inactivation prior to the protein expression phase of cell culture. A media in a further aspect may have the total amount of phosphate and calcium raised to a level sufficient for protein expression during the protein expression phase of cell culture. In any aspects, the media may comprise a pH of between about pH 5.0 to about pH 6.9 and a total amount of phosphate and calcium to less than about 10 mM during HTST treatment for use in virus inactivation in cell culture media. The media find use through all phases of cell culture and may be used in the basal and/or feed medium. The media finds use for reducing precipitate on equipment used for HTST treatment to inactivate virus. Kits for supplementing a cell culture medium with chemically defined constituents is also contemplated.

Example 1

Validation of Sand-Bath Screening Method for Reproducing Observations from HTST Skid Operation During manufacturing scale HTST treatment, liquid preparations of cell culture media are heated to 102° C. for 10 seconds in a continuous flow process that uses two heat exchangers, one to heat the fluid and one to cool the fluid, with tubing in between to provide a desired hold time for a given flow rate (FIG. 1). The sand-bath screening method was used to more rapidly test media compositions with lab-scale (~20 mL) media volume requirements for behavior following heat treatment. This method was based on "worst-case" heat exposure to screen and identify compatible media for use in pilot and manufacturing scale HTST skids (Table 2).

TABLE 3

Media formulations tested for heat treatment stability

| Media Description | Target pH |
| --- | --- |
| Media 1 (feed, undefined) | 6.40 |
|  | 7.00 |
| Media 2 (basal, undefined) | 6.70 |
|  | 7.00 | pH Adjustment pH drift due to off-gassing that occurred during the time between the completion of the media preparation and when the heat treatment was applied was corrected. Prior to heat treatment, a 30 mL aliquot from each media preparation was transferred to 50 mL tubes (Falcon) and the original Falcon tube caps were replaced with vented caps from 250 mL Corning Erlenmeyer flasks. The tubes were then placed in an incubator with $CO_2$ overlay for 30 minutes to drive down the pH (15% $CO_2$ for pH 6.2 samples and 12% $CO_2$ for all other samples, 200 rpm, 37° C.); this step was able to force the pH below the target. The tubes were manually agitated while monitoring pH using a glass electrode pH probe and meter (Mettler Toledo) until the pH crept back up to target pH. Final pH measurements were taken with NOVA bioprofiler.

Sand-Bath Method

For the sand-bath method, 22 mL of prepared liquid media was transferred to 20 mL glass pressure vessels (Ace glassware). The vessels were sealed with a threaded cap with thermowell so that no air headspace remained in the vessel by filling it full and allowing for excess media to be displaced by the cap and thermowell. The outside of the

TABLE 2

Key differences between the sand-bath apparatus and HTST skid at two scales of operation.

| Characteristic | Sand-bath | Pilot-scale HTST skid | Manufacturing-scale HTST skid |
| --- | --- | --- | --- |
| Process Volume Scale | ~20 mL | ~50 to 400 L | ~1000 s of L |
| Fluid Flow (sample side heat transfer rate) | Static (convection driven by heating) | ~1-2 L/min, plug flow | ~100 L/min, plug flow |
| Material (heat transfer resistance) | Glass | 316 L Stainless Steel | 316 L Stainless Steel |
| Heat exposure profile | Slow step function (ramping up over 5-8 minutes from 19-25° C. or 37° C. to 102° C., held 10 s, then cooled by quenching over several minutes) | Near instantaneous step function (ambient or 37° C. to 102° C., held for 10 s then back to 37° C.) | Near instantaneous step function (ambient or 37° C. to 102° C., held for 10 s then back to 37° C.) |

Materials and Methods

Media Preparation

Media used in this study includes basal production media and batch feed medium with varying pH levels (Table 3). All media was prepared using purified de-ionized water processed through a Millipore SuperQ ultrapure water purification system. Media were prepared using the appropriate media powder stocks (SAFC and Life Technologies). A glass electrode pH probe (Mettler Toledo) and osmometer (Advanced Instruments) were used during liquid preparations to ensure target pH and osmolality for a given preparation. Upon complete dissolution of the components and final pH and osmolality adjustments, the media were filtered using 0.1 μm pore size PES membrane filters into bottles ranging from 250 mL to 1 L (Corning) for small-scale preparations.

container was cleaned to prevent fouling of the outside surface from media directly exposed to the heating source matrix. Teflon tape was used to cover the interface between the lip of the glass vessel and the threaded cap to better seal the glass pressure vessel and protect against sand or thermocouple well oil from getting into samples for heat treatment. The fluidized sandbath (Techne SBS-4) with temperature controller (Techne TC-8D) was configured (compressed air inlet pressure=5 psig, bath temperature=110° C.) and was given 30 minutes to equilibrate. Thermocouples attached to a single VWR digital thermometer were inserted in the sample vessel thermowells geometrically situated in the center of the radial dimension of the tube. Silicone oil was added to the thermocouple well to provide a heat transfer medium between the thermocouple well glass wall and the thermocouple. The sample vessels were placed in the sandbath and a timer was initiated. Temperature kinetic data was recorded approximately every 30-60 seconds. Once a vessel reached 102° C. by thermometer readings, it was maintained in the sand-bath for a 10 second hold. Following the heating and hold steps, the vessels were transferred to a water bath at room temperature until the thermometer temperature reading reached 35° C. After heat treatment, 15 mL of each sample was transferred to a vial for turbidity and visual measurements.

Precipitation Measurements

Media samples were analyzed pre- and post-heat treatment for precipitation by two methods: 1) turbidity via a turbidimeter (2100Q Hach); and 2) centrifugation of the samples in 50-mL Falcon tubes at 10,000×g for 10 minutes (Sorvall RC 6 plus, SS-34 rotor) to sediment precipitates for visual identification and qualitative determination of precipitation based on the pellet size (e.g. none visible, low, moderate, high). Uncentrifuged samples were also analyzed for visual identification of precipitation.

Results

Figure 2:
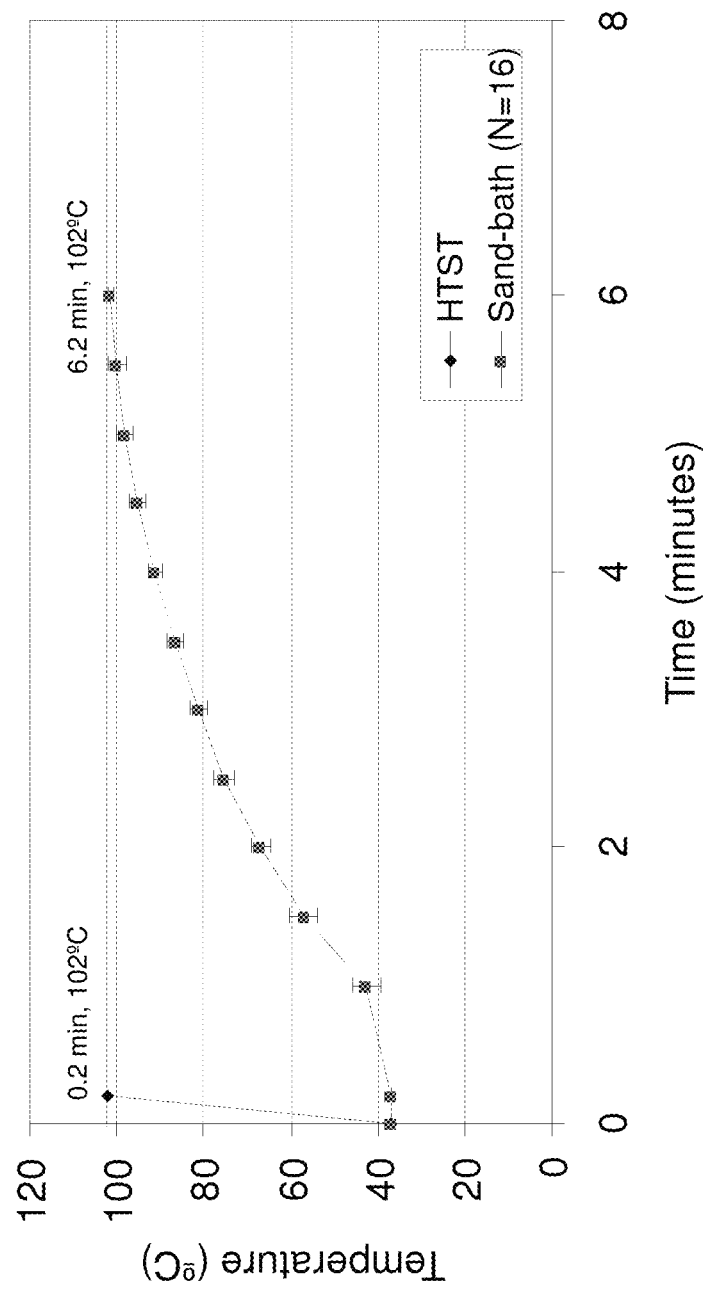
FIG. 2 is a graph depicting heating profiles from the sand-bath method and HTST treatment to the 102° C. target set point. The traces show the heating profiles in minutes where the end-point of each trace was described by the time and temperature at the end-point (e.g. end-point value of "6.2, 102"=end-point value at 6.2 minutes was at 102° C.).

There were two main observations from the sand-bath and HTST heating profiles: 1) the heating profile for the sand-bath heat treatment system was considerably longer than for the larger-scale HTST skid operations and 2) the sand-bath was able to reach the target set point of 102° C. in roughly 6.5 minutes (FIG. 2). The sand-bath method heating profiles consistently ranged from 5 to 8 minutes with a ~6 to ~6.5 minute average time to heat from ambient (~21-25° C.) or 37° C. up to the target 102° C. for the 10 second hold prior to cooling the samples in a water bath. Relative to the manufacturing or pilot scale continuous flow HTST systems, the area under the curve for heating, hold, and cooling was considerably greater in the sand-bath method. Media samples in the sand-bath method were determined to be worst-case for total heat exposure relative to the pilot and manufacturing scale HTST operations. Therefore, any significant changes to components in a given media formulation primarily driven by heat exposure in the sand-bath method would provide relevant data for HTST treatments at larger scales.

Figure 3:
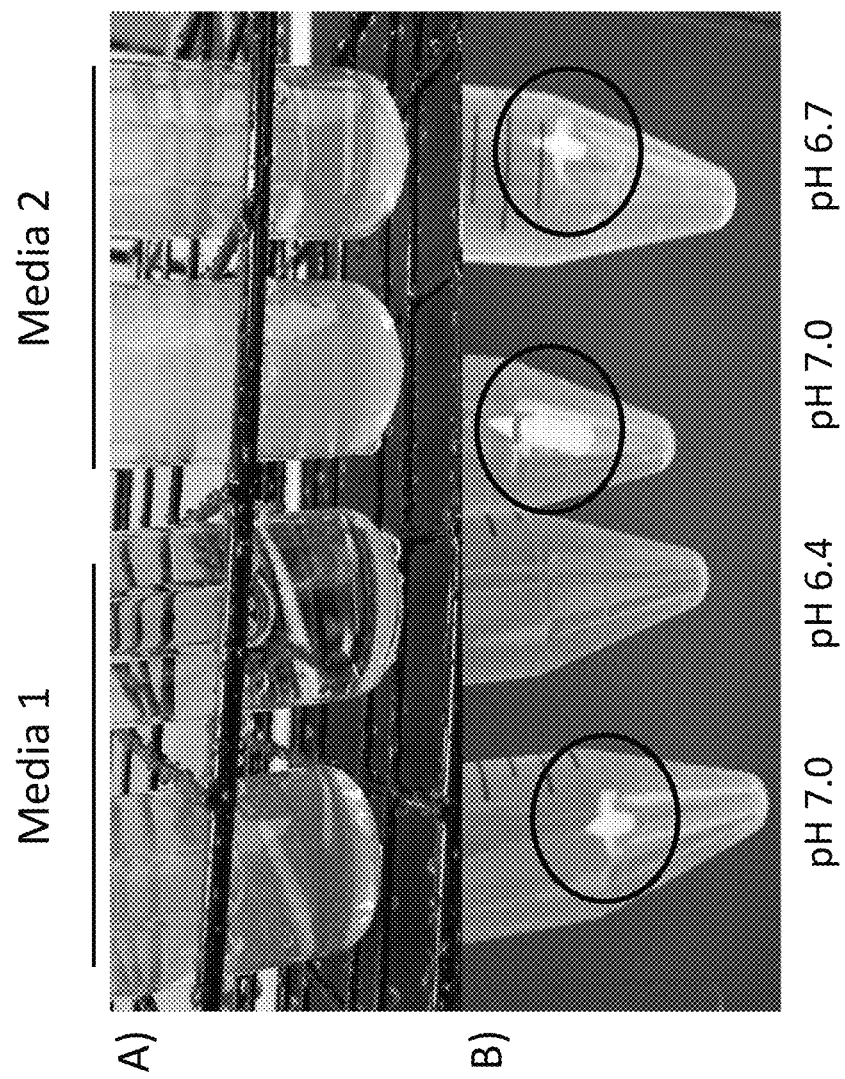
FIG. 3 is a picture of media samples known to precipitate during HTST treatment after heat treatment by the sand-bath method. A) Uncentrifuged samples of Media 1 at pH 7.0 or pH 6.4, and Media 2 at pH 7.0 or pH 6.7 in heat treated pressure vessels. B) Centrifuged aliquots of Media 1 at pH 7.0 or pH 6.4, and Media 2 at pH 7.0 or pH 6.7 from the treated pressure vessels.

It was observed that during HTST treatment, lowering of the pH of Media 1 feed medium formulation from pH 7.0 to pH 6.4 could alleviate any HTST operational issues (Table 3). Similarly, for the Media 2 basal medium formulation, it was found that treating the media at a pH of 6.7 instead of pH 7.0 would also alleviate any operational issues (Table 3). These media were each processed at the two pH levels in the sand-bath method to determine if the sand-bath method could accurate reflect the precipitation behavior that occurred at-scale HTST treatment operations. Visibility measurements before and after heat treatment indicated that the sand-bath system accurately demonstrated precipitation behavior due to heat treatment for media known to have HTST-compatibility issues at neutral pH processing (FIGS. 3A and B). Consistent with "worst-case" for heat exposure based changes to the media, Media 2 still showed signs of precipitation at pH 6.7 in the sand-bath even though it was significantly ameliorated relative to the pH 7.0 treated sample of the same medium. Overall, these results validated the use of the sand-bath method to screen and identify media formulations that would be compatible for use in pilot and manufacturing scale HTST treatment.

Example 2 pH, Calcium, and Phosphate Levels Contribute to Precipitation in Media During Heat Treatment for Viral Inactivation Materials and Methods Media Preparation Media used in this study includes basal production media and batch feed medium at pH levels ranging from about pH 5.9 to about pH 7.5, calcium concentration ranges from about 0 mM to about 3.5 mM (or greater in undefined media), and phosphate concentration ranges from about 0 mM to about 6.5 mM (or greater in undefined media). All media was prepared using purified de-ionized water processed through a Millipore SuperQ ultrapure water purification system. Media were prepared using the appropriate media powder stocks (SAFC and Life Technologies). A glass electrode pH probe (Mettler Toledo) and osmometer (Advanced Instruments) were used during liquid preparations to ensure target pH and osmolality for a given preparation. Upon complete dissolution of the components and final pH and osmolality adjustments, the media were filtered using 0.1 μm pore size PES membrane filters into bottles ranging from 250 mL to 1 L (Corning) for small-scale preparations.

pH Adjustment pH drift due to off-gassing that occurred during the time between the completion of the media preparation and when the heat treatment was applied was corrected. Prior to heat treatment, a 30 mL aliquot from each media preparation was transferred to 50 mL tubes (Falcon) and the original Falcon tube caps were replaced with vented caps from 250 mL Corning Erlenmeyer flasks. The tubes were then placed in an incubator with $CO_2$ overlay for 30 minutes to drive down the pH (15% $CO_2$ for pH 6.2 samples and 12% $CO_2$ for all other samples, 200 rpm, 37° C.); this step was able to force the pH below the target. The tubes were manually agitated while monitoring pH using a glass electrode pH probe and meter (Mettler Toledo) until the pH crept back up to target pH. Final pH measurements were taken with NOVA bioprofiler.

Sand-Bath Method

For the sand-bath method, 22 mL of prepared liquid media was transferred to 20 mL glass pressure vessels (Ace glassware). The vessels were sealed with a threaded cap with thermowell so that no air headspace remained in the vessel by filling it full and allowing for excess media to be displaced by the cap and thermowell. The outside of the container was cleaned to prevent fouling of the outside surface from media directly exposed to the heating source matrix. Teflon tape was used to cover the interface between the lip of the glass vessel and the threaded cap to better seal the glass pressure vessel and protect against sand or thermocouple well oil from getting into samples for heat treatment. The fluidized sandbath (Techne SBS-4) with temperature controller (Techne TC-8D) was configured (compressed air inlet pressure=5 psig, bath temperature=110° C.) and was given 30 minutes to equilibrate. Thermocouples attached to a single VWR digital thermometer were inserted in the sample vessel thermowells geometrically situated in the center of the radial dimension of the tube. Silicone oil was added to the thermocouple well to provide a heat transfer medium between the thermocouple well glass wall and the thermocouple. The sample vessels were placed in the sand-bath and a timer was initiated. Temperature kinetic data was recorded approximately every 30-60 seconds. Once a vessel reached 102° C. by thermometer readings, it was maintained in the sand-bath for a 10 second hold. Following the heating and hold steps, the vessels were transferred to a water bath at room temperature until the thermometer temperature reading reached 35° C. After heat treatment, 15 mL of each sample was transferred to a vial for turbidity and visual measurements.

Precipitation Measurements

Media samples were analyzed pre- and post-heat treatment for precipitation by two methods: 1) turbidity via a turbidimeter (2100Q Hach); and 2) centrifugation of the samples in 50-mL Falcon tubes at 10,000×g for 10 minutes (Sorvall RC 6 plus, SS-34 rotor) to sediment precipitates for visual identification and qualitative determination of precipitation based on the pellet size (e.g. none visible, low, moderate, high). Uncentrifuged samples were also analyzed for visual identification of precipitation.

Results

Several media formulations were prepared with varying levels of pH values as well as calcium and phosphate concentrations (Table 4). The prepared media was assessed for precipitation before and after heat treatment by visual observations of non-centrifuged and centrifuged samples, and by turbidity measurements.

led to lower turbidity (Table 4). In addition, formulations without calcium or with low calcium concentrations also did not show precipitation events and did not have high turbidity measurements even at neutral pH (Table 4). A correlation was between reduced precipitation and lower calcium to phosphate ratios in addition to lower calcium and phosphate concentrations (Table 4). These observations led to the determination that formation of calcium phosphate precipitates upon heating and cooling during heat treatment are a function of calcium concentration, phosphate concentration, and pH levels.

Media 4 was chosen for a full factorial design of experiments (DoE) for multivariate analysis of heat treated formulations in the sand-bath system and the turbidity (NTU) response metric was used to generate a precipitation response surface. The variables that were varied were calcium concentrations (0.1 to 2.9 mM), phosphate concentrations (0.1, 5.9 mM) and pH (6.0 to 7.2). Sorted parameter estimates as determined by turbidity measurements, and confirmed by visual observations, identified that pH-dependent calcium phosphate formation upon heat treatment of a media formulation containing both calcium and phosphate

TABLE 4

Media formulations tested for precipitation in the Sand-bath method

| Media Description | Actual pH | Target pH | Precipitation (Yes/No) | Turbidity (NTU) | [Ca] mM | [PO4] mM | [Ca]/[PO4] ratio |
|---|---|---|---|---|---|---|---|
| Media 1† | 7.00 | 7.00 | Yes | 50.7 | 3.5 | 3.17 | 1.10 |
| (feed, undefined) | N/A | 6.90 | Yes | N/A | 3.5 | 3.17 | 1.10 |
| | N/A | 6.50 | Yes | N/A | 3.5 | 3.17 | 1.10 |
| | 6.40 | 6.40 | No | 1.2 | 3.5 | 3.17 | 1.10 |
| | N/A | 6.20 | No | N/A | 3.5 | 3.17 | 1.10 |
| Media 2† | 7.00 | 7.00 | Yes | 100.2 | 2.1 | 1.9 | 1.11 |
| (basal, undefined) | 6.68 | 6.70 | Yes | 37.5 | 2.1 | 1.9 | 1.11 |
| Media 3 | 7.05 | 7.00 | Yes | 8.3 | 1.5 | 3 | 0.50 |
| (basal, defined) | | | | | | | |
| Media 4 | N/A | 7.20 | Yes | N/A | 1.5 | 3 | 0.50 |
| (basal, defined) | 7.11 | 7.10 | Yes | 23.0 | 1.5 | 3 | 0.50 |
| | 6.93 | 6.70 | No | 19.11 | 1.5 | 3 | 0.50 |
| | 6.35 | 6.30 | No | 2.94 | 1.5 | 3 | 0.50 |
| Media 5† | 7.02 | 7.00 | Yes | 20.5 | 1.3 | 2.6 | 0.5 |
| (basal, undefined) | | | | | | | |
| Media 6 | 7.07 | 7.10 | No | 1.0 | 0.42 | 2.54 | 0.17 |
| (basal, defined) | | | | | | | |
| Media 7 | 7.00 | 7.00 | No | 0.5 | 0.4 | 4.15 | 0.10 |
| (basal, defined) | | | | | | | |
| Media 8 | 7.04 | 7.00 | No | 0.2 | 0 | 30 | 0 |
| (feed, defined) | | | | | | | |
| Media 9 | 6.90 | 7.20 | No | 0.2 | 0 | 30 | 0 |
| (feed, defined) | 6.50 | 6.50 | No | 1.1 | 0 | 30 | 0 |
| Media 10 | N/A | 7.20 | Yes | N/A | 2.3 | 2.9 | N/A |
| (basal, undefined) | N/A | 6.70 | Yes | N/A | 2.3 | 2.9 | N/A |
| | N/A | 6.20 | Yes | N/A | 2.3 | 2.9 | N/A |

†= for Media 1, 2, 5, and 10 the hydrolysate/peptone contribution is not included in the estimate of calcium and phosphate concentrations.
N/A indicates not available.

Measurement of precipitation among the samples indicated that the data obtained by the sand-bath method reflects a possible scenario for total heat exposure relative to HTST treatment operations since Media 4 and Media 5 formulations, which had previously not shown operational problems in pilot or manufacturing scale HTST, did show measureable turbidity and visible precipitation in the sand-bath method. Through the sand-bath method, it was determined that calcium and phosphate concentrations, and pH levels are components in media formulations that contribute to significant changes in media during heat exposure of at least 102° C. In several formulations, lowering the pH levels without modifying calcium and phosphate concentrations resulted in precipitation in the media (FIG. 4). The strongest effect influencing medium precipitation is the cross-product of the calcium and phosphate concentration (FIG. 4). This is in agreement with the expected reaction kinetics of insoluble calcium phosphate forms to depend upon both the calcium and the phosphate concentration. In addition, estimating the turbidity by the product of the calcium and phosphate concentrations also agrees with the observation that when either calcium or phosphate concentrations are zero, there will be no significant increase in turbidity (as an estimate for HTST compatibility).

A response surface was subsequently modeled from the DoE turbidity data and the inputs (calcium concentration, phosphate concentration, and pH). The cutoff for a good versus a bad operating regime in the worst-case sand-bath heat treatment was chosen to be a turbidity of 5 NTU based on analysis of all turbidity values relative to visible precipitation from visual inspection of centrifuged and non-centrifuged heat treated media samples. The data suggest that multiple options or levers for modifying a media formulation were possible to ensure HTST-compatibility. Particularly, the lowering of calcium concentrations, phosphate concentrations, pH, or some combination of the three parameters were all potential levers for making a media formulation compatible for HTST treatment or other methods of heat treatment (FIG. 5).

Figure 6:
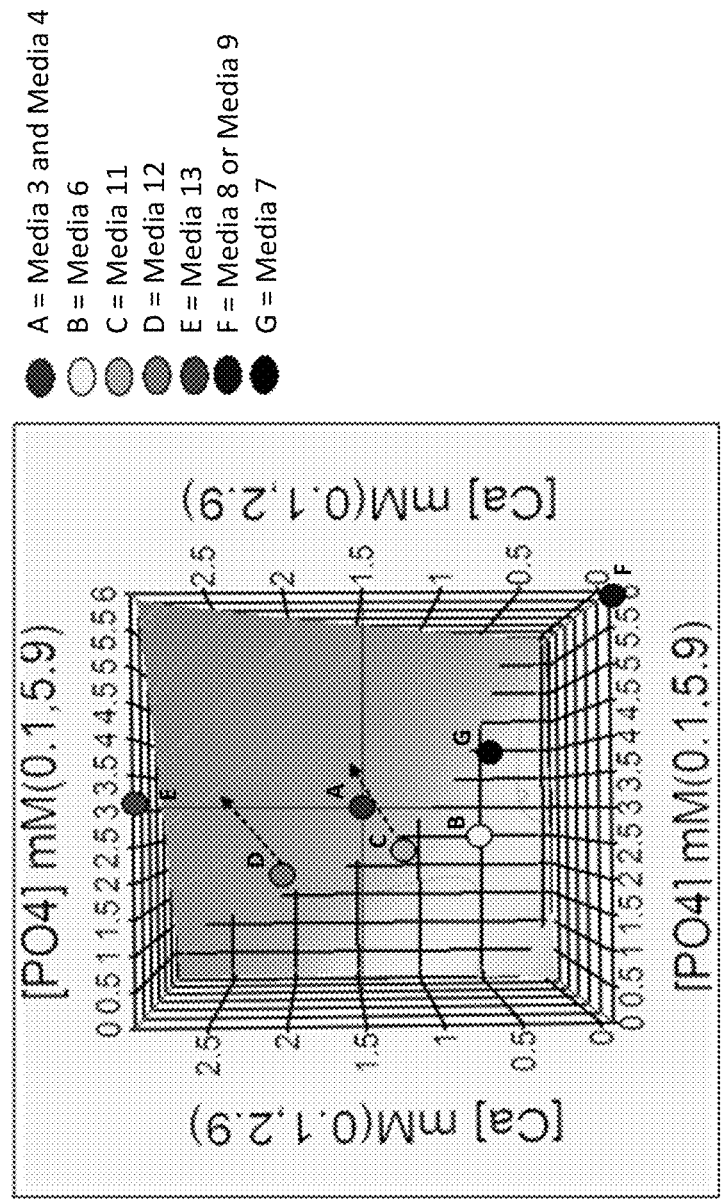
FIG. 6 is a graph depicting media formulations positioned on the Media 4 response surface for pH 7.0 with respect to their known and estimated calcium and phosphate concentrations. Despite the other compositional differences among all the formulations, the calcium and phosphate concentrations strongly correlated with precipitation potential upon heat treatment. Arrow indicates shift of media into the precipitation regime due to addition of hydrolysate containing additional levels of phosphate and/or calcium.

Based on the modeled response surface generated from data on heat treated Media 4, stability of the media in the sand-bath heat treatment studies were particularly dependent on calcium and phosphate concentrations as well as pH levels. To determine modifications in other media formulations that could convert them from HTST incompatible to compatible media, other media formulations not comprising hydrolysate (Media 3, Media 4, Media 6, Media 7, Media 8, Media 9, Media 11, Media 12, and Media 13) were plotted on the model response surface based on their calcium and phosphate concentrations at a pH of 7.0 (FIG. 6). Media containing hydrolysates added complexity to the analysis due to variable levels of calcium and phosphate. Media 11 fell in the area of response surface that indicated it was out of the precipitation range and therefore was determined to likely be HTST compatible (FIG. 6, point C). Addition of hydrolysate to Media 11 for the production of Media 5 (Table 4), and based on known estimates of phosphate and calcium levels in the hydrolysate, resulted in a shift of the media into the precipitation range and was therefore likely to be HTST incompatible (FIG. 6, point C arrow). Media 12 was within the precipitation range and based on the model it was predicted that addition of hydrolysate for the production of Media 2 (Table 4) would shift the media further into the precipitation range (FIG. 6, point D arrow). Formulations predicted to be in or out of the precipitation range based on the model response surface correlated with visible precipitation upon sand-bath heat treatment including the two formulations that had heat exchanger fouling issues in manufacturing scale HTST skid operations. Use of the generated response surface models indicated that there was a strong correlation for precipitation in cell culture media formulation upon heat treatment with respect to high concentrations of calcium and phosphate at near neutral pH (FIGS. 5 and 6). Furthermore, response surface models based on the sand-bath data can be generated to provide recommendation for formulation changes to convert HTST incompatible media into HTST compatible media.

Example 3

Effect of Temperature on Precipitation Behavior of Media During Viral Inactivation Materials and Methods
Media Preparation Media used in this study includes basal production media and batch feed medium. All media was prepared using purified de-ionized water processed through a Millipore SuperQ ultrapure water purification system. Media were prepared using the appropriate media powder stocks (SAFC and Life Technologies). A glass electrode pH probe (Mettler Toledo) and osmometer (Advanced Instruments) were used during liquid preparations to ensure target pH and osmolality for a given preparation. Upon complete dissolution of the components and final pH and osmolality adjustments, the media were filtered using 0.1 μm pore size PES membrane filters into bottles ranging from 250 mL to 1 L (Corning) for small-scale preparations.

pH Adjustment pH drift due to off-gassing that occurred during the time between the completion of the media preparation and when the heat treatment was applied was corrected. Prior to heat treatment, a 30 mL aliquot from each media preparation was transferred to 50 mL tubes (Falcon) and the original Falcon tube caps were replaced with vented caps from 250 mL Corning Erlenmeyer flasks. The tubes were then placed in an incubator with $CO_2$ overlay for 30 minutes to drive down the pH (15% $CO_2$ for pH 6.2 samples and 12% $CO_2$ for all other samples, 200 rpm, 37° C.); this step was able to force the pH below the target. The tubes were manually agitated while monitoring pH using a glass electrode pH probe and meter (Mettler Toledo) until the pH crept back up to target pH. Final pH measurements were taken with NOVA bioprofiler.

Sand-Bath Method

For the sand-bath method, 22 mL of prepared liquid media was transferred to 20 mL glass pressure vessels (Ace glassware). The vessels were sealed with a threaded cap with thermowell so that no air headspace remained in the vessel by filling it full and allowing for excess media to be displaced by the cap and thermowell. The outside of the container was cleaned to prevent fouling of the outside surface from media directly exposed to the heating source matrix. Teflon tape was used to cover the interface between the lip of the glass vessel and the threaded cap to better seal the glass pressure vessel and protect against sand or thermocouple well oil from getting into samples for heat treatment. The fluidized sandbath (Techne SBS-4) with temperature controller (Techne TC-8D) was configured (compressed air inlet pressure=5 psig, bath temperature=110° C.) and was given 30 minutes to equilibrate. Thermocouples attached to a single VWR digital thermometer were inserted in the sample vessel thermowells geometrically situated in the center of the radial dimension of the tube. Silicone oil was added to the thermocouple well to provide a heat transfer medium between the thermocouple well glass wall and the thermocouple. The sample vessels were placed in the sand-bath and a timer was initiated. Temperature kinetic data was recorded approximately every 30-60 seconds. Once a vessel reached 102° C. by thermometer readings, it was maintained in the sand-bath for a 10 second hold. Following the heating and hold steps, the vessels were transferred to a water bath at room temperature until the thermometer temperature reading reached 35° C. After heat treatment, 15 mL of each sample was transferred to a vial for turbidity and visual measurements.

Precipitation Measurements

Media samples were analyzed pre- and post-heat treatment for precipitation by two methods: 1) turbidity via a turbidimeter (2100Q Hach); and 2) centrifugation of the samples in 50-mL Falcon tubes at 10,000×g for 10 minutes (Sorvall RC 6 plus, SS-34 rotor) to sediment precipitates for visual identification and qualitative determination of precipitation based on the pellet size (e.g. none visible, low, moderate, high). Uncentrifuged samples were also analyzed for visual identification of precipitation.

Results

Figure 7:
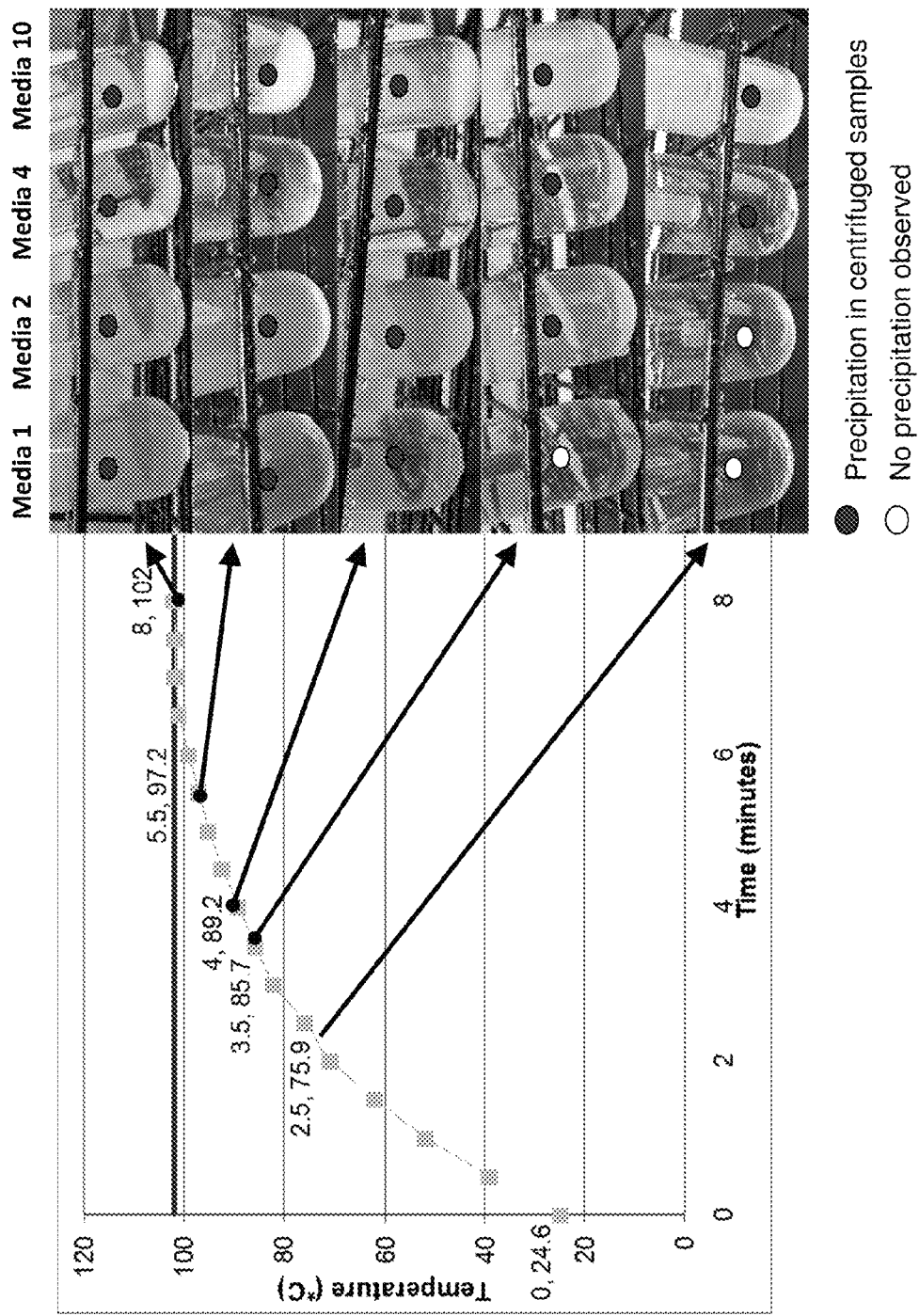
FIG. 7 depicts a graph with the averaged heating profile for four media formulations in the sand-bath system. Five different temperature end-points were taken (denoted by the 2 numbers where, for example, "2.5, 75.9"=samples taken at 2.5 minutes with a resulting average temperature of 75.9° C.). Photos on the right are overlaid with filled or empty circles correlating to visible precipitation observed in either non-centrifuged or centrifuged samples. Empty circle=no precipitation was detected by visual method in non-centrifuged or centrifuged samples. Filled circle=precipitation was detected by visual method in both or one of the samples.
Figure 8:
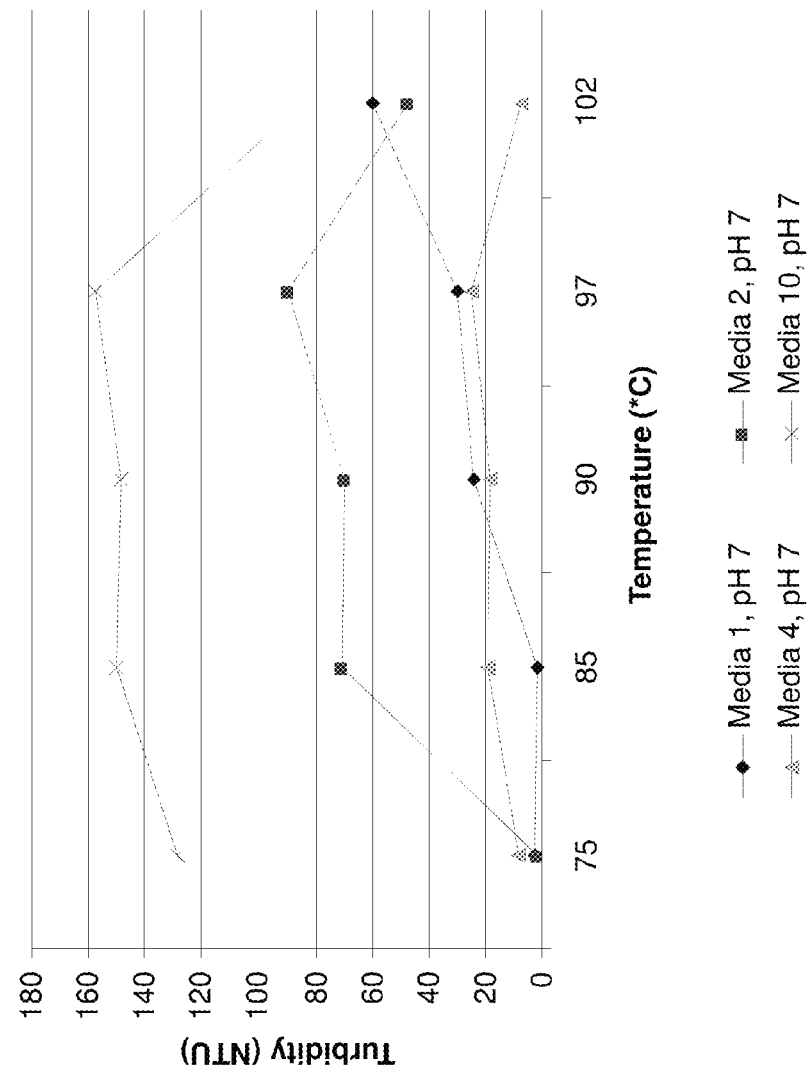
FIG. 8 is a graph depicting turbidity (NTU) values for the 5 different temperature end-point samples taken from 4 different media formulations. Turbidity values greater than ~8 NTU correlated with visible precipitation identification by either direct visual inspection or inspection of centrifuged samples.

The effect of temperature on media precipitation was studied further by varying the target set point for heating in the sand-bath system. Measurements were taken at temperatures of about 75, 85, 90, 97, and 102° C. for Media 1 (feed, undefined), Media 2 (basal, undefined), Media 4 (basal, defined) and Media 10 (basal, undefined) all formulated at a neutral pH 7.0. Visual inspection of non-centrifuged and centrifuged samples taken along the heating curve demonstrated that all of the four different media formulations had precipitation events by the time the samples reached 90° C. (FIG. 7, filled circles). Media 4 and 10 continued to demonstrate precipitation events at lower temperatures of 85° C. and 75° C. (FIG. 7, filled circles). Media 2 demonstrated precipitation events at 85° C. during heat treatment but did not produce visible precipitates at 75° C. indicating that Media 2 is compatible with heat treatment at temperature around 75° C. or less (FIG. 7, empty circle). Media 1 did not produce precipitates at 85° C. indicating that Media 1 is compatible with heat treatment at temperatures around 85° C. or less (FIG. 7, empty circle). These observations were confirmed with turbidity measurements which demonstrated that all four different media formulations had a turbidity measurement of approximately 20 NTU or greater by the time samples reach 90° C. (FIG. 8). Heat treated media turbidity values decreased when going from 97° C. to 102° C. for Media 2, 4, and 10 (FIG. 8). Turbidity in a solution like media is a function of particle size distribution and in particular a specific range of colloidal particle sizes will be more active in the measurement than other portions of the size distribution. Therefore, it is possible the decrease in measured turbidity at the highest temperature is a result of particle flocculation/aggregation behavior leading to a change in the particle size distribution producing an artifact in the turbidity data (e.g. increased particle sized but reduced numbers). These results indicated that slightly reducing temperature while still maintaining virus inactivation did not significantly reduce turbidity.

Temperatures in excess 85° C. to 90° C. at relevant hold times for large scale HTST operation are required to be an effective virus inactivation method and temperatures in excess of 95° C. are required to achieve desired log reductions for the industrially relevant parvoviruses. Although the sand-bath method is more rigorous for observing heat treatment derived media precipitation events, the data suggests operation at lower than the current target HTST treatment set point of 102° C. can be used in order to avoid precipitation events that lead to fouling of the heat exchangers. Since the purpose of the HTST treatment is for viral inactivation, it is clear that lowering the target temperature set point is not an option and that for several media formulations precipitation is a potential operational issue for media HTST applications. Therefore, calcium and phosphate concentrations as well as pH levels are components that can be adjusted to reduce or prevent precipitation events during viral inactivation in media by HTST treatment at temperatures of at least 90° C.

Example 4 pH, Calcium and Phosphate Levels Contribute to Precipitation in Media During Pilot and Large-Scale HTST Media Treatment for Viral Inactivation Materials and Methods
Pilot Scale HTST
For studies using the pilot scale HTST, media formulations were processed from the lowest concentration to the highest concentrations of calcium or phosphate in order to minimize possible carry-over to subsequent runs. Each HTST run required 15 L to 20 L of medium to flush the de-ionized rinse water used between runs and to equilibrate the heating coil to the operating temperature of 102° C. (acceptable range: 97° C.-110° C.) for the HTST process. Following equilibration, approximately 20 L of medium was run through the HTST skid and the outlet flow was collected into a plastic cubitainer. Samples were collected from the medium prior to HTST treatment from the media mix tank and from the outlet medium in the cubitainer, and filtered through a 0.1 μm PVDF capsule membrane filter (Millipore) into a medium storage bag to serve as the "Pre-HTST" and "Post-HTST" samples. All processed and unprocessed filtered media samples were then stored at 2-8° C. prior to use for cell culture performance assays and analytical tests.

Manufacturing Scale HTST
An 1800 L Media 4 or Media 1 preparation was used for a manufacturing-scale engineering run for media heat treatment with a manufacturing scale HTST skid. The purpose of this media preparation was to determine: 1) if the manufacturing mixing conditions for Media 4 were sufficient to meet with the specified quality control recipe mix times, and 2) to generate manufacturing scale HTST treatment performance data with Media 4. Media samples prior to and after HTST treatment were collected by aseptically connecting 6×20-L media bag manifolds (Sartorius Stedim Biotech) to sampling ports on the media mix tank and the destination bioreactor. For samples taken prior to HTST treatment the media was filtered through a 0.1 μm PVDF capsule membrane filter (Millipore) prior to collection and for samples taken post-HTST the media went through the manufacturing filter train which consists of a 0.5/0.2 μm double-layer cartridge filter PVDF pre-filter (Millipore) and a 0.1 μm Nylon final filter (Pall) prior to collection. The samples were then used for cell culture performance assays and analytical tests.

Figure 9:
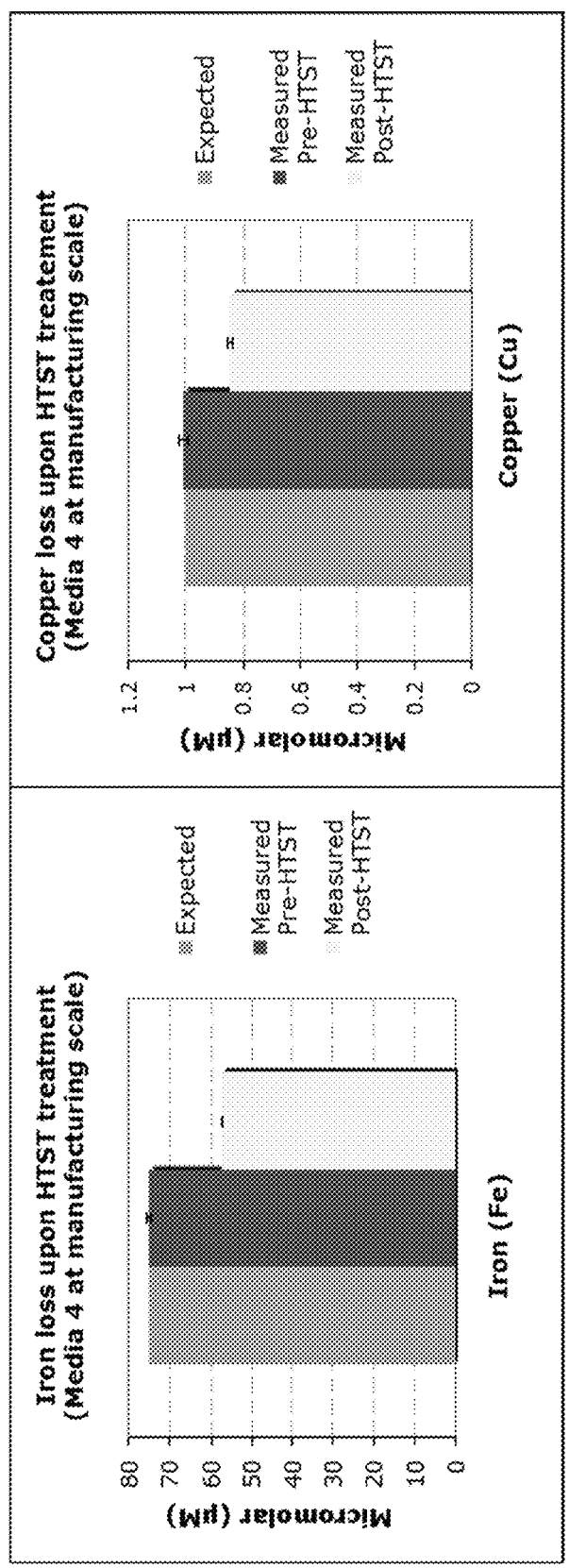
FIG. 9 is a series of graphs showing loss of iron (left panel) and copper (right panel) upon HTST treatment where the HTST processing and filtration operations were successful.

Results
For both pilot and manufacturing scale HTST operations, there were no in-process events leading to the shut-down of the HTST skid or difficulties in controlling the output temperature when desired volumes of Media 4 were processed. Therefore, there was no indication of precipitation events significant enough to lead to fouling of the heat exchanger surfaces or subsequent filtration. The pilot scale processed Media 4 was visually clear of particulates prior to final filtration and use in cell culture. The manufacturing scale processed Media 4 could not be sampled prior to final filtration due to the arrangement of sample ports for the system. Analytical and cell culture performance testing was performed on Media 4 with and without the HTST treatment. Analytical tests for Media 4 showed trace metal losses were occurring upon HTST treatment suggesting that precipitation events were occurring that change media composition concentrations without leading to sufficient precipitation for operational difficulties during the HTST-treatment. For the manufacturing scale HTST treatment of Media 4, data from inductively-coupled plasma mass spectroscopy (ICP-MS) and inductively-coupled plasma optical emission spectroscopy (ICP-OES) assays showed a 24% loss of Fe (iron) and 16% loss of Cu (copper) upon heat treatment relative to non-heat treated Media 4 (FIG. 9).

For both pilot and manufacturing scale HTST operations, there were in-process events leading to the shut-down of the HTST skid and difficulties in controlling the output temperature when desired volumes of Media 1 at pH 7.10 were processed. Precipitation events were significant enough to lead to fouling of the heat exchanger surfaces. The pilot scale processed Media 1 had particulates prior to final filtration and use in cell culture. The manufacturing scale processed Media 1 could not be sampled prior to final filtration due to the arrangement of sample ports for the system. Adjustment of the pH in Media 1 to about pH 6.34 reduced precipitation. For both pilot and manufacturing scale HTST operations, there were no in-process events leading to the shut-down of the HTST skid or difficulties in controlling the output temperature set-point when desired volumes of Media 1 at pH 6.34 were processed. Therefore, there was no indication of precipitation events significant enough to lead to fouling of the heat exchanger surfaces. The pilot scale processed Media 1 was visually clear of particulates prior to final filtration and use in cell culture. The manufacturing scale processed Media 1 could not be sampled prior to final filtration due to the arrangement of sample ports for the system.

Example 5 pH, Calcium, and Phosphate Levels Contribute to Loss of Trace Metals in Media During Heat Treatment for Viral Inactivation Materials and Methods
Media Preparation
Media used in this study includes basal production media and batch feed medium at pH levels ranging from about pH 5.9 to about pH 7.5, calcium concentration ranges from about 0 mM to about 3.5 mM (or greater in undefined media), phosphate concentration ranges from about 0 mM to about 6.5 mM (or greater in undefined media), and iron concentration ranges from about 0 µM to about 125 µM (or greater in undefined media). All media was prepared using purified de-ionized water processed through a Millipore SuperQ ultrapure water purification system. Media were prepared using the appropriate media powder stocks (SAFC and Life Technologies). A glass electrode pH probe (Mettler Toledo) and osmometer (Advanced Instruments) were used during liquid preparations to ensure target pH and osmolality for a given preparation. Upon complete dissolution of the components and final pH and osmolality adjustments, the media were filtered using 0.1 µm pore size PES membrane filters into bottles ranging from 250 mL to 1 L (Corning) for small-scale preparations.

pH Adjustment
pH drift due to off-gassing that occurred during the time between the completion of the media preparation and when the heat treatment was applied was corrected. Prior to heat treatment, a 30 mL aliquot from each media preparation was transferred to 50 mL tubes (Falcon) and the original Falcon tube caps were replaced with vented caps from 250 mL Corning Erlenmeyer flasks. The tubes were then placed in an incubator with $CO_2$ overlay for 30 minutes to drive down the pH (15% $CO_2$ for pH 6.2 samples and 12% $CO_2$ for all other samples, 200 rpm, 37° C.); this step was able to force the pH below the target. The tubes were manually agitated while monitoring pH using a glass electrode pH probe and meter (Mettler Toledo) until the pH crept back up to target pH. Final pH measurements were taken with NOVA bioprofiler.

Sand-Bath Method
For the sand-bath method, 22 mL of prepared liquid media was transferred to 20 mL glass pressure vessels (Ace glassware). The vessels were sealed with a threaded cap with thermowell so that no air headspace remained in the vessel by filling it full and allowing for excess media to be displaced by the cap and thermowell. The outside of the container was cleaned to prevent fouling of the outside surface from media directly exposed to the heating source matrix. Teflon tape was used to cover the interface between the lip of the glass vessel and the threaded cap to better seal the glass pressure vessel and protect against sand or thermocouple well oil from getting into samples for heat treatment. The fluidized sandbath (Techne SBS-4) with temperature controller (Techne TC-8D) was configured (compressed air inlet pressure=5 psig, bath temperature=110° C.) and was given 30 minutes to equilibrate. Thermocouples attached to a single VWR digital thermometer were inserted in the sample vessel thermowells geometrically situated in the center of the radial dimension of the tube. Silicone oil was added to the thermocouple well to provide a heat transfer medium between the thermocouple well glass wall and the thermocouple. The sample vessels were placed in the sand-bath and a timer was initiated. Temperature kinetic data was recorded approximately every 30-60 seconds. Once a vessel reached 102° C. by thermometer readings, it was maintained in the sand-bath for a 10 second hold. Following the heating and hold steps, the vessels were transferred to a water bath at room temperature until the thermometer temperature reading reached 35° C. After heat treatment, 15 mL of each sample was transferred to a vial for turbidity and visual measurements.

Pilot Scale HTST
For studies using the pilot scale HTST, media formulations were processed from the lowest concentration to the highest concentrations of calcium or phosphate in order to minimize possible carry-over to subsequent runs. Each HTST run required 15 L to 20 L of medium to flush the de-ionized rinse water used between runs and to equilibrate the heating coil to the operating temperature of 102° C. (acceptable range: 97° C.-110° C.) for the HTST process. Following equilibration, approximately 20 L of medium was run through the HTST skid and the outlet flow was collected into a plastic cubitainer. Samples were collected from the medium prior to HTST treatment from the media mix tank and from the outlet medium in the cubitainer, and filtered through a 0.1 µm PVDF capsule membrane filter (Millipore) into a medium storage bag to serve as the "Pre-HTST" and "Post-HTST" samples. All processed and unprocessed filtered media samples were then stored at 2-8° C. prior to use for cell culture performance assays and analytical tests.

Manufacturing Scale HTST
An 1800-L engineering run Media 4 preparation was performed in support of an antibody production campaign and the manufacturing scale HTST skid U1281 was used to treat the medium. The purpose of this media preparation was to determine: 1) if the mixing conditions for Media 4 were sufficient to meet with the specified recipe mix times and 2) to generate manufacturing scale HTST treatment performance data with Media 4. Media samples prior to and after HTST treatment were collected by aseptically connecting 6×20-L media bag manifolds (Sartorius Stedim Biotech) to sampling ports on the media mix tank and the destination bioreactor. For samples taken prior to HTST treatment the media was filtered through a 0.1 µm PVDF capsule membrane filter (Millipore) prior to collection and for samples taken post-HTST the media went through the GMP filter train which consists of a 0.5/0.2 µm double-layer cartridge filter PVDF pre-filter (Millipore) and a 0.1 µm Nylon final filter (Pall) prior to collection. The samples were then used for cell culture performance assays and analytical tests.

Precipitation Measurements
Media samples were analyzed pre- and post-heat treatment for precipitation by two methods: 1) turbidity via a turbidimeter (2100Q Hach); and 2) centrifugation of the samples in 50-mL Falcon tubes at 10,000×g for 10 minutes (Sorvall RC 6 plus, SS-34 rotor) to sediment precipitates for visual identification and qualitative determination of precipitation based on the pellet size (e.g. none visible, low, moderate, high). Uncentrifuged samples were also analyzed for visual identification of precipitation.

Analysis for Media Component Concentration Changes

Pre-HTST and post-HTST treated supernatant retains were assayed to screen for any significant changes in measurable media component concentrations. Assays used included: measurement of water-soluble vitamins, measurement of amino acids, and measurement of inorganic phosphate. Trace elements were analyzed using two different inductively-coupled plasma mass spectroscopy (ICP-MS) assays. In addition, samples for iron, copper, and zinc were measured by an inductively-coupled plasma optical emission spectroscopy (ICP-OES) assay for higher throughput quantification of these elements. All statistical analyses when applicable were performed and graphed using JMP software and Excel.

Results

In order to better understand the trace metal losses occurring at the larger manufacturing scales, sand-bath studies were performed using Media 4 as a model medium formulation. To determine if losses of trace metals was associated with the calcium phosphate precipitation events in media containing those components and processed at neutral or higher pH, a half-factorial design was generated to evaluate the effect of varying pH, calcium (Ca), inorganic phosphate (PO4), iron (Fe), and copper (Cu) on recovered Fe and Cu levels following heat treatment (Table 5).

TABLE 5

Concentrations of components tested

| Factors | Concentrations |
|---|---|
| pH | 5.9-7.5 |
| Ca (mM) | 0-3.5 |
| PO4 (mM) | 0-6.5 |
| Fe (µM) | 0-125 |
| Cu (nM) | 0-1750 |

Figure 10:
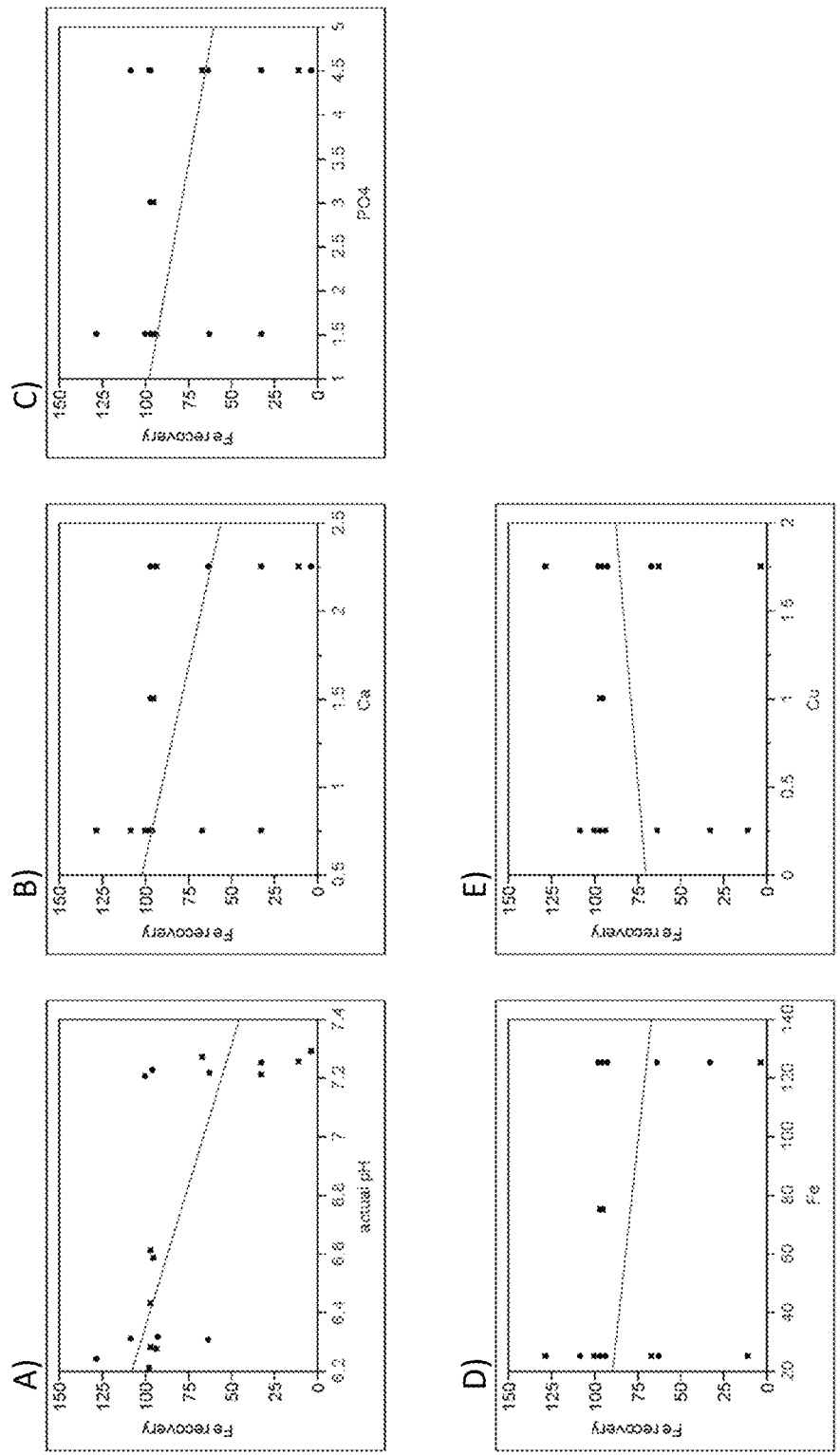
FIG. 10 is a series of graphs demonstrating main effects plots on iron recovery due to varying A) pH levels, B) calcium (Ca) concentrations, C) phosphate (PO4) concentrations, D) iron (Fe) concentrations and E) copper (Cu) concentrations during heat treatment.

Note:
With the exception of the factors above, the other components in the Media 4 were at normal levels Analysis of trace metal recoveries demonstrated that high pH, Ca, and PO4 levels were the main factors responsible for Fe losses (FIG. 10). Increased levels in any one of these three factors lead to lower Fe recoveries. Initial Fe concentrations shows a similar but smaller main effect compared to pH, Ca, and PO4 while Cu shows virtually no effect on Fe recovery. The importance of pH, Ca, and PO4 is in agreement with the possibility that Fe losses are related to calcium phosphate precipitation events that are not noticeable from an operational perspective (e.g., not significant enough to cause HTST skid operational problems) but are noticeable from the perspective of adverse effects of cell culture media performance (e.g., product titer, cell growth, cell viability, and product quality).

Figure 11:
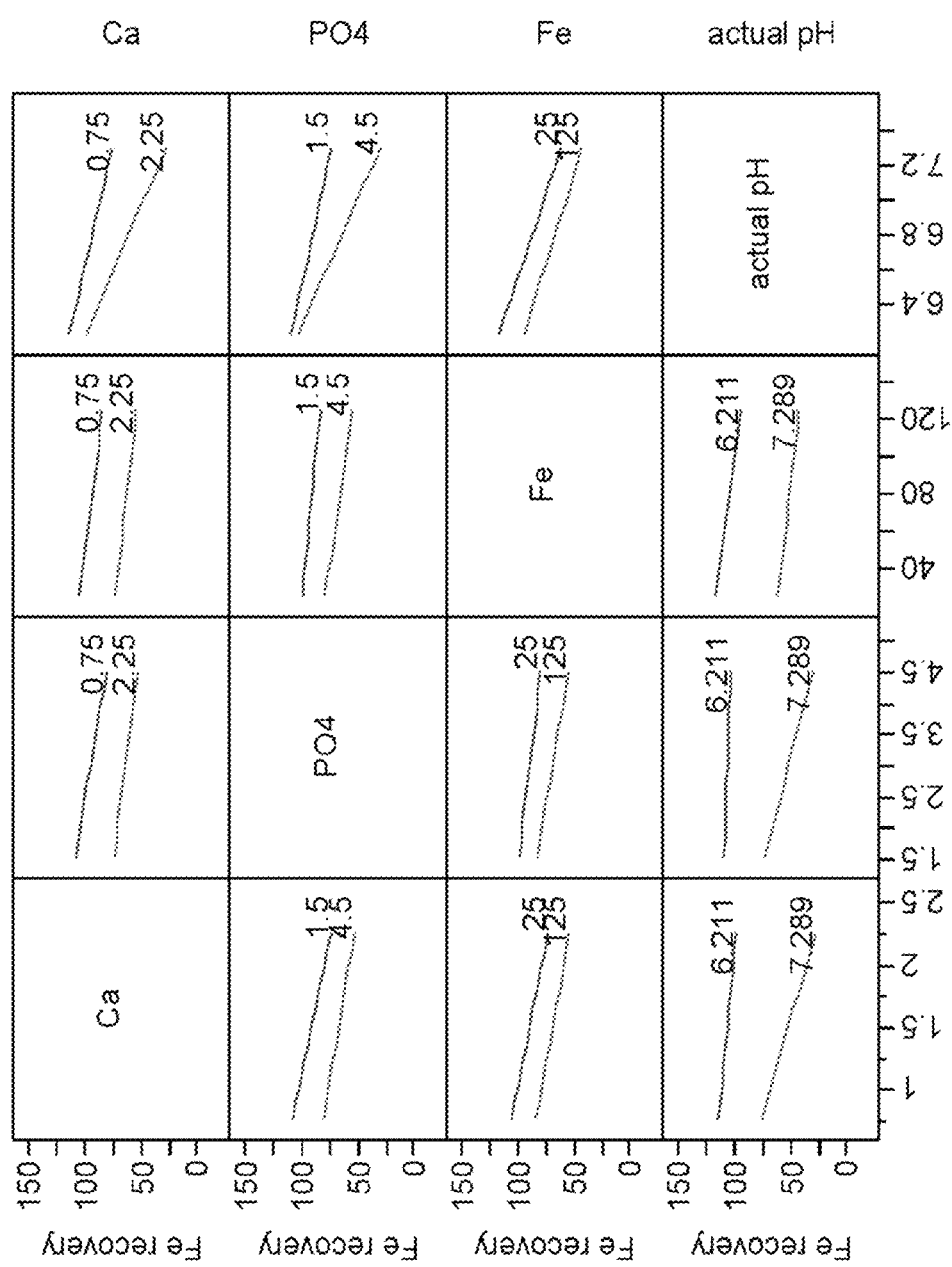
FIG. 11 depicts a series of graphs demonstrating the interaction plot from statistically designed experiments (design of experiments (DoE)) results showing interaction effects between pH, Ca, PO4, and Fe on iron recovery during heat treatment.

In order to explain the variance or spread in the main effects plots, a full factorial model was generated from the data using the four strongest factors (pH, Ca, $PO_4$, and Fe). The interaction plots from this analysis demonstrate two interaction effects that impact Fe recoveries following heat treatment: 1) pH*Ca and 2) pH*PO4 (FIG. 11). These results suggest that reduction of the concentrations of calcium and phosphate, lowering of the pH levels, or lowering some combination of the three factors are needed in order to generate media formulations that avoid Fe losses upon heat treatment. In addition, this data demonstrates that Fe loss occurs even when visible precipitation and increased turbidity are not observed.

Figure 12:
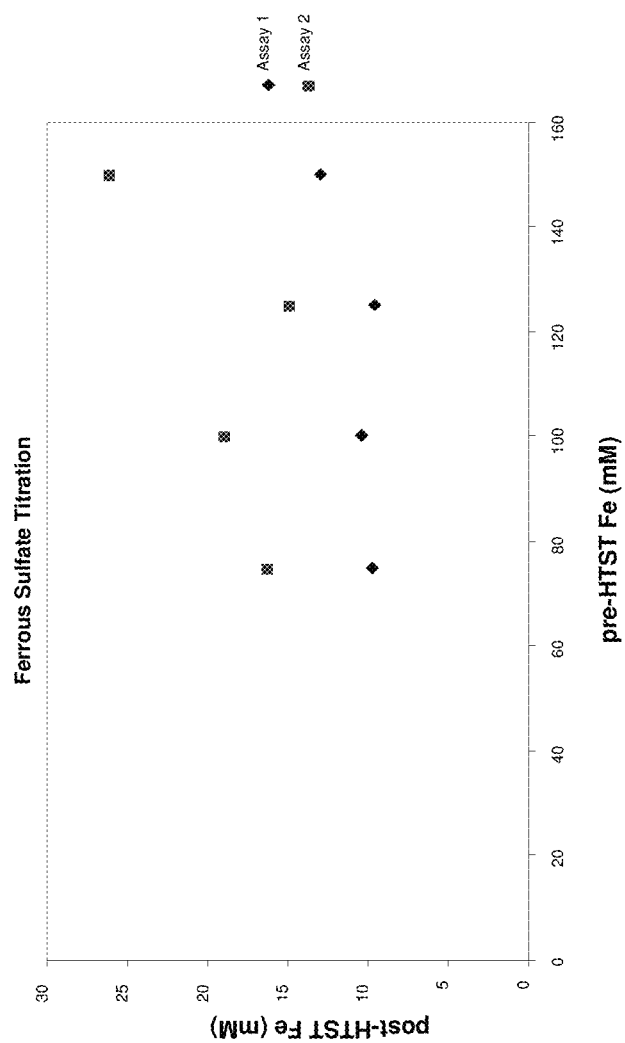
FIG. 12 is a graph showing dependence of final Fe concentration on initial Fe concentration in heat treated media. All other media components were at normal 1.5× Media 4 levels.

Media with ferrous sulfate levels ranging from 75-150 µM (but otherwise equivalent to Media 4) was tested to determine the degree to which post-HTST Fe levels were a function of initial Fe levels. The data show an unexpected non-linear relationship between the initial Fe and post-HTST Fe concentration (FIG. 12). However, it was discovered that the 125 µM Fe sample experienced a pH excursion relative to the other three samples. In both sample sets, the 125 µM Fe sample had the highest pH prior to HTST testing. The pH ranged from 7.08 to 7.17 and 7.09 to 7.14 for Assay 1 and Assay 2 samples sets.

Figure 13:
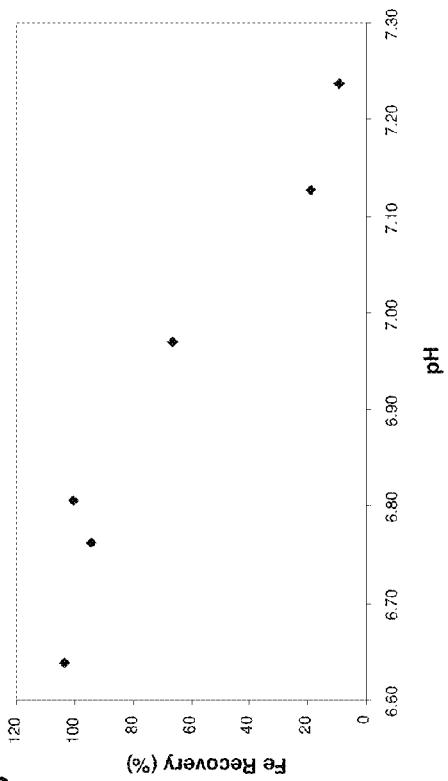
FIG. 13 is a graph showing dependence of Fe recovery on adjustment of several parameters in heat treated media. A) Dependence of Fe recovery on pH levels, and B) dependence of Fe recovery on concentrations of calcium and phosphate in heat treated media. All other media components were at normal 1.5× Media 4 levels. Standard concentrations for Media 4 are indicated by 1 on the x-axis scale.
Figure 13:
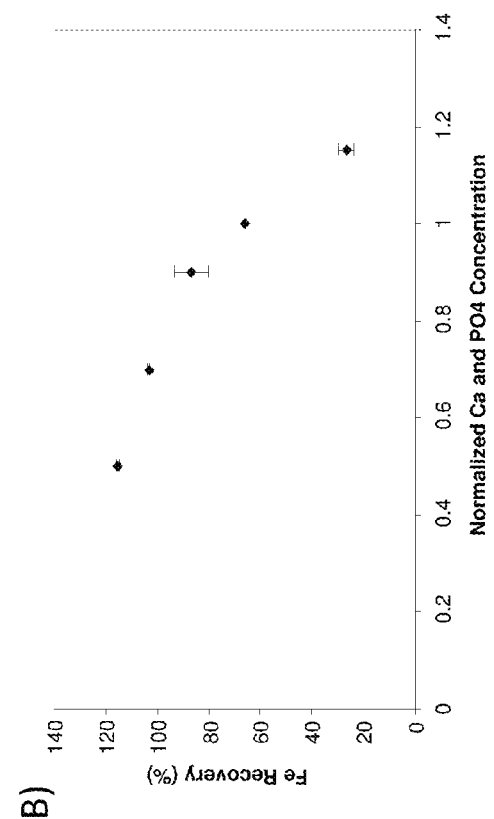

The results from the DoE experiment suggested that media at pH 7.0 was close to the edge of failure in the sand-bath heat treatment system and that Fe loss begins to occur above pH 6.7. Media 4 preparations with pH levels ranging from 6.6 to 7.2 were tested to characterize this regime. Evidence that any pH excursion (even one as small as a fraction of a pH unit) can be significant in the sand-bath heat treatment system was shown in the high-resolution pH titration data (FIG. 13A). After pH 6.8, Fe recovery was highly sensitive to pH, dropping rapidly and reaching a plateau by pH 7.2. This sharp pH dependence suggested that ferrous sulfate titrations results were most likely confounded by pH variability. It also suggests that a very small change in pH (i.e. 0.2 pH units) might place the media formulations in a regime where no Fe losses occur.

The results from the DoE experiment also suggested that large improvements in Fe recovery could be realized with relatively small changes to Ca and PO4 levels (FIG. 13B). Media 4 preparations with Ca and PO4 levels ranging from 0.5-1.17× standard Media 4 levels were tested to better quantify the changes to Ca and PO4 that would be required to realize the previously observed benefit. For this titration, the ratio of Ca and PO4 levels were kept constant at 0.5. Graphical data analysis demonstrated a curved profile with increasing Fe loss correlated with increased Ca and PO4 levels (FIG. 13B). The Media 4 formulation sits on the steepest part of the slope, where large improvements in Fe recovery are possible with small changes to Ca and PO4 concentrations. For example, decreasing the Ca and PO4 concentrations by 30% (and keeping the ratio the same) may yield 100% Fe recovery post-sand-bath heat treatment that can translate to HTST treatment.

Figure 14:
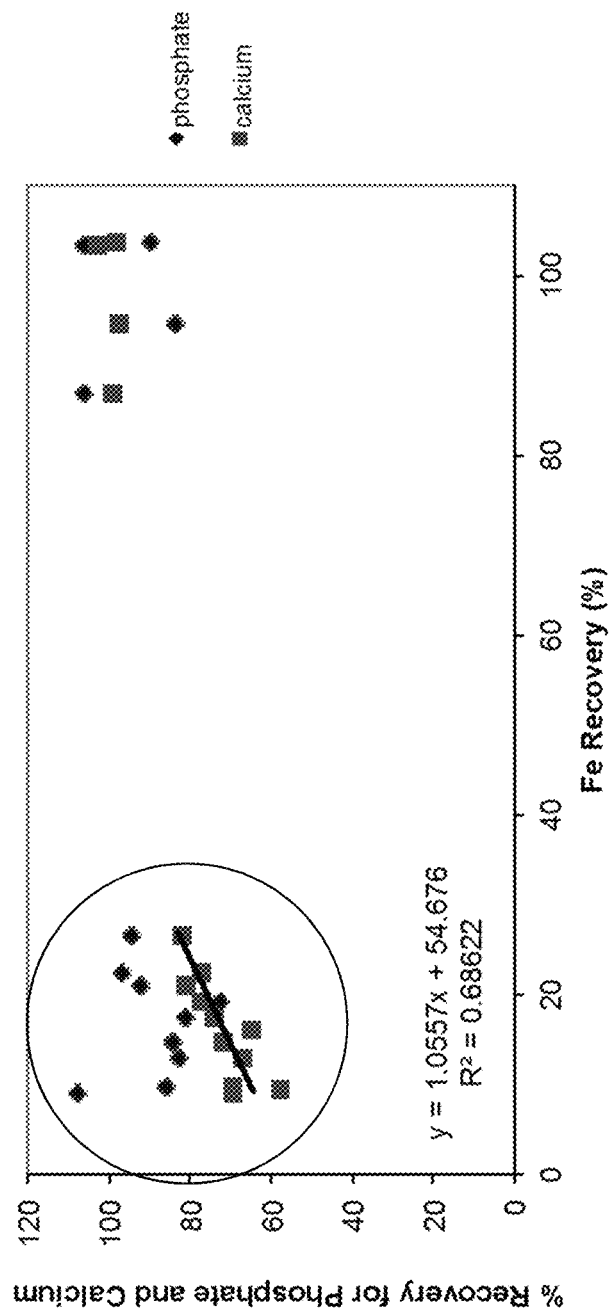
FIG. 14 is a graph demonstrating the relationship of calcium and phosphate recoveries to Fe recoveries following heat treatment. Data points within the red circle indicate samples that showed visible precipitation and increased turbidity (NTU). Line indicates relationship through the calcium data points.

If trace metal losses were correlated to calcium phosphate precipitation, a relationship of calcium and phosphate recovery to Fe recovery would have occurred. Data analysis demonstrated that phosphate recovery did not form a clear relationship with Fe recovery where Fe recoveries were low and precipitation was identified (FIG. 14, diamonds within circle). It is possible that detection of small concentration differences in the relative high initial phosphate concentration sample was difficult due to the signal to noise. Relating this to the possibility that the calcium phosphate was interacting with the iron, a relatively small amount of phosphate could be removed at 1:1 stoichiometry with the iron and it would be difficult to detect the phosphate loss. Another potential cause may be related to the fact that the assay only detects a particular form of inorganic phosphate. Calcium recovery was in the range 60-80% and appeared to be linearly related to Fe recovery in the range of 10-30% where Fe recoveries were low and precipitation was identified (FIG. 14, squares within circle). Analysis of that subset with a least squares regression demonstrated that 69% of the variance in Ca recovery could be explained by Fe recovery. This data shows that Fe is directly linked to Ca recovery.

Pilot scale and manufacturing scale HTST treatment runs for Media 4 (and variations of Media 4) and Media 9 were also performed. Data was gathered from the runs for analytical assays and for cell culture performance studies to assess the impact of HTST treatment on cell culture performance and product quality. No significant losses of any components were identified from the analytical tests with the exception of iron and copper. In addition, no significant changes in key cell culture performance metrics (titer, growth, viability) or product quality (including basic variants) were observed. Copper loss did not result in changes to cell culture performance or levels of basic variants because the losses were not large enough to illicit changes in the host cell line used for testing based on copper titrations for that cell line. Due to the relatively small amounts of trace metals like iron and copper (75 µM and 1 µM, respectively) compared with calcium and phosphate (1.5 mM and 3 mM, respectively) in the Media 4 formulations it was possible that very small calcium phosphate precipitates ($CaPO_4$ complexes) were formed that did not lead to significant fouling of the heat exchangers but that could interact with the iron and copper present in the liquid medium. These interactions of $CaPO_4$ complexes may chelate the iron and copper in some way as to sequester it from the liquid media and deposit it somewhere within the process flow, along with the $CaPO_4$ complexes that precipitate. Regardless of the mechanism, the fact remains that iron and copper losses are observed upon HTST treatment of media, including when the media is treated successfully to inactivate virus. The iron and copper concentration reductions upon HTST treatment could negatively impact the successful use of the HTST-treated media in the subsequent production phase if the losses are significant relative to the required iron and copper concentrations for the production phase.

Figure 15:
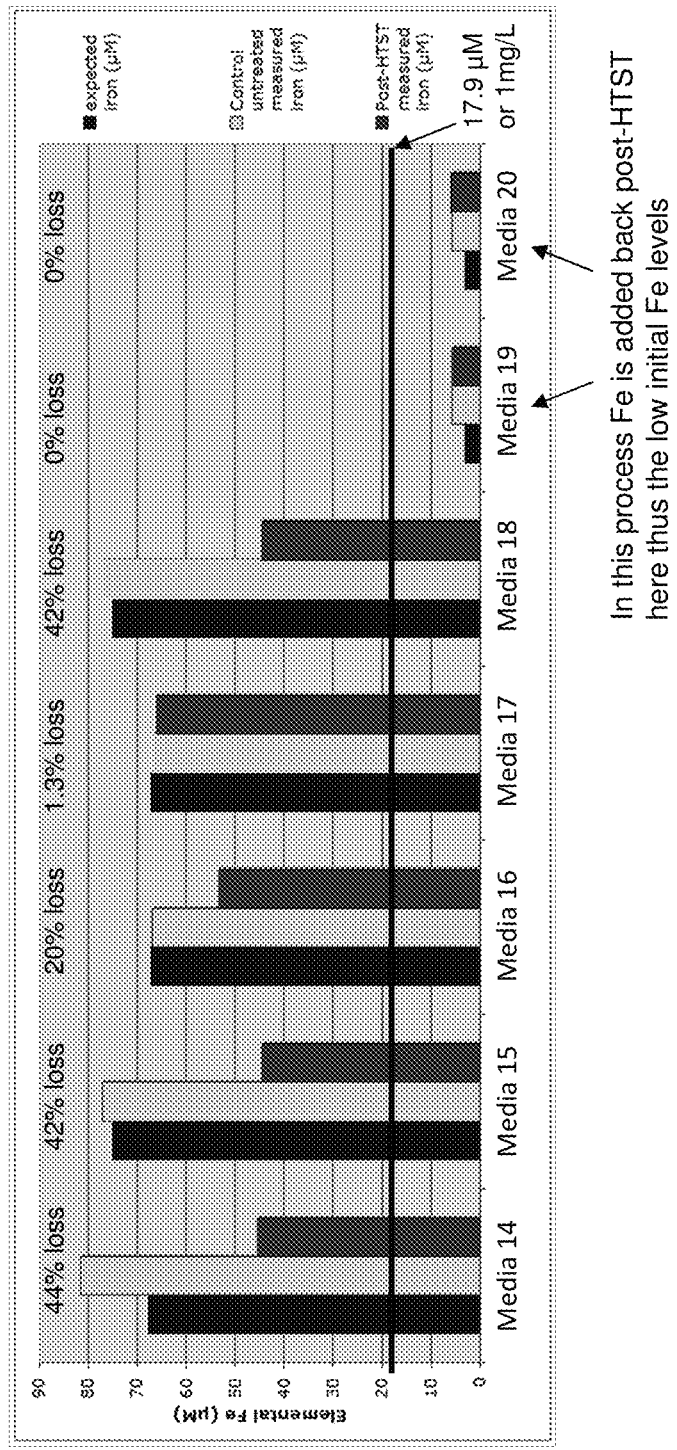
FIG. 15 is a graph demonstrating iron levels in various cell culture media formulations Pre- and Post-HTST treatment. For a particular cell culture media (e.g., Media 14), the left bar indicates expected levels of iron in the cell culture media after HTST treatment, the middle bar indicates actual levels of iron in cell culture media before HTST treatment (Pre-HTST), and the right bar indicates actual levels of iron in cell culture media after HTST treatment (Post-HTST).

Pilot scale and manufacturing scale HTST treatment runs for seven different media formulation were performed. Iron levels in the media formulation were measured pre-HTST treatment and expected levels of iron after HTST treatment were determined. Analysis of iron levels in the media after HTST treatment (post-HTST) demonstrated that HTST treatment resulted in loss of iron levels. Loss of iron was 44% in Media 14, 42% in Media 15, 20% in Media 16, 1.3% in Media 17, and 42% in Media 18 (FIG. 15). Media 19 and Media 20 were supplemented with iron after HTST treatment.

Figure 16:
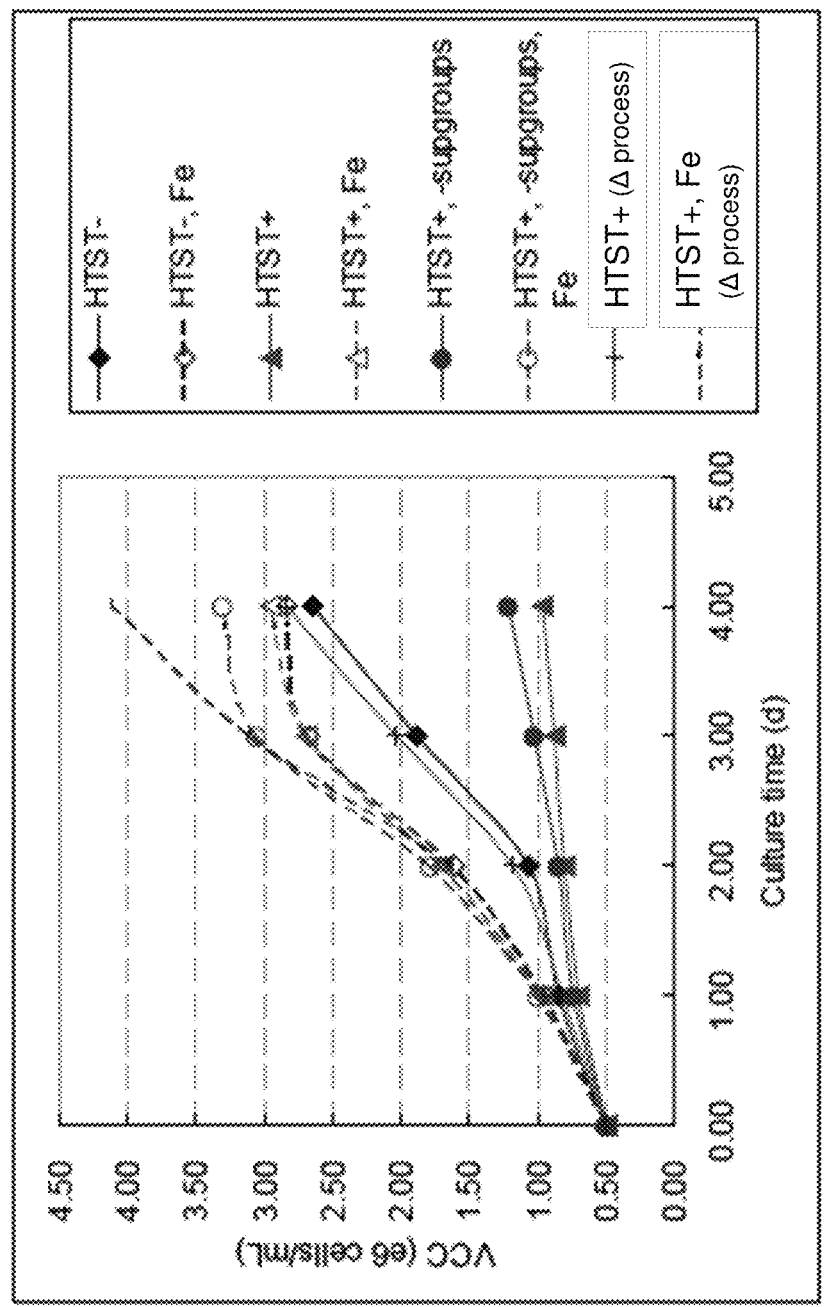
FIG. 16 is a graph demonstrating that addition of iron to HTST treated media is beneficial for growth of the NS0 hybridoma cell line in cell culture. HTST+ indicates cell culture media subjected to HTST treatment. HTST− indicates cell culture media not subjected to HTST treatment. Fe indicates presence of supplemented iron.

Growth of NS0 cells, a murine myeloma cell line, in cell culture media that was subjected to HTST treatment and was supplemented with iron was assayed. Analysis of cell growth demonstrated that cells grown in cell culture media not treated by HTST that was either supplemented or not supplemented with iron grew at comparable amounts over time (FIG. 16). In comparison, cells grew in lower amounts when cultured in media treated with HTST and not supplemented with iron. Addition of iron to HTST treated cell culture allowed recovery of cell growth to higher levels as compared to cell culture media not treated with HTST (FIG. 16).

Overall, this data demonstrated that Fe losses correlated with calcium, phosphate, and pH levels suggesting a close relationship between trace metal losses and calcium phosphate precipitation events during heat treatment, including those events that are not necessarily detectable as visible precipitates, significant turbidity changes, or operational issues. Loss of trace metals such as Fe can adversely affect cell culture performance in various cell lines and product quality.

What is claimed is:

1. A method for inactivating virus or adventitious agents in mammalian cell culture media while the media maintains suitability for cell culture, said method comprising (a) adjusting pH, limiting the total amount of calcium, and/or limiting the total amount of phosphate in the cell culture media prior to high temperature short time (HTST) treatment such that the formation of complexes comprised of calcium and phosphate is suppressed, and (b) subjecting the cell culture media to HTST treatment to inactivate the virus or adventitious agents, wherein the cell culture media comprises
   (i) a calcium concentration of 0 mM to 0.5 mM and a phosphate concentration of 0 mM to 4.5 mM;
   (ii) a phosphate concentration of 0 mM to 1 mM and a calcium concentration of 0 mM to 2.75 mM;
   (iii) a pH of 5.0 to 6.9 and a total amount of calcium and phosphate of less than 10 mM;
   (iv) a pH of 6.4 to 7.4 and a phosphate concentration of 0 mM to 0.5 mM;
   (v) a pH of 6.4 to 6.7 and a phosphate concentration of 0 mM to 3 mM;
   (vi) a pH of 6.4 to 7.2 and a calcium concentration of 0 mM to 0.5 mM; or
   (vii) a pH of 6.4 to 6.7 and a calcium concentration of 0 mM to 1.3 mM.

2. The method of claim 1, further comprising increasing or limiting the concentration of one or more trace metals in the media prior to HTST treatment.

3. The method of claim 2, wherein the one or more trace metals is selected from the group consisting of iron and copper.

4. The method of claim 1, wherein one or more of iron and copper are not present in the media prior to HTST treatment.

5. The method of claim 1, further comprising supplementing one or more of iron and copper to the media following HTST treatment to a suitable level for cell culture.

6. The method of claim 1, wherein the pH is adjusted when the media comprises calcium and phosphate.

7. The method of claim 6, wherein the pH is adjusted in preparing the media prior to HTST treatment to a pH of less than 7.2.

8. The method of claim 6, wherein the pH is adjusted to less than 7.2.

9. The method of claim 6, wherein the pH is adjusted to 5.0 to 7.2.

10. The method of claim 6, further comprising adjusting the pH following HTST treatment to a suitable level for cell culture.

11. The method of claim 10, wherein the pH is adjusted to 6.9 to 7.2.

12. The method of claim 1, wherein the total amount of calcium is limited when the media comprises phosphate.

13. The method of claim 12, wherein the total amount of calcium is limited such that formation of complexes comprised of calcium and phosphate is suppressed.

14. The method of claim 12, wherein calcium is not present in the media prior to HTST treatment.

15. The method of claim 12, wherein the pH is adjusted such that formation of complexes comprised of calcium and phosphate is suppressed.

16. The method of claim 12, further comprising adjusting the calcium level following HTST treatment to a suitable level for cell culture.

17. The method of claim 1, wherein the total amount of phosphate is limited when the media comprises calcium.

18. The method of claim 17, wherein the total amount of phosphate is limited such that formation of complexes comprised of calcium and phosphate is suppressed.

19. The method of claim 17, wherein phosphate is not present in the media prior to HTST treatment.

20. The method of claim 17, wherein the pH is adjusted such that formation of complexes comprised of calcium and phosphate is suppressed.

21. The method of claim 17, further comprising adjusting the phosphate level following HTST treatment to a suitable level for cell culture.

22. The method of claim 1, wherein the total phosphate and calcium concentration in the media is less than 10 mM during HTST treatment.

23. The method of claim 1, wherein the total amount of calcium and phosphate is limited.

24. The method of claim 1, wherein the pH is adjusted, and the total amount of calcium and phosphate is limited.

25. The method of claim 1, wherein precipitate formation is suppressed.

26. The method of claim 1, wherein fouling of equipment used for HTST treatment is reduced.

27. The method of claim 1, wherein filter fouling is suppressed.

28. The method of claim 1, wherein the HTST treatment comprises raising the temperature of the media to at least 85 degrees Celsius for a sufficient amount of time to inactivate virus or adventitious agents in the media.

29. The method of claim 28, wherein the temperature of the media is raised to at least 93 degrees Celsius for a sufficient amount of time to inactivate the virus in the media.

30. The method of claim 29, wherein the temperature is raised for at least 5 seconds.

31. The method of claim 1, wherein the virus is selected from the group consisting of parvoviradae, paramyoxviradae, orthomyxoviradae, bunyaviridae, rhabdoviridae, reoviridae, togaviridae, calciviridae, and picornaviridae.

32. The method of claim 1, wherein the virus is an enveloped virus.

33. The method of claim 1, wherein the virus is a non-enveloped virus.

34. The method of claim 1, wherein the adventitious agent is bacteria.

35. The method of claim 22, wherein the total calcium and phosphate concentration is less than 7 mM.

36. The method of claim 22, wherein the total calcium and phosphate concentration is less than 4 mM.

37. The method of claim 29, wherein the temperature of the media is raised to at least 95 degrees Celsius for a sufficient amount of time to inactivate the virus in the media.

38. The method of claim 29, wherein the temperature of the media is raised to at least 102 degrees Celsius for a sufficient amount of time to inactivate the virus in the media.

39. The method of claim 30, wherein the temperature is raised for at least 10 seconds.

* * * * *